(12) United States Patent
Kim et al.

(10) Patent No.: US 8,673,275 B2
(45) Date of Patent: Mar. 18, 2014

(54) BLOCK COPOLYMERS AND THEIR USE

(75) Inventors: Son Nguyen Kim, Hemsbach (DE); Wolfgang Jahnel, Bellheim (DE)

(73) Assignee: BASF SE, Ludwigshafen (DE)

( * ) Notice: Subject to any disclaimer, the term of this patent is extended or adjusted under 35 U.S.C. 154(b) by 188 days.

(21) Appl. No.: 13/039,155

(22) Filed: Mar. 2, 2011

(65) Prior Publication Data

US 2011/0217255 A1  Sep. 8, 2011

Related U.S. Application Data

(60) Provisional application No. 61/309,460, filed on Mar. 2, 2010.

(51) Int. Cl.
  *A61K 8/72* (2006.01)
  *A61K 8/02* (2006.01)
  *C08F 2/00* (2006.01)

(52) U.S. Cl.
  USPC ........ 424/70.11; 424/401; 526/209; 526/213; 526/217; 526/317.1

(58) Field of Classification Search
  None
  See application file for complete search history.

(56) References Cited

U.S. PATENT DOCUMENTS

| | | | |
|---|---|---|---|
| 2,798,053 A | 7/1957 | Brown | |
| 3,836,597 A | 9/1974 | Boerwinkle et al. | |
| 3,915,921 A | 10/1975 | Schlatzer, Jr. | |
| 4,152,499 A | 5/1979 | Boerzel et al. | |
| 4,237,253 A | 12/1980 | Jacquet et al. | |
| 4,267,103 A | 5/1981 | Cohen | |
| 4,324,780 A | 4/1982 | Jacquet et al. | |
| 4,327,201 A | 4/1982 | Kennedy et al. | |
| 4,375,533 A | 3/1983 | Park et al. | |
| 4,419,502 A | 12/1983 | Sehm | |
| 4,420,596 A | 12/1983 | Lochhead et al. | |
| 4,526,937 A | 7/1985 | Hsu | |
| 4,692,502 A | 9/1987 | Uebele et al. | |
| 4,758,641 A | 7/1988 | Hsu | |
| 4,814,101 A | 3/1989 | Schieferstein et al. | |
| 4,832,702 A | 5/1989 | Kummer et al. | |
| 4,859,210 A | 8/1989 | Franz et al. | |
| 4,946,899 A | 8/1990 | Kennedy et al. | |
| 5,137,980 A | 8/1992 | DeGonia et al. | |
| 5,147,644 A | 9/1992 | Oppenlaender et al. | |
| 5,169,914 A | 12/1992 | Kaszas et al. | |
| 5,286,823 A | 2/1994 | Rath | |
| 5,437,695 A | 8/1995 | Mohr et al. | |
| 5,530,127 A | 6/1996 | Reif et al. | |
| 5,746,786 A | 5/1998 | Mueller et al. | |
| 5,879,420 A | 3/1999 | Kropp et al. | |
| 5,880,252 A | 3/1999 | Kim et al. | |
| 5,883,196 A | 3/1999 | Rath et al. | |
| 5,910,550 A | 6/1999 | Rath | |
| 5,972,856 A | 10/1999 | Kropp et al. | |
| 5,980,594 A | 11/1999 | Kropp et al. | |
| 6,005,144 A | 12/1999 | Kropp et al. | |
| 6,069,281 A | 5/2000 | Kropp et al. | |
| 6,133,209 A | 10/2000 | Rath et al. | |
| 6,140,541 A | 10/2000 | Melder et al. | |
| 6,303,833 B1 | 10/2001 | Grosch et al. | |
| 6,371,999 B1 | 4/2002 | Mohr et al. | |
| 6,407,186 B1 | 6/2002 | Rath et al. | |
| 6,528,575 B1 * | 3/2003 | Schade et al. | 524/559 |
| 6,533,830 B1 | 3/2003 | Oppenlander et al. | |
| 6,932,964 B1 | 8/2005 | Kim et al. | |
| 7,291,681 B2 | 11/2007 | Rath et al. | |
| 7,709,471 B2 | 5/2010 | Halsall et al. | |
| 2003/0015710 A1 | 1/2003 | Vieira et al. | |
| 2004/0133036 A1 | 7/2004 | Zirstein et al. | |
| 2005/0008596 A1 | 1/2005 | Biatry | |
| 2005/0020790 A1 * | 1/2005 | Michl et al. | 526/210 |
| 2008/0199416 A1 | 8/2008 | Kim et al. | |
| 2008/0227871 A1 | 9/2008 | Kim et al. | |
| 2008/0274924 A1 | 11/2008 | Lange et al. | |
| 2010/0081727 A1 | 4/2010 | Hanefeld et al. | |
| 2010/0158280 A1 | 6/2010 | Coronato et al. | |
| 2011/0015280 A1 | 1/2011 | Nguyen Kim et al. | |
| 2011/0150796 A1 | 6/2011 | Kim et al. | |
| 2011/0218295 A1 | 9/2011 | Nguyen Kim et al. | |
| 2011/0218296 A1 | 9/2011 | Nguyen Kim et al. | |
| 2011/0248428 A1 | 10/2011 | Fischer et al. | |
| 2012/0064024 A1 | 3/2012 | Nguyen et al. | |

FOREIGN PATENT DOCUMENTS

| | | |
|---|---|---|
| CA | 2066226 A1 | 3/1991 |
| CA | 2081853 A1 | 5/1993 |

(Continued)

OTHER PUBLICATIONS

U.S. Patent Documents—None.*
Non-Patent Documents—None.*
International Search Report from corresponding PCT App. PCT/EP2011/053000.

*Primary Examiner* — Robert A Wax
*Assistant Examiner* — Jeffrey T Palenik
(74) *Attorney, Agent, or Firm* — Novak Druce Connolly Bove + Quigg LLP

(57) ABSTRACT

A process of free-radical copolymerization of a monomer composition comprising: a) 70 to 100% by weight of acrylic acid, b) 0 to 30% by weight of at least one hydrophilic non-ionic compound, different from a), having a free-radically polymerizable, α,β-ethylenically unsaturated double bond, c) 0 to 1% by weight of at least one free-radically polymerizable crosslinking compound which comprises at least two α,β-ethylenically unsaturated double bonds per molecule, by the method of precipitation polymerization in the presence of an auxiliary composition H) comprising H1) at least one compound with a block structure which comprises at least one hydrophobic group and at least one hydrophilic group, and H2) at least one basic compound different from H1).

28 Claims, No Drawings

(56) References Cited

FOREIGN PATENT DOCUMENTS

| | | | |
|---|---|---|---|
| CA | 2386279 | A1 | 4/2001 |
| DE | 2061057 | A1 | 6/1971 |
| DE | 2150557 | A1 | 6/1972 |
| DE | 2702604 | A1 | 7/1978 |
| DE | 2817369 | A1 | 10/1978 |
| DE | 3708451 | A1 | 10/1988 |
| DE | 3929973 | A1 | 3/1991 |
| DE | 4023593 | A1 | 1/1992 |
| DE | 43 25 158 | A1 | 2/1995 |
| DE | 4333238 | A1 | 4/1995 |
| DE | 4425834 | A1 | 1/1996 |
| DE | 196 20 262 | A1 | 11/1997 |
| DE | 19838851 | A1 | 3/2000 |
| DE | 10117273 | A1 | 10/2002 |
| EP | 145235 | A1 | 6/1985 |
| EP | 206756 | A2 | 12/1986 |
| EP | 0244616 | A2 | 11/1987 |
| EP | 265053 | A2 | 4/1988 |
| EP | 277345 | A1 | 8/1988 |
| EP | 279892 | A2 | 8/1988 |
| EP | 382405 | A2 | 8/1990 |
| EP | 468966 | A1 | 2/1992 |
| EP | 0476485 | A1 | 3/1992 |
| EP | 481297 | A2 | 4/1992 |
| EP | 539821 | A2 | 5/1993 |
| EP | 567810 | A1 | 11/1993 |
| EP | 584771 | A1 | 3/1994 |
| EP | 0628575 | A1 | 12/1994 |
| EP | 0671419 | A1 | 9/1995 |
| EP | 0696572 | A1 | 2/1996 |
| EP | 744413 | A2 | 11/1996 |
| EP | 807641 | A2 | 11/1997 |
| EP | 1209198 | A1 | 5/2002 |
| EP | 1481677 | A1 | 12/2004 |
| GB | 1314700 | A | 4/1973 |
| WO | WO-92/12221 | A1 | 7/1992 |
| WO | WO-92/14806 | A1 | 9/1992 |
| WO | WO-94/24231 | A1 | 10/1994 |
| WO | WO-96/03367 | A1 | 2/1996 |
| WO | WO-96/03479 | A1 | 2/1996 |
| WO | WO-97/03946 | A1 | 2/1997 |
| WO | WO-97/32917 | A1 | 9/1997 |
| WO | WO-99/16775 | A1 | 4/1999 |
| WO | WO-99/31151 | A1 | 6/1999 |
| WO | WO-00/50543 | A1 | 8/2000 |
| WO | WO-01/25293 | A1 | 4/2001 |
| WO | WO-01/25294 | A1 | 4/2001 |
| WO | WO 02/48216 | | 6/2002 |
| WO | WO-98/20053 | A | 9/2003 |
| WO | WO-03/085011 | A1 | 10/2003 |
| WO | WO-2005/048216 | A1 | 5/2005 |
| WO | WO-2007/010034 | A2 | 1/2007 |
| WO | WO-2007/010035 | A1 | 1/2007 |
| WO | WO-2007/012610 | A1 | 2/2007 |
| WO | WO-2008/132083 | A1 | 11/2008 |
| WO | WO 2010/026178 | | 3/2010 |

\* cited by examiner

BLOCK COPOLYMERS AND THEIR USE

CROSS-REFERENCE TO RELATED APPLICATIONS

This application claims the benefit of U.S. Provisional Application 61/309,460 filed on Mar. 2, 2010, the contents of which are incorporated herein by reference in its entirety.

The present invention relates to a process for the preparation of a crosslinked copolymer with anionogenic/anionic groups by free-radical copolymerization by the method of precipitation polymerization, to the copolymers obtained by this process and to their use.

Rheology modifiers, which are often processed in solid, pulverulent form, are used in many technical fields, e.g. coatings, paper production, textile industry, hygiene products, cosmetic and pharmaceutical compositions. The rheology modifiers currently used most often include crosslinked polyacrylic acids.

U.S. Pat. No. 3,915,921 describes copolymers which comprise, in copolymerized form, an olefinically unsaturated carboxylic acid, a $C_{10}$-$C_{30}$-alkyl(meth)acrylate and optionally a crosslinking monomer with at least 2 ethylenically unsaturated double bonds. In neutralized form, they serve as thickeners for various applications.

U.S. Pat. No. 2,798,053 describes copolymers of acrylic acid and polyethers having at least two allyl groups per molecule.

WO 2007/010034 describes an ampholytic copolymer A) obtainable by free-radical copolymerization of
a) at least one compound having a free-radically polymerizable, α,β-ethylenically unsaturated double bond and at least one anionogenic and/or anionic group per molecule,
b) at least one compound which is selected from N-vinylimidazole compounds, N-[3-(dimethylamino)propyl]acrylamide, N-[3-(dimethylamino)propyl]methacrylamide and mixtures thereof, and
c) at least one free-radically polymerizable crosslinking compound which comprises at least two α,β-ethylenically unsaturated double bonds per molecule.

WO 2007/012610 describes a silicone-group-containing copolymer A) obtainable by free-radical copolymerization of
a) at least one compound having a free-radically polymerizable, α,β-ethylenically unsaturated double bond and at least one ionogenic and/or ionic group per molecule,
b) at least one free-radically polymerizable crosslinking compound which comprises at least two α,β-ethylenically unsaturated double bonds per molecule, in the presence of at least one silicone compound c) comprising a polyether group and/or a free-radically polymerizable olefinically unsaturated double bond, where the copolymerization can take place in accordance with the method of precipitation polymerization.

WO 2007/010035 describes the use of an ampholytic copolymer which has a molar excess of anionogenic/anionic groups compared with cationogenic/cationic groups or which has a molar excess of cationogenic/cationic groups compared with anionogenic/anionic groups and which is obtainable by free-radical copolymerization of
a1) at least one compound having a free-radically polymerizable, α,β-ethylenically unsaturated double bond and at least one anionogenic and/or anionic group per molecule,
a2) at least one compound having a free-radically polymerizable, α,β-ethylenically unsaturated double bond and at least one cationogenic and/or cationic group per molecule,
b) at least one free-radically polymerizable crosslinking compound which comprises at least two α,β-ethylenically unsaturated double bonds per molecule,
c) optionally in the presence of at least one silicone compound comprising a polyether group and/or a free-radically polymerizable olefinically unsaturated double bond,
as rheology modifier for hair cosmetic compositions, where the ampholytic copolymer can be prepared by free-radical copolymerization according to the method of precipitation polymerization.

U.S. Pat. No. 4,758,641 (and the equivalent EP 279892) describes a process for the preparation of polymers of olefinically unsaturated $C_3$-$C_5$-carboxylic acids in a solvent which is selected from acetone and lower alkyl acetates, and in the presence of a crosslinker.

U.S. Pat. No. 4,692,502 describes a process for the polymerization of olefinically unsaturated carboxylic acids in an organic solvent and in the presence of ionic surfactants.

U.S. Pat. No. 4,526,937 describes a process for the precipitation polymerization of olefinically unsaturated carboxylic acids in the presence of polyoxyethylene-polyoxypropylene block copolymers with terminal OH groups and an HLB value of greater than 10.

U.S. Pat. No. 4,267,103 describes the solution polymerization of carboxyl-group-containing monomers, where the latter are at least partially neutralized through reaction with an alkali metal hydroxide, ammonia or an amine.

U.S. Pat. No. 4,419,502 describes a process for the precipitation polymerization of olefinically unsaturated carboxylic acids in methylene chloride and in the presence of a polyoxyethylene alkyl ether and/or polyoxyethylene sorbitol ester having an HLB value of greater than 12.

EP 0 584 771 A1 describes a polymer of an olefinically unsaturated carboxylic acid and a steric stabileizer. Suitable steric stableizers are linear block copolymers and random comb polymers with hydrophilic and hydrophobic units.

U.S. Pat. No. 4,375,533 describes a process for the polymerization of olefinically unsaturated carboxylic acids in a polymerization medium in which the carboxylic acid polymer is insoluble, in the presence of a surfactant having an HLB value of less than 10.

U.S. Pat. No. 4,420,596 describes a process for the polymerization of olefinically unsaturated carboxylic acids in a polymerization medium which comprises petroleum spirit in the presence of 1) a sorbitan ester, 2) a nonionic surfactant having an HLB value of less than 10, which is an ester of glycerol or an alkylene glycol and 3) a long-chain alcohol.

EP 1 209 198 A1 describes a polymer composition which comprises A) a crosslinked carboxyl-group-containing polymer and B) at least one compound which is selected from esters of polyhydric alcohols with fatty acids and the alkylene oxide adducts thereof. The polymer composition serves as thickener for various aqueous solutions.

The unpublished European patent application 08163686.2 describes a process for the preparation of a copolymer composition A) by free-radical copolymerization of a monomer composition which comprises acrylic acid and a crosslinker, by precipitation polymerization in the presence of an auxiliary composition H) which comprises H1) glycerol monostearate, and H2) at least one compound with an HLB value in the range from 4 to 10.

It is also known to use polyisobutene polymers with a polar end group in cosmetic or dermatological compositions. For example, EP 1 481 677 A1 describes a topical composition which comprises ascorbic acid, a polyisobutene polymer with a terminal polar group and an N-vinylimidazole polymer.

There is still a need for polymeric thickeners which are highly suitable for adjusting the rheological properties of various products so that they can be formulated e.g. in the form of gels. In this connection, preference is given to pulverulent products which are characterized by a high dissolution rate or redispersion rate. Preferably, the products should be characterized by a high dissolution rate or redispersion rate in aqueous media. Within the context of the invention, aqueous media are water and mixtures of water and at least one water-miscible solvent. The resulting polymer formulations should have high stablety and not have a tendency to form sedimented solid.

Surprisingly, it has now been found that this object is achieved by a polymerization process where the preparation of a crosslinked copolymer having anionogenic and/or anionic groups takes place by free-radical copolymerization by the method of precipitation polymerization in the presence of an auxiliary composition which comprises i) at least one compound with a block structure and ii) at least one compound different from i) which has at least one nitrogen-atom-containing group which is selected from amine groups and ammonium groups.

The invention therefore firstly provides a process for the preparation of a copolymer composition CP) by free-radical copolymerization of a monomer composition comprising
a) 70 to 100% by weight, based on the total weight of the monomers used for the polymerization, of acrylic acid,
b) 0 to 30% by weight, based on the total weight of the monomers used for the polymerization, of at least one water-soluble nonionic compound, different from a), having a free-radically polymerizable, $\alpha,\beta$-ethylenically unsaturated double bond,
c) 0 to 1% by weight, based on the total weight of the monomers used for the polymerization, of at least one free-radically polymerizable crosslinking compound which comprises at least two $\alpha,\beta$-ethylenically unsaturated double bonds per molecule,
by the method of precipitation polymerization in the presence of an auxiliary composition H) comprising
H1) at least one compound with a block structure which comprises at least one hydrophobic block and at least one hydrophilic block, and
H2) at least one basic compound different from H1).

In one preferred embodiment, the component H2) is selected from basic compounds different from H1) which have at least one nitrogen-atom-containing group which is selected from amine groups and ammonium groups.

In a further preferred embodiment, the monomer composition used for the preparation of the copolymer composition CP) comprises
a) 70 to 99.99% by weight, based on the total weight of the monomers used for the polymerization, of acrylic acid,
b) 0 to 29.99% by weight, based on the total weight of the monomers used for the polymerization, of at least one hydrophilic nonionic compound, different from a), having a free-radically polymerizable, $\alpha,\beta$-ethylenically unsaturated double bond,
c) 0.01 to 1% by weight, based on the total weight of the monomers used for the polymerization, of at least one free-radically polymerizable crosslinking compound which comprises at least two $\alpha,\beta$-ethylenically unsaturated double bonds per molecule.

The invention further provides a copolymer composition CP) obtainable by the process described above and below.

The invention further provides the use of such a copolymer composition CP) or a copolymer obtainable therefrom in an aqueous composition for modifying the rheological properties of this composition.

The invention further provides an active ingredient or effect substance composition comprising
A) at least one copolymer composition CP) obtainable by a process as defined above and below,
B) at least one active ingredient or effect substance and
C) optionally at least one further auxiliary different from A) and B).

The invention further provides a cosmetic composition comprising
A) at least one copolymer composition CP) obtainable by a process as defined above and below,
B) at least one cosmetically acceptable active ingredient and
C) optionally at least one further cosmetically acceptable auxiliary different from CP) and B).

The invention further provides a pharmaceutical composition comprising
A) at least one copolymer composition CP) obtainable by a process as defined above and below,
B) at least one pharmaceutically acceptable active ingredient and
C) optionally at least one further pharmaceutically acceptable auxiliary different from A) and B).

The invention further provides the use of a copolymer composition CP) obtainable by a process as defined above and below in the food sector for modifying rheological properties.

The invention further provides the use of a copolymer composition CP) obtainable by a process as defined above and below as auxiliary in pharmacy, preferably as or in (a) coating composition(s) for solid medicament forms, for modifying rheological properties, as surface-active compound, as or in (an) adhesive(s) and as or in (a) coating composition(s) for the textile, paper, printing and leather industry.

The invention further provides the use of a block copolymer as defined above and below as auxiliary for the preparation of a copolymer composition CP) by free-radical copolymerization of a monomer composition comprising
a) 70 to 100% by weight, based on the total weight of the monomers used for the polymerization, of acrylic acid,
b) 0 to 30% by weight, based on the total weight of the monomers used for the polymerization, of at least one water-soluble nonionic compound, different from a), having a free-radically polymerizable, $\alpha,\beta$-ethylenically unsaturated double bond,
c) 0 to 1% by weight, based on the total weight of the monomers used for the polymerization, of at least one free-radically polymerizable crosslinking compound which comprises at least two $\alpha,\beta$-ethylenically unsaturated double bonds per molecule,
by the method of precipitation polymerization.

Preference is given to the use of a block copolymer as defined above and below as auxiliary for the preparation of a copolymer composition CP) by free-radical copolymerization of a monomer composition comprising
a) 70 to 99.99% by weight, based on the total weight of the monomers used for the polymerization, of acrylic acid,
b) 0 to 29.99% by weight, based on the total weight of the monomers used for the polymerization, of at least one hydrophilic nonionic compound, different from a), having a free-radically polymerizable, $\alpha,\beta$-ethylenically unsaturated double bond, c) 0.01 to 1% by weight, based on the total weight of the monomers used for the polymerization, of at least one free-radically polymerizable crosslinking compound which comprises at least two α,β-ethylenically unsaturated double bonds per molecule.

The use of the auxiliary system according to the invention for the preparation of CP) by precipitation polymerization brings with it at least one of the following advantages:

The copolymer composition based on this auxiliary system can be dried easily; the resulting dry compositions are very readily redispersible and are characterized by a high dissolution rate;

the copolymer composition based on this auxiliary system can be easily formulated as a stable liquid composition of high concentration (e.g. as so-called stock solution) and be further processed to give products;

even in a physiologically compatible pH range of about 5 to 9, very good thickening properties are achieved;

the reaction mixture during the preparation of the copolymer composition CP) has a lower viscosity, meaning that the heat of reaction can be better dissipated;

in the case of the reaction and/or the formulations, relatively high solids contents are made possible;

deposit formation in the polymerization reactor can generally be successfully avoided;

the lower viscosity and/or the high solids contents render the process more economical;

the resulting gels are characterized by at least one of the following application properties: very good clarity, very good structure, good ability to be washed out.

Within the context of the present invention, the expression alkyl comprises straight-chain and branched alkyl groups. Suitable short-chain alkyl groups are, for example, straight-chain or branched $C_1$-$C_7$-alkyl groups, preferably $C_1$-$C_6$-alkyl groups and particularly preferably $C_1$-$C_4$-alkyl groups. These include, in particular, methyl, ethyl, propyl, isopropyl, n-butyl, 2-butyl, sec-butyl, tert-butyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, etc.

Suitable relatively long-chain $C_8$-$C_{30}$-alkyl groups and $C_8$-$C_{30}$-alkenyl groups are straight,β-chain and branched alkyl and alkenyl groups. These are preferably predominantly linear alkyl radicals, as also occur in natural or synthetic fatty acids and fatty alcohols and also oxo alcohols, or are predominantly linear alkenyl radicals as also occur in natural or synthetic fatty acids and fatty alcohols and also oxo alcohols, which may be mono-, di- or polyunsaturated. Suitable relatively long-chain $C_8$-$C_{30}$-alkyl groups are, for example, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, arachinyl, behenyl, lignocerinyl, melissinyl, etc. Suitable relatively long-chain $C_8$-$C_{30}$-alkenyl groups comprise, for example, n-octenyl, n-nonenyl, n-decenyl, n-undecenyl, n-dodecenyl, n-tridecenyl, n-tetradecenyl, n-pentadecenyl, n-hexadecenyl, n-heptadecenyl, n-octadecenyl, n-nonadecenyl, n-eicosenyl, n-docosenyl, n-tetracosenyl, hexacosenyl, triacontenyl, etc.

Cycloalkyl is preferably $C_5$-$C_8$-cycloalkyl, such as cyclopentyl, cyclohexyl, cycloheptyl or cyclooctyl.

Aryl comprises unsubstituted and substituted aryl groups and is preferably phenyl, tolyl, xylyl, mesityl, naphthyl, fluorenyl, anthracenyl, phenanthrenyl, naphthacenyl and in particular phenyl, tolyl, xylyl or mesityl.

In the text below, compounds which can be derived from acrylic acid and methacrylic acid are sometimes referred to for short by adding the syllable "(meth)" to the compound derived from acrylic acid.

The copolymer compositions CP) according to the invention can advantageously be formulated as gels under normal conditions (20° C.). "Gel-like consistency" indicates formulations which have a higher viscosity than a liquid and which are self-supporting, i.e. which retain a shape imparted to them without shape-stableizing covering. In contrast to solid formulations, gel-like formulations, however, can be readily deformed under the application of shear forces. The viscosity of the gel-like compositions is preferably in a range from greater than 600 to about 60 000 mPas, particularly preferably from 6000 to 30 000 mPas. The gels are preferably hair gels.

Within the context of the present invention, water-soluble monomers and polymers are to be understood as meaning monomers and polymers which dissolve in water to at least 1 g/l at 20° C. Water-dispersible monomers and polymers are to be understood as meaning monomers and polymers which disintegrate into dispersible particles under application of shear forces, for example by stirring. Hydrophilic monomers are preferably water-soluble or at least water-dispersible. The copolymers present in the copolymer compositions CP) according to the invention are generally water-soluble.

Within the context of the invention, a group reactive towards isocyanate groups is preferably understood as meaning a hydroxyl group, a primary amino group or a secondary amino group.

H1) Compound with a Block Structure

The compound H1 is preferably selected from compounds of the general formulae (I), (II) or (III)

$$(A)_n\text{-}X\text{---}(B)_m \qquad (I)$$

$$[A\text{-}X]_p\text{---}B \qquad (II)$$

$$(A)\text{-}[X\text{---}B]_q \qquad (III)$$

in which
n is an integer of at least 1,
m is an integer of at least 1,
p is an integer of at least 2,
q is an integer of at least 2,
A is a hydrophobic group, where
  in the compounds of the formulae (I) and (II), the groups A can in each case have identical or different meanings and in each case have one binding site to the group X,
  in the compounds of the formula (III), the group A has q binding sites to each of the groups X,
X in the compounds of the formula (I) is a chemical bond or a (n+m) valent organic radical and in the compounds of the formulae (II) and (III) is a chemical bond or a bivalent organic radical,
B is a hydrophilic group.

Hydrophobic Group of H1)

Preferably, in the compounds of the general formulae (I), (II) or (III), at least one of the groups A or B is a polymeric group with a number-average molecular weight in a range from 150 to 1 000 000, particularly preferably 250 to 500 000.

Preferably, in the compounds H1), the hydrophobic group is selected from
  $C_8$-$C_{30}$-alkyl groups,
  polyisobutenyl groups,
  polytetrahydrofuran groups, polyester groups,
polysilicone groups,
and combinations thereof.

Specifically, the hydrophobic group A in the compounds of the general formulae (I), (II) or (III) is selected from
$C_8$-$C_{30}$-alkyl groups,
polyisobutenyl groups,
polytetrahydrofuran groups,
polyester groups,
polysilicone groups,
and combinations thereof.

Suitable $C_8$-$C_{30}$-alkyl groups are straight-chain and branched $C_8$-$C_{30}$-alkyl groups. Preferably, these are predominantly linear alkyl radicals as also occur in natural or synthetic fatty acids and fatty alcohols and also oxo alcohols, or predominantly linear alkenyl radicals as also occur in natural or synthetic fatty acids and fatty alcohols, and also oxo alcohols, which may be mono-, di- or polyunsaturated. Suitable relatively long-chain $C_8$-$C_{30}$-alkyl groups are e.g. n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, arachinyl, behenyl, lignocerinyl, melissinyl, etc.

Polyisobutenyl groups suitable as hydrophobic group may be linear or branched. Here, the polyisobutenyl group may be composed only of isobutene units or else comprise comonomers in copolymerized form. Preference is given to essentially homopolymeric polyisobutenyl groups. Within the context of the present invention, these are understood as meaning those polyisobutenyl groups which are composed to at least 85% by weight, preferably to at least 90% by weight and particularly preferably to at least 95% by weight, of isobutene units [—$CH_2C(CH_3)_2$—]. The fraction of comonomers is preferably less than 15% by weight, particularly preferably less than 10% by weight, especially less than 5% by weight, based on the total weight of the polyisobutenyl group. Preferred comonomers are vinylaromatics, olefins having 4 to 10 carbon atoms different from isobutene, and mixtures thereof. The comonomers are preferably selected from styrene, $C_1$-$C_4$-alkylstyrenes, such as 2-, 3-, 4-methylstyrene and 4-tert-butylstyrene, 2-methylbutene-1,2-methylpentene-1,2-methylhexene-1,2-ethylpentene-1,2-ethylhexene-1,2-propylheptene-1,1-butene, cis-2-butene, trans-2-butene and mixtures thereof.

The polyisobutenyl groups preferably have a number-average molecular weight $M_n$ of from 150 to 10 000, particularly preferably from 200 to 6 000, in particular from 300 to 4 000.

The polyisobutenyl groups preferably have a narrow molecular weight distribution. The polydispersity is preferably at most 1.4, particularly preferably at most 1.3, in particular at most 1.2. Polydispersity is understood as meaning the quotient of weight-average molecular weight $M_w$ and number-average molecular weight $M_n$ (PDI=$M_w/M_n$).

The preparation of compounds H1) with polyisobutenyl groups preferably proceeds from "high-reactivity" polyisobutenes. "High-reactivity" polyisobutenes differ from the "low-reactivity" polyisobutenes by virtue of the content of terminally arranged double bonds. For example, high-reactivity polyisobutenes comprise at least 50 mol %, based on the total number of polyisobutene macromolecules, of terminally arranged double bonds. Particular preference is given to polyisobutenes with at least 60 mol % and in particular with at least 80 mol %, based on the total number of polyisobutene macromolecules, of terminally arranged double bonds. The terminally arranged double bonds may either be vinyl double bonds [—CH=$C(CH_3)_2$] (β-olefin) and also vinylidene double bonds [—CH—C(=$CH_2$)—$CH_3$] (α-olefin). Moreover, as mentioned, essentially homopolymeric polyisobutenes are used for the preparation of compounds H1). Within the context of the present invention, these are understood as meaning those polyisobutenes which are composed to at least 85% by weight, preferably to at least 90% by weight and particularly preferably to at least 95% by weight, of isobutene units [—$CH_2C(CH_3)_2$—].

Suitable polyisobutenes for the preparation of compounds H1) are all polyisobutenes obtainable by customary cationic or living cationic polymerization. However, preference is given to so-called "high-reactivity" polyisobutenes, which have already been described above.

Suitable polyisobutenes for the preparation of compounds H1) are for example the Glissopal grades from BASF SE, thus e.g. Glissopal® 1000, Glissopal® 1300, Glissopal® 2300, Glissopal® SA, Glissopal® V 190, Glissopal® V 230, Glissopal® V 500, Glissopal® V 640, Glissopal® V 700 and Glissopal® V 1500.

Processes for the preparation of polyisobutenes suitable for the preparation of compounds H1) are known, for example from DE-A 27 02 604, EP-A 145 235, EP-A 481 297, EP-A 671 419, EP-A 628 575, EP-A 807 641 and WO 99/31151. Polyisobutenes which are prepared by living cationic polymerization of isobutene- or isobutene-containing monomer mixtures are described for example in U.S. Pat. No. 4,946,899, U.S. Pat. No. 4,327,201, U.S. Pat. No. 5,169,914, EP-A 206 756, EP-A 265 053, WO 02/48216 and in J. P. Kennedy, B. Ivan, "Designed Polymers by Carbocationic Macromolecular Engineering", Oxford University Press, New York 1991. Reference is hereby made to these and other publications which describe polyisobutenes in their entirety.

The preparation of compounds H1) with polyisobutenyl groups preferably proceeds from polyisobutenes which are selected from:
high-reactivity polyisobutenes,
polyisobutenes with at least one nitrogen-containing end group,
polyisobutenyl alcohols,
polyisobutenyl aldehydes,
polyisobutenes having at least one carboxylic acid end group or a derivative thereof,
mixtures of two or more than two of the aforementioned compounds.

The preparation of compounds H1) with polyisobutenyl groups preferably proceeds from high-reactivity polyisobutenes or polyisobutenes functionalized in another way which are suitable for the bonding of at least one hydrophilic group. The polyisobutenes functionalized in another way can be obtained e.g. from high-reactivity polyisobutenes by single- or multi-stage functionalization of the terminal double bond.

In a first embodiment, for the preparation of compounds H1) with at least one polyisobutenyl group as hydrophobic group, a high-reactivity polyisobutene is used.

In a second embodiment, for the preparation of compounds H1) with at least one polyisobutenyl group as hydrophobic group, a polyisobutene with at least one nitrogen-containing end group is used.

The nitrogen-containing end group can comprise one or more nitrogen atoms. Preferably, the nitrogen-containing end group has 1, 2, 3, 4, 5, 6, 7, 8, 9 or 10 nitrogen atoms. The nitrogen atoms can be incorporated into the nitrogen-containing end group for example in the form of amino groups, imino groups or amide groups. Suitable amino groups are primary, secondary or tertiary amino groups.

In one specific embodiment, for the preparation of compounds H1) with at least one polyisobutenyl group as hydrophobic group, a polyisobutene with at least one nitrogen-containing end group is used which has at least one primary or secondary amino group. These are advantageously suitable for the further reaction for the preparation of the compounds H1) with at least one compound having at least one hydrophilic group. The bonding can take place here also through reaction of at least one polyisobutene with at least one nitrogen-containing end group with at least one compound having at least one hydrophilic group and with a further compound which is capable of reacting with both. These include e.g. the linkage by means of polyisocyanates, as described in detail below.

Preferably, there are 1 to 10 amino groups per terminal group. Further preferably, the amino groups are selected from primary, secondary and/or tertiary amino groups. These may be for example groups derived from straight-chain or branched alkylenepolyamines. Besides the nitrogen functionalities, the nitrogen-containing end groups can also comprise other functionalities. These include in particular oxygen-containing functional groups such as OH groups or ether groups.

Polyisobutenes with at least one nitrogen-containing end group (also referred to as polyisobutenamines or PIBA) and processes for their preparation are known. Overviews of suitable processes for amino functionalization can be found in WO 03/085011 and the literature cited therein, specifically EP-A 382 405, WO 98/20053 and the documents listed below. Moreover, the literature describes numerous processes for the preparation of OH- or aldehyde-functionalized polyisobutenes (see e.g. EP-A 468 966). The polyisobutene derivatives prepared in this way can be amino-functionalized in a manner known per se by reductive amination. Examples of suitable functionalization processes are the functionalization processes (1) to (8) known from the literature and listed below:

(1) Reaction of the polyisobutene to give polyisobutenylsuccinic anhydrides (PIBSAs) and further reaction with ammonia or amines;
(2) hydroformylation of the polyisobutene with subsequent reductive amination of the hydroformylation product in the presence of ammonia, amines or amino alcohols or hydroformylation of the polyisobutene in the presence of ammonia or amines under reducing conditions as described in EP-A 244 616 or WO 94/24231;
(3) hydroboration of the polyisobutene with subsequent oxidative cleavage of the borane adduct (see J. P. Kennedy and B. Ivan "Designed Polymers by Carbocationic Macromolecular Engineering", p. 178f.) and subsequent reductive amination in the presence of ammonia or amines in a manner known per se;
(4) hydroboration or hydroformylation under reducing conditions to give a polyisobutenyl alcohol, followed by an alkoxylation and a reductive amination in the presence of ammonia or amines (see EP-A 277 345, WO 98/20053 and WO 00/50543);
(5) reaction of the polyisobutene with a nitrogen oxide-containing oxidant and subsequent reduction of the $NO_x$ groups introduced in this way to $NH_2$ groups, cf. e.g. DE-A 4425834, WO 96/03367, WO 96/03479, WO 97/03946;
(6) epoxidation of the polyisobutene and subsequent reaction of the epoxidation product with ammonia, an amine or an amino alcohol, optionally with subsequent or simultaneous elimination of water and catalytic reduction, cf. e.g. WO 92/12221, WO 92/14806, EP-A 476 485, EP 539 821, EP-A 696572 and DE-A 19620262;
(7) hydrocyanation of the polyisobutene with acidic catalysis and subsequent hydrolysis in the sense of a Ritter reaction as described in DE-OS 2061057 or EP-A 567 810 (as regards the Ritter reaction, see also Houben-Weyl, E5, pp. 1032-1041 (1985) or Houben-Weyl, XI/1, p. 994 f. (1957); or
(8) reaction of the polyisobutene with phenol under Friedel-Crafts conditions and subsequent reaction of the polyisobutenylphenol with formaldehyde and amine in the sense of a Mannich reaction (see e.g. WO 01/25293 and WO 01/25294).

Preferably, the amines for the preparation of polyisobutenes having at least one nitrogen-containing end group are selected from ammonia and amines of the formula $HNR^cR^d$, different therefrom, in which the radicals $R^c$ and $R^d$ are selected from hydrogen, and $C_1$- to $C_{20}$-alkyl, $C_3$- to $C_8$-cycloalkyl and $C_1$- to $C_{20}$-alkoxy radicals. In this connection, the alkyl and alkoxy groups can be interrupted by 1 to 10 nonadjacent heteroatoms, preferably selected from N and O, depending on their chain length, where the N heteroatoms can in turn in each case carry a substituent, preferably selected from $C_1$-$C_6$-alkyl, $C_3$-$C_8$-cycloalkyl, $C_6$-$C_{14}$-aryl and heteroaryl. Furthermore, $R^c$ and $R^d$, together with the nitrogen atom to which they are bonded, can form a 5-, 6- or 7-membered cycle which can have one or two further heteroatoms selected from N and O and/or can be substituted by one, two or three $C_1$- to $C_6$-alkyl radicals. Furthermore, $R^c$ and $R^d$ can also be aryl and heteroaryl radicals. Aryl and heteroaryl radicals optionally have one to three substituents selected e.g. from hydroxy and the aforementioned alkyl, cycloalkyl or alkoxy radicals and polyisobutene radicals.

Suitable radicals $R^c$, $R^d$ are for example hydrogen, methyl, ethyl, n-propyl, isopropyl, n-butyl, isobutyl, sec-butyl, tert-butyl, n-pentyl and n-hexyl, cyclopentyl, cyclohexyl, phenyl, tolyl, xylyl, naphthyl, tetrahydrofuranyl, tetrahydropyranyl, dioxanyl, pyrrolidyl, piperidyl, pyridyl and pyrimidyl.

Suitable compounds of the formula $HNR^cR^d$ which have exclusively one primary amino function are for example methylamine, ethylamine, n-propylamine, isopropylamine, n-butylamine, isobutylamine, sec-butylamine, tert-butylamine, pentylamine, hexylamine, cyclopentylamine, cyclohexylamine, aniline and benzylamine.

Suitable compounds of the formula $HNR^cR^d$ which have exclusively one primary amino function and in which the radical $R^c$ or $R^d$ is alkyl radicals interrupted and/or substituted by the heteroatom O are for example
$CH_3$—O—$C_2H_4$—$NH_2$, $C_2H_5$—O—$C_2H_4$—$NH_2$, $CH_3$—O—$C_3H_6$—$NH_2$, $C_2H_5$—O—$C_3H_6$—$NH_2$, n-$C_4H_9$—O—$C_4H_8$—$NH_2$, HO—$C_2H_4$—$NH_2$, HO—$C_3H_7$—$NH_2$ and HO—$C_4H_6$—NH2.

Suitable compounds of the formula $HNR^cR^d$ which have exclusively one secondary amino function are for example dimethylamine, diethylamine, methylethylamine, di-n-propylamine, diisopropylamine, diisobutylamine, di-sec-butylamine, di-tert-butylamine, dipentylamine, dihexylamine, dicyclopentylamine, dicyclohexylamine and diphenylamine.

Suitable compounds of the formula $HNR^cR^d$ which have exclusively one secondary amino function and in which the radical $R^c$ and $R^d$ is alkyl radicals interrupted and/or substituted by the heteroatom O are for example
($CH_3$—O—$C_2H_4$)$_2$NH, ($C_2H_5$—O—$C_2H_4$)$_2$NH, ($CH_3$—O—$C_3H_6$)$_2$NH, ($C_2H_5$—O—$C_3H_6$)$_2$NH, (n-$C_4H_9$—O—$C_4H_8$)$_2$NH, (HO—$C_2H_4$)$_2$NH, (HO—$C_3H_7$)$_2$NH and (HO—$C_4H_8$)$_2$NH.

Suitable compounds of the formula $HNR^cR^d$, in which $R^c$ and $R^d$, together with the nitrogen atom to which they are bonded, form a 5-, 6- or 7-membered cycle which can have one or two heteroatoms selected from N and O and can be substituted with one, two or three $C_1$- to $C_6$-alkyl radicals, are for example pyrrolidine, piperidine, morpholine and piperazine, and substituted derivatives thereof, such as N—$C_1$- to $C_6$-alkylpiperazines and dimethylmorpholine.

Suitable compounds of the formula $HNR^cR^d$ which have alkyl radicals interrupted and/or substituted by N are alkylenediamines, dialkylenetriamines, trialkylenetetramines and polyalkylenepolyamines different therefrom. These include oligo- or polyalkyleneimines, in particular oligo- or polyethyleneimines. Preferred oligoethyleneimines, consisting of 2 to 20, particularly preferably 2 to 10 and in particular 2 to 3 ethyleneimine units. Of suitability in particular are ethylenediamine, n-propylenediamine, 1,4-butanediamine, 1,6-hexanediamine, diethylenetriamine and triethylenetetramine, and also alkylation products thereof which also have at least one primary or secondary amino function, e.g. 3-(dimethylamino)-n-propylamine, N,N-dimethylethylenediamine, N,N-diethylethylenediamine and N,N,N',N'-tetramethyldiethylenetriamine.

Further suitable compounds of the formula $HNR^cR^d$ are the reaction products of alkylene oxides, in particular ethylene oxide, with primary amines, and also copolymers of ethylene oxide with ethyleneimine and/or primary or secondary $C_1$- to $C_6$-alkylamines.

Particularly suitable polyisobutenes having at least one nitrogen-containing end group used for the preparation of compounds H1) having at least one polyisobutenyl group as hydrophobic group are the reaction products of polyisobutenylsuccinic anhydrides (PIBSAs) with ammonia or in particular amines. Polyisobutenylsuccinic anhydrides can be prepared by reacting high-reactivity polyisobutenes with maleic anhydride. This reaction in the sense of an ene reaction, and the further reaction of the products obtained in this way with amines is already described in DE 27 02 604 A1. A current overview can be found in WO 2008/132083. Among these PIBSA reaction products particular preference is given to polyisobutenylsuccinimides (PIBSIs) of the formula (A)

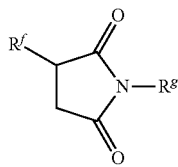

(A)

in which
$R^f$ is a polyisobutenyl radical, and
$R^g$ is hydrocarbon radical which has a terminal amino group.
PIBSIs are obtained by reacting PIBSAs with ammonia or primary amines $H_2NR^g$ (in particular di- or polyamines).
$R^g$ preferably has one of the meanings stated above for the radicals $R^c$ and $R^d$ in the amines of the formula $HNR^cR^d$.
Reference is hereby made thereto in its entirety.
Preferably, $R^g$ is hydrogen or a hydrocarbon radical which has a terminal amino group and may be aliphatic or aromatic.
Particularly preferably, $R^g$ is an aliphatic carbon radical having 1 to 60 carbon atoms, in particular 2 to 30 carbon atoms and especially 2 to 16 carbon atoms.
Examples of particularly suitable radicals $R^g$ are straight-chain or branched ω-aminoalkylene radicals, such as ω-aminomethylene, ω-aminoethylene, ω-aminopropylene, ω-aminobutylene, ω-aminopentylene and ω-aminohexylene.

Furthermore, $R^g$ is preferably an aminoalkylene radical in which the alkylene chain is interrupted by one or more amino groups of the formula $NR^h$, where the radicals $R^h$, independently of one another, are hydrogen or $C_1$-$C_6$-alkyl. $R^h$ is particularly preferably hydrogen. Such radicals $R^g$ have e.g. the following structure:

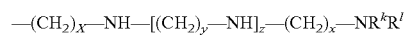

where x and y, independently of one another, are 1 to 6, preferably 2 to 4, particularly preferably 2 or 3, and z is 0 to 8, and $R^k$ and $R^l$, independently of one another, are hydrogen or $C_1$-$C_6$-alkyl. In particular, $R^k$ and $R^l$ are hydrogen or methyl and especially hydrogen.

Particularly preferred radicals $R^g$ are derived from polyalkylenepolyamines, in particular polyethylenepolyamines and polyethyleneimines. Particularly suitable radicals $R^g$ are derived from the following amines: diethylenetriamine, triethylenetetramine and pentaethylenetetramine.

One example of a very particularly preferred radical $R^g$ is

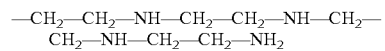

The radicals $R^g$ can also comprise further functional groups, in particular hydroxy and/or ether groups. However, they are preferably functionalized only by amino groups.

It is of course also possible to use mixtures of different polyisobutylenesuccinimides of the general formula (A) or mixtures of the polyisobutylenesuccinimides (A) with further nitrogen-containing polyisobutylene derivatives different therefrom as component for the preparation of (H1).

Further suitable reaction products of PIBSAs with amines are preferably selected from compounds of the formulae (B), (C) and (D) and mixtures thereof

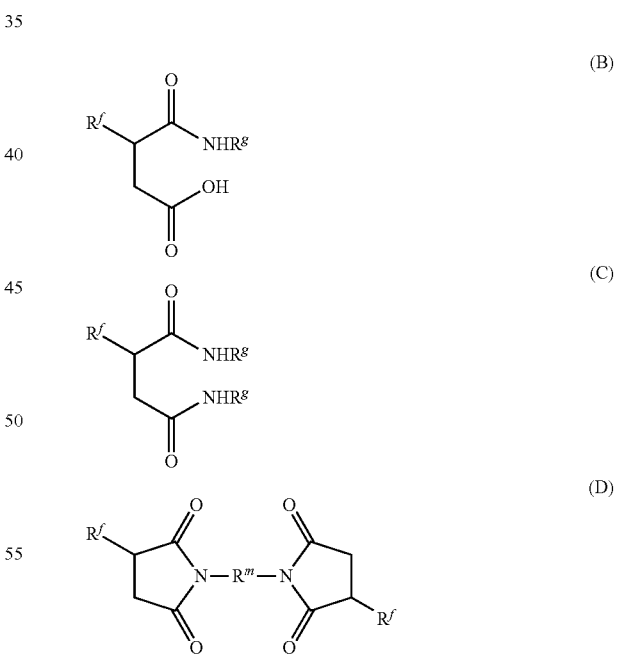

in which
$R^f$ is a polyisobutenyl radical, and
$R^m$ is hydrocarbon radical.
The compounds of the formulae (B), (C) and (D) can be prepared in a targeted manner by varying the reaction conditions or be present as by-products in compositions of the polyisobutylenesuccinimides (A).

Polyisobutylenesuccinamidic acids of the formula (B) result as intermediates in the equimolar reaction of PIBSAs with primary amines to give the polyisobutylenesuccinimides (A).

Polyisobutylenesuccinamides of the formula (C) are formed as main products in the reaction of PIBSAs with a molar excess of amine. Preferably, the quantitative molar ratio of PIBSAs to amine during the preparation of compounds (C) is about 1:2.

In the disuccinimides of the formula (D), $R^m$ is a radical derived from $R^g$ which is incorporated into the second succinimide ring via an amino group.

In a third embodiment, for the preparation of compounds H1) having at least one polyisobutenyl group as hydrophobic group, at least one polyisobutene is used which is selected from polyisobutenyl alcohols, polyisobutenyl aldehydes and mixtures thereof.

According to this third embodiment, the preparation of compounds H1) with polyisobutenyl groups preferably proceeds from polyisobutenes which are selected from products obtained by hydroformylation of polyisobutenes. Preference is given to using high-reactivity polyisobutenes for the hydroformylation. The oxo product which is formed during the hydroformylation comprises polyisobutenyl aldehydes and/or polyisobutenyl alcohols. Polyisobutenyl aldehydes and polyisobutenyl aldehyde-containing mixtures can be converted to polyisobutenyl alcohols by hydrogenation according to known processes. The hydroformylation and hydrogenation of high-reactivity polyisobutenes is described e.g. in EP-A-244 616, to which reference is made here in its entirety. Products with a high content of polyisobutenyl alcohols can also be attained by reductive hydroformylation, as is described e.g. in EP-A-277 345. Polyisobutenyl alcohols obtained by hydroformylation have, as a result of the reaction, one $CH_2$ group more than the starting polyisobutenes. They can be represented by the formula $R$—$CH_2$—OH, in which R is a polyisobutenyl radical. To prepare polyisobutenyl alcohols of the formula R—OH, in which R is a polyisobutenyl radical, the starting materials are e.g. polyisobutenes with double bonds which are located predominantly further inside the polymer chain (for example in the β or γ position). These are then converted to the polyisobutene alcohols by ozonolysis and subsequent reduction or by epoxidation and subsequent reduction or by hydroboration and subsequent hydrolysis or by halogenation with chlorine or bromine and subsequent alkaline hydrolysis. The latter-mentioned processes are described in WO 00/50543.

In a fourth embodiment, for the preparation of compounds H1) having at least one polyisobutenyl group as hydrophobic group, at least one polyisobutene is used which is selected from polyisobutenes having at least one carboxylic acid end group or a derivative thereof. Suitable derivatives are e.g. carboxylic acid anhydrides, carboxylic acid esters, carboxamides, carboximides and carboxylic acid salts.

The preparation of polyisobutenes having carboxylic acid groups and/or carboxylic anhydride groups can be prepared, as described previously, by reacting high-reactivity polyisobutenes with maleic anhydride. This reaction in the sense of an ene reaction for the preparation of polyisobutenylsuccinic anhydrides (PIBSAs) is described in DE 27 02 604 A1 and WO 2008/132083.

PIBSAs are commercially available, e.g. from BASF SE under the name Glissopal® SA. Derivatives are also suitable for the preparation of compounds H1) having at least one polyisobutenyl group as hydrophobic group. Alcohols suitable for the reaction with the PIBSAs are for example di- and polyols having preferably 2 to 5 hydroxyl groups, e.g. ethylene glycol, glycerol, diglycerol, triglycerol, trimethylolpropane, pentaerythritol. Amino alcohols suitable for the reaction with the PIBSAs are for example alkanolamines such as ethanolamine and 3-aminopropanol.

The molar ratio of PIBSAs to the specified amines, alcohols or amino alcohols during the reaction is generally in the range from 0.4:1 to 4:1, preferably 0.5:1 to 3:1. In the case of compounds with only one primary or secondary amino group, at least equimolar amounts of amine will often be used.

To introduce a hydrophilic group and provide compounds H1), the aforementioned PIBSA derivatives can be subjected to an ethoxylation and/or propoxylation. Preference is given to ethoxylated and/or propoxylated derivatives of the reaction products of PIBSAs with the specified diols, polyols, amines and amino alcohols.

In one specific embodiment, the preparation of compounds H1) with polyisobutenyl groups starts from polyisobutenes which have at least one group reactive towards isocyanate groups.

Furthermore, polytetrahydrofuran groups are suitable as hydrophobic group in the compounds H1), specifically as hydrophobic group A in the compounds of the general formulae (I), (II) or (III). Preference is given to polytetrahydrofuran groups with a number-average molecular weight in the range from about 300 to 10 000, particularly preferably about 400 to 5000.

The preparation of compounds H1) with polytetrahydrofuran groups preferably proceeds from polytetrahydrofurandiols. Suitable polytetrahydrofurandiols can be prepared by cationic polymerization of tetrahydrofuran in the presence of acidic catalysts, such as e.g. sulfuric acid or fluorosulfuric acid. Preparation processes of this type are known to the person skilled in the art.

In one specific embodiment, the preparation of compounds H1) having polytetrahydrofuran groups proceeds from polytetrahydrofurans which have at least one group reactive towards isocyanate groups.

Furthermore, polyester groups are suitable as hydrophobic group in the compounds H1), specifically as hydrophobic group A in the compounds of the general formulae (I), (II) or (III). Preference is given to polyester groups with a number-average molecular weight in the range from about 300 to 10 000, preferably 400 to 5000.

The preparation of compounds H1) having polyester groups preferably proceeds from polyesterdiols. Preference is given to polyesterdiols based on aromatic dicarboxylic acids, aliphatic dicarboxylic acids, cycloaliphatic dicarboxylic acids, and mixtures thereof. The dicarboxylic acids are preferably selected from terephthalic acid, isophthalic acid, phthalic acid, Na or K sulfoisophthalic acid, adipic acid, succinic acid, 1,2-, 1,3- or 1,4-cyclohexanedicarboxylic acid and mixtures thereof. Suitable diols are in particular aliphatic diols, such as ethylene glycol, propylene glycol, 1,6-hexanediol, neopentyl glycol, diethylene glycol, polyethylene glycols, polypropylene glycols, 1,4-dimethylolcyclohexane, and mixtures thereof.

Preference is given to polyesterdiols based on at least one aromatic dicarboxylic acid, at least one aliphatic dicarboxylic acid and at least one aliphatic diol. These include in particular those in which the aromatic dicarboxylic acid constitutes 10 to 95 mol %, in particular 40 to 90 mol %, of the total dicarboxylic acid fraction (remainder aliphatic dicarboxylic acids).

Particularly preferred polyesterdiols are the reaction products of phthalic acid/diethylene glycol, isophthalic acid/1,4-butanediol, isophthalic acid/adipic acid/1,6-hexanediol, 5-$NaSO_3$-isophthalic acid/phthalic acid/adipic acid/1,6-hexanediol, adipic acid/ethylene glycol, isophthalic acid/adipic acid/neopentyl glycol, isophthalic acid/adipic acid/neopentyl glycol/diethylene glycol/dimethylolcyclohexane and 5-NaSO₃-isophthalic acid/isophthalic acid/adipic acid/neopentyl glycol/diethylene glycol/dimethylolcyclohexane, isophthalic acid/adipic acid, neopentyl glycol/dimethylolcyclohexane.

Preference is also given to polyesterdiols based on linear or branched, $C_8$-$C_{30}$-di- or polycarboxylic acids and $C_8$-$C_{30}$-hydroxycarboxylic acids. Preferred carboxylic acids and hydroxycarboxylic acids are e.g. azelaic acid, dodecanedioic acid, suberic acid, pimelic acid, sebacic acid, tetradecanedioic acid, citric acid, ricinoleic acid, hydroxystearic acid and mixtures thereof. The diol component used for the preparation of these polyesterdiols is preferably 1,4-butanediol, 1,5-pentanediol, 1,6-hexanediol, neopentyl glycol, 1,4-dimethylolcyclohexane, diethylene glycol and mixtures thereof.

In a specific embodiment, the preparation of compounds H1) having polyester groups proceeds from polyesters which have at least one group reactive towards isocyanate groups.

Furthermore, silicone groups are suitable as hydrophobic group in the compounds H1), specifically as hydrophobic group A in the compounds of the general formulae (I), (II) or (III).

Preferred silicone groups are polysiloxane groups with a number-average molecular weight in the range from about 300 to 50 000, particularly preferably 400 to 30 000.

In a specific embodiment, the preparation of compounds H1) having silicone groups proceeds from polysiloxanes which have at least one group reactive towards isocyanate groups.

To insert a hydrophilic group and provide compounds H1), the aforementioned silicone compounds can be subjected to a reaction for introducing at least one polyether group. Preferably, the ether groups are selected from polyethylene oxide groups, polypropylene oxide groups and poly(ethylene oxide/propylene oxide) groups.

Suitable silicone compounds H1) and for the preparation of silicone compounds H1) are the compounds known under the INCI names Dimethicone Copolyols or Silicone Surfactants, such as, for example, the compounds available under the trade names Abil® (Th. Goldschmidt), Alkasil® (Rhône-Poulenc), Silicone Polyol Copolymer® (Genesee), Belsil® (Wacker), Silwet® (OSI) or Dow Corning (Dow Corning). These include compounds with the CAS numbers 64365-23-7; 68937-54-2; 68938-54-5; 68937-55-3. A suitable commercially available compound is Belsil® DMC 6031.

On account of their silicone groups, the compounds (E), (G), (J) and (K) listed below are preferably suitable for introducing hydrophobic groups (specifically groups A)) during the preparation of the compounds H1). If the compounds (E), (G), (J) and (K) listed below also already have at least one hydrophilic group (especially groups B)), they can also be used as such (i.e. without further reaction) as component H1). This applies especially to the compounds (E), (G), (J) and (K) which have at least one group (F) with alkylene oxide repeat units.

Preferred silicone compounds H1) and compounds for the preparation of silicone compounds H1) are polysiloxanes of the general formula (E)

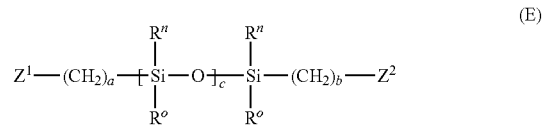

in which
a and b, independently of one another, are 1 to 8,
c is 2 to 1000,
$R^n$ and $R^o$, independently of one another, are alkyl, cycloalkyl, aryl or arylalkyl,
$Z^1$ and $Z^2$, independently of one another, are radicals of the formula (F)

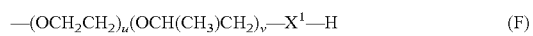

where
in the formula (F), the order of the alkylene oxide units is arbitrary,
u and v, independently of one another, are an integer from 0 to 500, where the sum of u and v is >0,
$X^1$ is O or $NR^p$, in which $R^p$ is hydrogen, alkyl, cycloalkyl or aryl.

Preferably, in the formula (E), the sum of u and v is selected such that the molecular weight of the polysiloxanes H1) is in a range from about 300 to 30 000.

Preferably, the total number of alkylene oxide units in the polysiloxanes H1), i.e. the sum of u and v, is in a range from about 3 to 200, preferably 5 to 180.

Preferably, in the compounds of the formula (E), the radicals $R^n$ and $R^o$, independently of one another, are selected from methyl, ethyl, cyclohexyl, phenyl and benzyl. Particularly preferably, $R^n$ and $R^o$ are both methyl.

One example of suitable compounds of formula (E) are the bis(polyethylene glycol) dimethicones of the general formula (E.1)

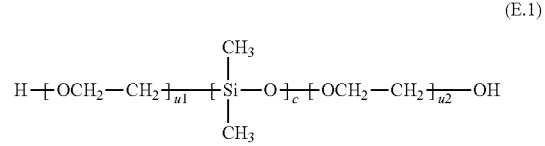

in which
c is an integer from 3 to 500, preferably 5 to 250, and
u1 and u2, independently of one another, are 2 to 500, in particular 3 to 250, specifically 5 to 100.

Preferred silicone compounds H1) and compounds for the preparation of silicone compounds H1) are also selected from polysiloxanes of the general formula (G)

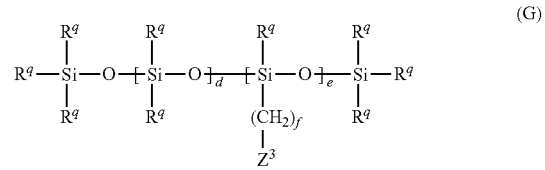

in which
the order of the siloxane units is arbitrary,
the radicals $R^q$ are in each case independently of one another alkyl, cycloalkyl or aryl,
d is an integer from 2 to 1000, e is an integer from 2 to 100,
f is an integer from 2 to 8, and
$Z^3$ is OH, $NHR^r$ or a radical of the formula (F), as defined above,
where $R^r$ is hydrogen, $C_1$-$C_8$-alkyl, $C_5$-$C_8$-cycloalkyl or a radical of the formula —$(CH_2)_w$—$NH_2$, where w is an integer from 1 to 10, preferably 2 to 6,
and mixtures thereof.

One example of suitable compounds of the formula (G) are the ethoxylated and/or propoxylated polydimethylsiloxanes of the general formula (G.1)

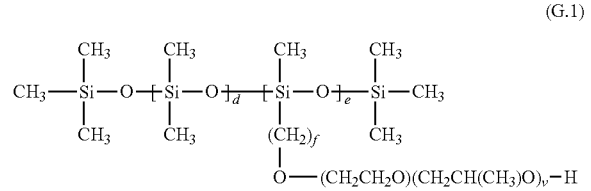

(G.1)

in which
the order of the siloxane units is arbitrary,
d is an integer from 2 to 1000, preferably 3 to 500, in particular 5 to 100,
e is an integer from 2 to 100, preferably 3 to 50, in particular 4 to 20,
f is an integer from 2 to 8, and
u and v, independently of one another, are an integer from 0 to 500, preferably 0 to 250, where the sum of u and v is ≥1, preferably ≥5, in particular ≥10.

Suitable compounds of the formula G.1 are available under the name Wacker-Belsil® DMC 6031 and Pluriol® ST 4005 (BASF SE).

Preferred silicone compounds H1) and compounds for the preparation of silicone compounds H1) are also polysiloxanes with repeating units of the general formula (J)

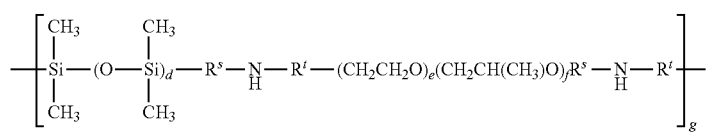

(J)

in which
d is an integer from 0 to 100,
g is an integer from 1 to 8,
$R^s$ and $R^t$, independently of one another, are $C_1$- to $C_8$-alkylene,
the order of the alkylene oxide units is arbitrary and e and f, independently of one another, are an integer from 0 to 200, where the sum of r and s is >0.

Preferably, in the formula (J), $R^s$ and $R^t$, independently of one another, are a $C_2$- to $C_4$-alkylene radical.

In particular, $R^s$ and $R^t$, independently of one another, are a $C_2$- to $C_3$-alkylene radical.

Preferably, the molecular weight of the compound of the formula (J) is in a range from about 300 to 100 000.

Preferably, in the formula 1.3, d is an integer from 1 to 20, such as e.g. 2 to 10.

Preferably, the total number of the alkylene oxide units of the compound of the formula (J), i.e. the sum of e and f, is in a range from about 3 to 200, preferably 5 to 180.

Preferably, the end groups of the polysiloxanes with repeat units of the general formula (J) are selected from $(CH_3)_3SiO$, h, $C_1$-$C_8$-alkyl and mixtures thereof. A preferred alkyl end group is methyl.

Amino-group-containing compounds with repeat units of the general formula (J) preferably have an amine number in a range from about 2 to 50, in particular 3 to 20.

Suitable alkoxylated siloxane amines of the formula 1.3 are described e.g. in WO-A-97/32917, to which reference is made here in its entirety. Commercially available compounds are e.g. the Silsoft grades from Momentive Performance Materials (formerly Witco), e.g. Silsoft A-843.

Preferred silicone compounds H1) and compounds for the preparation of silicone compounds H1) are also polysiloxanes with repeating units of the general formula (K)

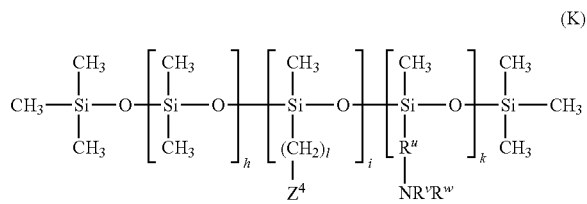

(K)

in which
$R^u$ is a $C_1$- to $C_8$-alkylene radical,
$R^v$ and $R^w$, independently of one another, are hydrogen, $C_1$-$C_8$-alkyl or $C_5$-$C_8$-cycloalkyl,
the order of the siloxane units is arbitrary,
h, i and k, independently of one another, are 0 to 100, where the sum of h, i and k is at least 3,
l is an integer from 2 to 8,
$Z^4$ is a radical of the formula (F.1)

—$(OCH_2CH_2)_u(OCH(CH_3)CH_2)_v$—$OR^x$ (F.1)

where
in the formula (F.1) the order of the alkylene oxide units is arbitrary,
u and v, independently of one another, are an integer from 0 to 500, where the sum of u and v is >0,
$R^x$ is hydrogen or a $C_1$-$C_8$-alkyl radical,
and mixtures thereof.

Preferably, in the formula (K), the radical $R^u$ is a $C_2$- to $C_4$-alkylene radical.

Preferably, in the formula (K), $R^v$ and $R^w$, independently of one another, are hydrogen or $C_1$- to $C_4$-alkyl.

Preferably, the sum of h, I and k is selected such that the molecular weight of the compound of the formula (K) is in a range from about 300 to 100 000, preferably 500 to 50 000.

Preferably, the total number of the alkylene oxide units in the radical of the formula (F.1), i.e. the sum of u and v, is in a range from about 3 to 200, preferably 5 to 80.

Preferably, in the formula (F.1), the radical $R^x$ is hydrogen or $C_1$- to $C_4$-alkyl.

A suitable compound of the formula (K) is e.g. Silsoft A-858 from Momentive Performance Materials (formerly Witco).

A further preferred silicone compound H1) and compound suitable for the preparation of silicone compounds H1) is the compound with the INCI name Methoxy PEG/PPG-7/3 Aminopropyl Dimethicone. This is commercially available under the name ABIL® Soft AF 100 from Evonik Industries.

Suitable polysiloxane diamines for the preparation of silicone compounds H1) are Tegomer® A-Si 2122 (Mn=900 g/mol) and Tegomer® A-Si 2322 (Mn=2800 g/mol) from Evonik Industries (formerly Th. Goldschmidt).

Hydrophilic Group of H1)

Preferably, in the compounds H1), the hydrophilic group is selected from
polyethylene oxide-containing groups,
polypropylene oxide-containing groups,
poly(ethylene oxide/propylene oxide)-containing groups,
polyethyleneimine-containing groups,
polysorbate-containing groups,
polyglycerol-containing groups,
polyvinylpyrrolidone-containing groups,
and combinations thereof.

Specifically, the hydrophobic group B in the compounds of the general formulae (I), (II) or (III) is selected from
polyethylene oxide-containing groups,
polypropylene oxide-containing groups,
poly(ethylene oxide/propylene oxide)-containing groups,
polyethyleneimine-containing groups,
polysorbate-containing groups,
polyglycerol-containing groups,
polyvinylpyrrolidone-containing groups,
and combinations thereof.

Suitable hydrophilic groups in the compounds H1), specifically as hydrophilic groups A in the compounds of the general formulae (I), (II) or (III) are preferably polyether-containing groups, more specifically polyethylene oxide-containing groups (=polyethylene glycol-containing groups), polypropylene oxide-containing groups (=polypropylene glycol-containing groups) and copolymers, the repeat units of which are derived from polyethylene oxide and polypropylene oxide. Preference is given to polyether-containing groups with a number-average molecular weight in the range from about 300 to 10 000, preferably 400 to 5000. Poly(ethylene oxide/propylene oxide)-containing groups can comprise, in copolymerized form, the ethylene oxide units and the propylene oxide units in random distribution or in the form of blocks.

The preparation of compounds H1) with polyether groups preferably proceeds from polyetherdiols or polyether monoalcohols. Preferred polyether monoalcohols are the polyalkylene glycol monoalkyl ethers. Preferred polyalkylene glycol monoalkyl ethers are polyalkylene glycol monomethyl ethers and polyalkylene glycol monoethyl ethers. Particular preference is given to polyethylene glycol monomethyl ethers.

For the preparation of compounds H1), polyethylene glycol monomethyl ethers are preferred. Suitable polyethylene glycol monomethyl ethers are the Pluriol® A . . . E grades from BASF SE (molecular weight in brackets), specifically Pluriol A 350 E (350 g/mol), Pluriol A 500 E (500 g/mol), Pluriol A 750 E (750 g/mol), Pluriol A 760 E (750 g/mol), Pluriol A 1000 E (1000 g/mol), Pluriol A 1020 E* (1000 g/mol), Pluriol A 2000 E (2000 g/mol), Pluriol A 3010 E* (3000 g/mol) and Pluriol A 5010 E* (5000 g/mol).

For the preparation of compounds H1), polyetherdiols in the form of polyethylene oxide diols (polyethylene glycols) are preferred. They are commercially available as the Pluriol® E grades from BASF SE. These include:
Pluriol E 200, 300, 400, 600, 1000, 1500, 3400, 4000, 6000, 8000, 9000 and 12000.

Polyetherdiols in the form of EO/PO/EO triblock copolymers are suitable for the preparation of compounds H1). They are commercially available as the Pluronic® PE grades from BASF SE. These include:
(Name/EO Content in %/Molecular Weight)
Pluronic PE 3100/ca. 10/ca. 1000
Pluronic PE 3500/ca. 50/ca. 1900
Pluronic PE 4300/ca. 30/ca. 1750
Pluronic PE 6100/ca. 10/ca. 2000
Pluronic PE 6120/ca. 12/ca. 2100
Pluronic PE 6200/ca. 20/ca. 2450
Pluronic PE 6400/ca. 40/ca. 2900
Pluronic PE 6800/ca. 80/ca. 8000
Pluronic PE 7400/ca. 40/ca. 3500
Pluronic PE 8100/ca. 10/ca. 2600
Pluronic PE 9200/ca. 20/ca. 3650
Pluronic PE 9400/ca. 40/ca. 4600
Pluronic PE 10100/ca. 10/ca. 3500
Pluronic PE 10300/ca. 30/ca. 4950
Pluronic PE 10400/ca. 40/ca. 5900
Pluronic PE 10500/ca. 50/ca. 6500

For the preparation of compounds H1), polyetherdiols in the form of PO/EO/PO triblock copolymers are suitable. They are commercially available as the Pluronic® RPE grades from BASF SE. These include:
(Name/EO Content in %/Molecular Weight)
Pluronic RPE 1720/ca. 20/ca. 2150
Pluronic RPE 1740/ca. 40/ca. 2650
Pluronic RPE 2035/ca. 35/ca. 4100
Pluronic RPE 2520/ca. 20/ca. 3100
Pluronic RPE 2525/ca. 25/ca. 2000
Pluronic RPE 3110/ca. 10/ca. 3500

For the preparation of compounds H1), polyethers which have one or two terminal amino groups are also suitable as hydrophilic group. These can be prepared by amination of the aforementioned polyethylene oxide-containing groups, polypropylene oxide-containing groups and poly(ethylene oxide/propylene oxide)-containing groups with ammonia.

Also suitable as hydrophilic group for the preparation of compounds H1) are polyethyleneimine-containing groups. These preferably have a number-average molecular weight in the range from about 300 to 10 000, preferably 400 to 5000.

Also suitable as hydrophilic group for the preparation of compounds H1) are polysorbate-containing groups. Polysorbates are obtained by esterification of sorbitol with a fatty acid and subsequent ethoxylation. The products are commercially available, e.g. under the name Tween.

Also suitable as hydrophilic group for the preparation of compounds H1) are polyglycerol-containing groups. Polyglycerol mixtures can be prepared by alkali-catalyzed condensation of glycerol at elevated temperatures (Fette, Seifen, Anstrichmittel, 88th volume, No. 3, 1986, pp. 101-106 (4)) or by reacting glycerol with epichlorohydrin in the presence of an acidic catalyst at elevated temperatures (DE-A 38 42 692).

A typical suitable polyglycerol mixture has the following composition:
0 to 5% by weight of glycerol,
20 to 40% by weight of diglycerol,
35 to 55% by weight of triglycerol,
10 to 20% by weight of tetraglycerol,
5 to 10% by weight of pentaglycerol,
1 to 5% by weight of hexaglycerol and
0 to 5% by weight of higher polyglycerols.

The preparation of compounds H1) preferably takes place starting from polyglycerols by esterification with at least one compound which has at least one carboxylic acid group or a derivative thereof capable of esterification and at least one hydrophobic group. These include e.g. fatty acids and fatty acid mixtures. These include preferably polyisobutenes with at least one carboxylic acid end group or a derivative thereof.

The polyglycerol esters are prepared by esterification reaction between the corresponding polyglycerol mixtures and the desired carboxylic acid or carboxylic acid mixture or a derivative thereof by customary methods. Suitable derivatives are the anhydrides, halides and esters with $C_1$-$C_4$-alkanols. Usually, the esterification takes place in the presence of an acidic or basic esterification catalyst such as hypophosphorus acid, phosphorus acid, sulfuric acid, p-toluenesulfonic acid, citric acid, sodium methylate, tin oxide or a soap.

Polyglycerols and polyglycerol esters and their preparation are described in DE 40 23 593 A1, to which reference is hereby made.

The preparation of compounds H1) with polyvinylpyrrolidone groups preferably proceeds from polyvinylpyrrolidone homopolymers and copolymers which comprise N-vinylpyrrolidone and a further ethylenically unsaturated monomer different therefrom in copolymerized form. Suitable N-vinylpyrrolidone copolymers are quite generally neutral, anionic, cationic and amphoteric polymers.

Preferred N-vinylpyrrolidone copolymers are selected from copolymers of N-vinylpyrrolidone and vinyl acetate, copolymers of N-vinylpyrrolidone and vinyl propionate, copolymers of N-vinylpyrrolidone, vinyl acetate and vinyl propionate, copolymers of N-vinylpyrrolidone and vinyl acrylate, copolymers of N-vinylpyrrolidone, ethyl methacrylate and methacrylic acid, copolymers of N-vinylpyrrolidone and N-vinylimidazole and derivatives thereof obtained by protonation and/or quaternization, copolymers of N-vinylpyrrolidone and dimethylaminoethyl methacrylate and derivatives thereof obtained by protonation and/or quaternization, copolymers of N-vinylpyrrolidone, N-vinylcaprolactam and N-vinylimidazole and derivatives thereof obtained by protonation and/or quaternization.

In a specific embodiment, the preparation of compounds H1) with polyvinylpyrrolidone groups proceeds from polyvinylpyrrolidone homopolymers and polyvinylpyrrolidone copolymers which in each case have at least one group reactive towards isocyanate groups.

Linker X

Preferably, the compounds H1) have at least one bridging group X) which joins at least one hydrophobic group and at least one hydrophilic group together.

Very generally, the bridging group X) is selected from a chemical bond or a divalent or polyvalent radical to which at least one hydrophilic group and at least one hydrophobic group are bonded.

Preferably, the compound H1 is selected from compounds of the general formulae (I), (II) or (III), as defined above. The group X is then preferably selected from groups of the formulae:

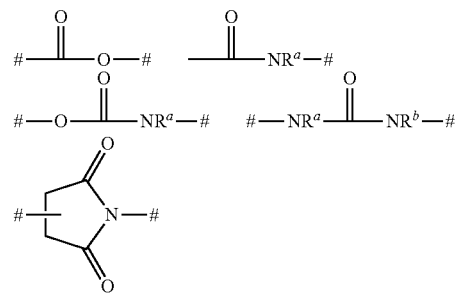

where # in each group X stands once for a binding site to a group A and once for a binding site to a group B, $R^a$ and $R^b$, independently of one another, are hydrogen, alkyl, cycloalkyl, heterocycloalkyl, aryl or hetaryl.

The compound with a block structure H1) is particularly preferably selected from polyisobutenyl alcohol alkoxylates, polyisobutenyl amine alkoxylates, reaction products of at least one polyisobutene with at least one carboxylic acid end group or a derivative thereof and at least one polyalkylene oxide with a terminal group reactive towards anhydride groups, silicone compounds which have at least one polyether group, reaction products of at least one compound which comprises at least one hydrophobic group and at least one group reactive towards isocyanate groups, at least one compound which comprises at least one hydrophilic group and at least one group reactive towards isocyanate groups, and at least one polyisocyanate.

Urethane Compound H1)

Urethane compounds H1) are a preferred embodiment.

Preference is given to a urethane compound H1) which comprises, in incorporated form, p1) at least one compound which comprises at least one hydrophobic group and at least one group reactive towards isocyanate groups, p2) at least one compound which comprises at least one hydrophilic group and at least one group reactive towards isocyanate groups, and p3) at least one polyisocyanate.

As regards compounds having at least one hydrophobic group p1) and compounds having at least one hydrophilic group p2) preferred and suitable for the preparation of urethane compounds H1), reference is made to the previous statements relating to hydrophobic and hydrophilic groups (specifically groups A) and B)) and to compounds which have these groups, in their entirety.

Suitable polyisocyanates p3) are selected from compounds having 2 to 5 isocyanate groups, isocyanate prepolymers with an average number of from 2 to 5 isocyanate groups, and mixtures thereof. These include e.g. aliphatic, cycloaliphatic and aromatic di-, tri- and polyisocyanates. Suitable diisocyanates p3) are e.g. tetramethylene diisocyanate, hexamethylene diisocyanate, 2,3,3-trimethylhexamethylene diisocyanate, 1,4-cyclohexylene diisocyanate, isophorone diisocyanate, 1,4-phenylene diisocyanate, 2,4- and 2,6-tolylene diisocyanate and isomer mixtures thereof (e.g. 80% 2,4- and 20% 2,6-isomer), 1,5-naphthylene diisocyanate, 2,4- and 4,4'-diphenylmethane diisocyanate. A suitable triisocyanate p3) is e.g. triphenylmethane 4,4',4"-triisocyanate. Also suitable are isocyanate prepolymers and polyisocyanates which are obtainable by addition of the aforementioned isocyanates onto polyfunctional hydroxyl- or amine-groups-containing compounds. Polyisocyanates which are formed by biuret, allophanate or isocyanurate formation are also suitable.

Preferably, the polyisocyanate component p3) comprises at least one diisocyanate having two differently reactive isocyanate groups. The polyisocyanate component p3) then particularly preferably comprises isophorone diisocyanate and its biurets, allophanates and/or isocyanurates. Furthermore, the polyisocyanate component p3) preferably comprises hexamethylene diisocyanate. In particular, the polyisocyanate component p3) consists only of isophorone diisocyanate or only of hexamethylene diisocyanate or of a mixture of isophorone diisocyanate and hexamethylene diisocyanate.

In a further embodiment, the urethane compounds H1) additionally comprise at least one compound p4) in incorporated form which is preferably selected from compounds with a molecular weight in the range from 56 to 280 g/mol which comprise two groups reactive towards isocyanate groups per molecule. Suitable compounds p4) are e.g. diols, diamines, amino alcohols and mixtures thereof.

As component p4), preference is given to using diols, the molecular weight of which is in a range from about 62 to 286 g/mol. These include e.g. diols having 2 to 18 carbon atoms, preferably 2 to 10 carbon atoms, such as 1,2-ethanediol, 1,3-propanediol, 1,4-butanediol, 1,6-hexanediol, 1,5-pentanediol, 1,10-decanediol, 2-methyl-1,3-propanediol, 2,2-dimethyl-1,3-propanediol, di-, tri-, tetra-, penta- and hexaethylene glycol, neopentyl glycol, cyclohexanedimethylol and mixtures thereof. Particular preference is given to neopentyl glycol.

Preferred amino alcohols p4) are e.g. 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol, N-methyldiethanolamine, etc.

Preferred diamines p4) are e.g. ethylenediamine, propylenediamine, 1,4-diaminobutane, 1,5-diaminopentane, 1,6-diaminohexane (hexamethylenediamine), isophoronediamine and mixtures thereof.

The compounds specified as component p4) can be used individually or in mixtures. Particular preference is given to using 1,2-ethanediol, 1,4-butanediol, 1,6-hexanediol, neopentyl glycol, diethylene glycol, cyclohexanedimethylol, N-methyldiethanolamine and mixtures thereof.

In a further embodiment, the urethane compounds H1) additionally comprise, in incorporated form, at least one compound p5) which is preferably selected from compounds with a molecular weight in the range from 56 to 280 g/mol which comprise one group reactive towards isocyanate groups per molecule. Compounds of this type with one group reactive towards isocyanate groups per molecule are also referred to as stoppers. Suitable compounds p5) are e.g. monoalcohols, and also amines and amino alcohols which have only one group reactive towards NCO groups. These include methanol, ethanol, n-propanol, etc.

One specific embodiment is a urethane compound H1) which comprises, in incorporated form, p1) at least one compound which comprises at least one hydrophobic group and at least one group reactive towards isocyanate groups, selected from polyisobutenes with at least one nitrogen-containing end group, polytetrahydrofurans and mixtures thereof, p2) at least one compound which comprises at least one hydrophilic group and at least one group reactive towards isocyanate groups, selected from polyethylene oxides, polyvinylpyrrolidone and mixtures thereof, p3) hexamethylene diisocyanate and/or isophorone diisocyanate, p4) optionally at least one compound which is selected from neopentyl glycol, N-methyldiethanolamine, 1,5-diaminopentane, 1,6-diaminohexane, isophoronediamine and mixtures thereof.

The preparation of the urethane compounds H1) can take place by customary processes. Preferably, the preparation of the urethane compounds H1 takes place by a two-stage process. The reaction of the components preferably takes place here such that the resulting urethane compounds comprise at least one hydrophobic compound p1) and at least one hydrophilic compound p2) in incorporated form.

The invention also provides a process for the preparation of a urethane compound H1), which comprises, in incorporated form, p1) at least one compound which comprises at least one hydrophobic group and at least one group reactive towards isocyanate groups, p2) at least one compound which comprises at least one hydrophilic group and at least one group reactive towards isocyanate groups, and p3) at least one polyisocyanate, p4) at least one compound which is selected from compounds with a molecular weight in the range from 56 to 280 g/mol which comprise two groups reactive towards isocyanate groups per molecule, p5) at least one compound which is selected from compounds with a molecular weight in the range from 56 to 280 g/mol which comprise one group reactive towards isocyanate groups per molecule, in which i) in a first stage, the hydrophobic compounds p1), the polyisocyanates p3) and, if present, optionally at least some of the compounds p4) and/or p5) are reacted to give an isocyanate-group-containing prepolymer, and ii) in a second stage, the prepolymer obtained in i) is reacted with the hydrophilic compounds p2) and, if present, the compounds p4) and/or p5) not already used in step i).

In the first stage i), an NCO-group-containing prepolymer is firstly prepared from the hydrophobic compounds p1) and the polyisocyanates p3). If desired, in this stage, if present, the compounds of component p4) and/or stopper p5) can also be used in part or in their entirety for the preparation of the prepolymer. However, stoppers p5) are preferably used in stage ii). In each case, appropriate selection of the amount of component p3) ensures that an isocyanate-group-containing prepolymer is obtained in stage i). The ratio of NCO equivalents of component p3) to equivalents of active hydrogen atoms of components p1) and, if present, p4) and p5) is preferably in a range from about 1:1 to 3:1, particularly preferably 1.01:1 to 2.5:1, in particular 1.05:1 to 2:1.

Preferably, the reaction in both stages i) and ii) takes place under an inert gas atmosphere, such as e.g. under nitrogen. Furthermore, the reaction preferably takes place in both stages i) and ii) at ambient pressure or under increased pressure.

The reaction in stage i) is preferably to be carried out in a suitable inert solvent or solvent mixture. Suitable solvents are hydrocarbons and hydrocarbon mixtures, such as pentane, hexane, cyclohexane, decalin, ligroin, petroleum ether, etc. Also of suitability are aromatic hydrocarbons, such as benzene, toluene or xylene. Suitable solvents are also aprotic polar solvents, e.g. tetrahydrofuran, ethyl acetate, N-methylpyrrolidone, dimethylformamide and preferably ketones, such as acetone and methyl ethyl ketone.

The reaction temperature in step i) is preferably in a range from about 0 to 120° C., particularly preferably 5 to 90° C. If the components p1) and, if present, p4) and/or p5) comprise amine-group-containing compounds, then the reaction temperature is preferably in a range from about 0 to 60° C., particularly preferably from 10 to 40° C. When using amine-group-containing components, the reaction can, if desired, also take place in a solvent or solvent mixture which can have active hydrogen atoms. Besides those mentioned above, use is then preferably made of cosmetically acceptable solvents, preferably alcohols, such as ethanol and isopropanol, and also mixtures of alcohols and water.

The NCO-group-containing prepolymers obtained in step i) can if desired be subjected, prior to the further reaction in step ii), to an isolation and/or purification by customary processes known to the person skilled in the art. Preferably, the preparation of the prepolymers and the preparation of the urethane compounds H1) therefrom takes place without isolation of an intermediate.

The preparation of the urethane compound according to the invention in step ii) takes place by reacting the prepolymers obtained in step i) with the hydrophilic compounds p2) and optionally compounds of components p4) and/or p5). In this connection, the ratio of NCO equivalents of the prepolymers to equivalents of active hydrogen atoms in components p2) and if present, p4) and p5) is in a range from about 0.6:1 to 1.4:1, preferably 0.8:1 to 1.2:1, in particular 0.9:1 to 1.1:1.

The reaction takes place preferably also in the second stage ii) in one of the aforementioned solvents, preferably in a cosmetically acceptable solvent. If the bonding of component p2) takes place via amine groups, and also the optionally used compounds p4) and p5) have amine groups as NCO-reactive groups, the reaction can be carried out in alcohols and alcohol/water mixtures. Preference is given to ethanol, isopropanol, mixtures thereof and mixtures of these alcohols with water. The reaction temperature in step ii) is then preferably in a range from about 0 to 60° C., particularly preferably 10 to 40° C. If the resulting urethane compounds still have free isocyanate groups, then these are finally deactivated by adding compounds p4), p5) or water. Preferably, e.g. 2-amino-2-methyl-1-propanol is used to deactivate free isocyanate groups.

Polyisobutenyl Alcohol Alkoxylates and Polyisobutenyl Amine Alkoxylates H1)

A specific embodiment of compounds H1) is the alkoxylates of polyisobutenyl alcohols and polyisobutenyl amines with ethylene oxide and/or propylene oxide.

The degree of alkoxylation, i.e. the average chain length of the polyether chains of the alkoxylates, can be determined by means of the quantitative molar ratio of alcohol or amine to alkylene oxide. Preference is given to alcohol alkoxylates having about 1 to 1000, preferably about 2 to 500, in particular 3 to 100, alkylene oxide units. The particular degree of alkoxylation is established depending on the use amounts of alkylene oxide(s) used for the reaction and also the reaction conditions. It is usually a statistical average value since the number of alkylene oxide units in the alcohol alkoxylates resulting from the reaction varies.

One preferred embodiment is ethylene oxide homoalkoxylates or 1,2-propylene oxide homoalkoxylates. Particular preference is given to ethylene oxide homoalkoxylates.

A further type of polyisobutenyl alcohol alkoxylates or polyisobutenyl amine alkoxylates to be used is based on ethylene oxide and 1,2-propylene oxide. Here, the alkylene oxides can if desired be incorporated in a random manner. For this, the alkylene oxides can be used in the form of mixtures for the alkoxylation. Preferably, the alkylene oxide units are arranged in blocks such that at least two different alkylene oxide blocks are produced which are in each case formed from two or more units of identical alkylene oxides. If such block alkoxylates are used, it is preferred for the alkylene oxide moiety to be composed of 2 to 5, preferably 2 or 3 and in particular of 2 blocks. The block copolyethers can be obtained by reacting one of the above-described polyisobutenyl alcohols or polyisobutenyl amines with a first alkylene oxide, subsequent reaction with a second alkylene oxide different therefrom and optionally further sequential addition in each case of an alkylene oxide different from the particular alkylene oxide added beforehand, until the desired block structure is attained.

Preference is given to EO-PO coalkoxylates in which the molar ratio of EO to PO is preferably in a range from 10:1 to 1:10. Preferably, the ethylene oxide is used in the same molar amount as the propylene oxide, or ethylene oxide is used in a molar excess over propylene oxide. Preference is then given to EO-PO coalkoxylates in which the molar ratio of EO to PO is preferably in a range from 1:1 to 10:1 and in particular 1.5:1 to 5:1.

The reaction of the alcohols or amines with the alkylene oxide(s) takes place by customary processes known to the person skilled in the art and in apparatuses customary for this purpose which are equipped for working under pressure.

The alkoxylation can be catalyzed by strong bases, such as alkali metal hydroxides and alkaline earth metal hydroxides, Brönsted acids or Lewis acids, such as $AlCl_3$, $BF_3$ etc. For alcohol oxylates of narrow distribution, it is possible to use catalysts such as hydrotalcite or double metal cyanides (DMC).

The alkoxylation is carried out preferably at temperatures of about 50 to 250° C., particularly preferably from 90 to 200° C. The alkylene oxide or the mixture of different alkylene oxides is fed to the mixture of alcohol or amine used according to the invention and catalyst under the vapor pressure of the alkylene oxide mixture prevailing at the selected reaction temperature, or a higher pressure.

If desired, the alkylene oxide can be diluted with an inert gas (for example noble gases, nitrogen, $CO_2$) up to 99.9%. Especially in the case of ethylene oxide, this ensures additional safety against the gas phase decomposition of this alkylene oxide, it being possible, in this embodiment, to also use a further alkylene oxide, for example propylene oxide, as inert gas within the context of the invention.

Suitable alkoxylation conditions are also described in Nikolaus Schönfeldt, Grenzflächenaktive Äthylenoxid-Addukte [Interface-active ethylene oxide adducts], Wissenschaftliche Verlagsgesellschaft mbH, Stuttgart 1984. As a rule, the alkoxylation is carried out in the presence of the catalyst without the addition of a solvent. However, the alkoxylation can also be carried out with co-use of a solvent inert under the alkoxylation conditions.

In one suitable embodiment, the alkoxylation is catalyzed by at least one strong base. Suitable strong bases are e.g. alkali metal alcoholates, alkali metal hydroxides, alkaline earth metal oxides or alkaline earth metal hydroxides. The bases are generally used in an amount of from 0.01 to 1% by weight, based on the amount of the alcohol to be alkoxylated (cf. G. Gee et al., J. Chem. Soc. (1961), p. 1345; B. Wojtech, Makromol. Chem. 66, (1966), p. 180).

An acidic catalysis of the alkoxylation reaction is also possible. Besides Brönsted acids, Lewis acids are also suitable, such as for example $AlCl_3$, $BF_3$, $BF_3$ dietherates, $BF_3 \times H_3PO_4$, $SbCl_4 \times 2H2O$, hydrotalcite (cf. P. H. Plesch, The Chemistry of Cationic Polymerization, Pergamon Press, New York (1963)).

In a further embodiment, the alkoxylation is carried out in the presence of a double metal cyanide compound as catalyst. DMC compound which can be used are in principle all suitable compounds known to the person skilled in the art. DMC compounds suitable as catalyst are described for example in WO 99/16775 and DE-A-101 17 273.

Reaction Products H1) of PIBs Having Carboxylic Acid End Group with Polyalkylene Oxide Alcohols or Polyalkylene Oxide Amines A specific embodiment of compounds H1) is the reaction products of at least one polyisobutene having at least one carboxylic acid end group or a derivative thereof and at least one polyalkylene oxide having a terminal group reactive towards carboxylic acid groups, carboxylic acid anhydride groups or carboxylic acid groups derivatized in any other way.

As regards polyisobutenes suitable for the preparation of these reaction products H1) which have at least one carboxylic acid end group or a group obtained from esterification, amidation or imidation, reference is made to the prior disclosure relating to these polyisobutenes in its entirety. Furthermore, as regards suitable polyalkylene oxides having at least one terminal OH group or at least one terminal primary or secondary amino group, reference is made to the prior disclosure relating to these polyalkylene oxides in its entirety.

Processes for the esterification, amidation or imidation of polyisobutenes with at least one carboxylic acid end group or a derivative thereof are known in principle and described e.g. in EP 0 744 413 A2 and U.S. Pat. No. 5,137,980 referred to therein.

Preferably, a polyisobutenyl anhydride, specifically PIBSA, is used for the reaction. Furthermore, for the reaction, preference is given to using a compound with a hydrophilic group which is selected from polyethylene oxide diols, polyethylene oxide monoalcohols, polypropylene oxide diols, polypropylene oxide monoalcohols, poly(ethylene oxide/propylene oxide) diols, poly(ethylene oxide/propylene oxide) monoalcohols, polyethylene oxide diamines, polyethylene oxide monoamines, polypropylene oxide diamines, polypropylene oxide monoamines, poly(ethylene oxide/propylene oxide) diamines, poly(ethylene oxide/propylene oxide) monoamines and mixtures thereof.

Preferably, PIBSA and a polyethylene oxide monoalkyl ether is used for the reaction. Particular preference is given to using PIBSA and a polyethylene oxide monomethyl ether for the reaction. Reference is made to the preceding statements relating to suitable Pluriol® grades.

In one specific embodiment, the auxiliary H1) comprises a reaction product of PIBSA and a polyethylene oxide monomethyl ether. In a very specific embodiment, the auxiliary H1) consists of a reaction product of PIBSA and a polyethylene oxide monomethyl ether. For the preparation of this auxiliary H1), a PIBSA and a polyethylene oxide monomethyl ether are preferably used in a molar ratio of from 0.9:1 to 1:2.5, particularly preferably of about 1:1. The PIBSA preferably has a molecular weight in a range from 350 to 2500, preferably 500 to 1500. The polyethylene oxide monomethyl ether preferably has a molecular weight in a range from 350 to 2500, preferably 500 to 2000.

Silicone Compounds (H1) which have at Least One Polyether Group

As already explained above, the above-described silicone compounds (E), (G), (J) and (K), which also already have at least one hydrophilic group (specifically at least one group B)), are suitable as such for the use as component H1). This is true specifically for the compounds (E), (G), (J) and (K), which have at least one group (F) with alkylene oxide repeat units. Reference is hereby made to the prior disclosure relating to silicone compounds (E), (G), (J) and (K) in its entirety. Also of specific suitability is the compound with the INCI name Methoxy PEG/PPG-7/3 Aminopropyl Dimethicone (e.g. ABIL® Soft AF 100, Evonik Industries).

The component H1) is preferably used in an amount of from 0.1 to 15 parts by weight, particularly preferably 0.3 to 10 parts by weight, based on 100 parts by weight of the monomers used for the polymerization.

Basic Compound H2)

As base H2), it is possible to use alkali metal bases such as sodium hydroxide solution, potassium hydroxide solution, sodium carbonate, sodium hydrogencarbonate, potassium carbonate or potassium hydrogencarbonate.

In one preferred embodiment, the component H2) is selected from basic compounds different from H1) which have at least one nitrogen-atom-containing group which is selected from amine groups and ammonium groups.

Suitable amino-group-containing compounds within the context of the invention are in principle compounds which have at least one primary, secondary or tertiary amino group or a quaternary ammonium group. Preferred compounds having at least one quaternary ammonium group are those which can serve as $NH_3$ source when used in the process according to the invention.

The compound H2) is preferably selected from $NH_3$, $(NH_4)_2CO_3$, $NH_4HCO_3$, monoalkylamines, dialkylamines, trialkylamines, amino alcohols, nitrogen-containing heterocycles and mixtures thereof.

Suitable compounds H2) are $NH_3$ and compounds which are capable of releasing $NH_3$ under the reaction conditions. These include preferably $(NH_4)_2CO_3$ and $NH_4HCO_3$. Particularly preferably, the component H2) comprises ammonium hydrogencarbonate or consists of ammonium hydrogencarbonate.

The amino-group-containing compound used in the process according to the invention is preferably anhydrous. Within the context of the invention, "anhydrous" is understood as meaning that the amount of water added to the reaction mixture with the amino-group-containing compound and the amount of water optionally liberated when using compounds with quaternary ammonium groups is so small that the reaction mixture used for the preparation of the copolymer composition CP) has a water content of at most 2% by weight throughout the entire course of the copolymerization.

Preferred amino-group-containing compounds H2) are $C_1$-$C_6$-alkylamines, particularly preferably n-propylamine and n-butylamine.

Preferred amino-group-containing compounds H2) are also di($C_1$-$C_6$-alkyl)amines, particularly preferably diethylpropylamine and dipropylmethylamine.

Preferred amino-group-containing compounds H2) are also tri($C_1$-$C_6$-alkyl)amines, particularly preferably trimethylamine, triethylamine, triisopropylamine, etc.

Preferred amino-group-containing compounds H2) are also amino alcohols, e.g. monoalkanolamines, dialkanolamines, trialkanolamines, alkyldialkanolamines, dialkylalkanolamines and mixtures thereof.

The compound H2) is particularly preferably selected from ethanolamine, diethanolamine, triethanolamine, methyldiethanolamine, ethyldiethanolamine, dimethylethanolamine, 2-amino-2-methyl-1-propanol and mixtures thereof.

Furthermore, the base is preferably selected from nitrogen-containing heterocycles. Preferably, the nitrogen-containing heterocycles are selected from the group of pyrroles, pyrrolidines, pyridines, quinolines, isoquinolines, purines, pyrazoles, imidazoles, triazoles, tetrazoles, indolizines, pyridazines, pyrimidines, pyrazines, triazines, indoles, isoindoles, oxazoles, oxazolidones, oxazolidines, morpholines, piperazines, piperidines and derivatives thereof. Suitable derivatives of the aforementioned nitrogen-containing heterocycles can have at least one further substituent which is preferably selected from alkyl, cycloalkyl, heterocycloalkyl, aryl, hetaryl, alkoxy, cycloalkoxy, aryloxy, COOH, carboxylate, $SO_3H$, sulfonate, alkoxycarbonyl, acyl and nitro. The nitrogen-containing heterocycles can specifically have one or more $C_1$-$C_6$-alkyl substituents, such as methyl, ethyl, n-propyl, isopropyl, n-butyl, sec-butyl, tert-butyl etc.

Preferably, the component b) comprises imidazole or a derivative thereof. Particular preference is given to N-vinylimidazole. Preference is also given to imidazole or imidazole derivatives of the general formula (L),

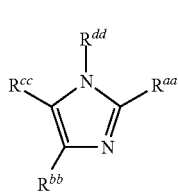

(L)

in which $R^{aa}$, $R^{bb}$ and $R^{cc}$, independently of one another, are selected from hydrogen, $C_1$-$C_4$-alkyl, specifically methyl, ethyl, n-propyl, isopropyl, n-butyl and tert-butyl, $C_5$-$C_8$-cycloalkyl, specifically cyclohexyl, and $C_6$-$C_{10}$-aryl, specifically phenyl.

Examples of compounds of the general formula (L) can be found in table 1 below:

TABLE 1

| $R^{aa}$ | $R^{bb}$ | $R^{cc}$ | $R^{dd}$ |
|---|---|---|---|
| H | H | H | H |
| Me | H | H | H |
| H | Me | H | H |
| H | H | Me | H |
| Me | Me | H | H |
| H | Me | Me | H |
| Me | H | Me | H |
| Ph | H | H | H |
| H | Ph | H | H |
| H | H | Ph | H |
| Ph | Me | H | H |
| Ph | H | Me | H |
| Me | Ph | H | H |
| H | Ph | Me | H |
| H | Me | Ph | H |
| Me | H | Ph | H |
| H | H | H | Me |
| H | H | H | $C_2H_5$ |

Me = methyl
Ph = phethyl

A further preferred imidazole derivative is histidine.

Preferably, the component H2) comprises at least one imidazole compound or consists of at least one imidazole compound. The imidazole compound H2) is particularly preferably selected from imidazole and N-alkylimidazoles. Preferred N-alkylimidazoles are N-methylimidazole and N-ethylimidazole. Particularly preferably, the component H2) comprises imidazole or consists of imidazole.

The aforementioned amino-group-containing compounds can be used individually or in the form of any desired mixtures.

Preferably, the component H2) is used in an amount of from 0.1 to 15 parts by weight, particularly preferably 0.3 to 10 parts by weight, based on 100 parts by weight of the monomers used for the polymerization.

Copolymer Composition CP)

The preparation of the copolymer compositions CP) according to the invention takes place by precipitation polymerization. During the precipitation polymerization, the monomers used are soluble in the reaction medium (monomer, solvent), but the corresponding polymer is not. The resulting polymer becomes insoluble under the selected polymerization conditions and precipitates out of the reaction mixture. The process according to the invention itself is characterized by advantageous properties and moreover also leads to copolymer compositions with particularly advantageous properties. The precipitation polymers present in the polymer compositions according to the invention are characterized by their ability as rheology modifiers (specifically as thickeners). The dried formulations are very readily redispersible and are characterized by a high dissolution rate. They are suitable for formulating gels with improved clarity and/or improved structural properties and/or improved ability to be washed out compared with gels based on conventional polymer compositions. Moreover, no undesirably extensive increase in the viscosity of the reaction medium results during the polymerization. Deposit formation can generally be successfully avoided.

Preferably, the reaction mixture used for the preparation of the copolymer composition CP) over the entire course of the copolymerization has a water content of at most 5% by weight, particularly preferably at most 3% by weight, in particular at most 2% by weight.

Monomer a)

To prepare the copolymer compositions CP) according to the invention, acrylic acid is used as component a). According to the invention, component a) is used in an amount of from 70 to 100% by weight, based on the total weight of the compounds used for the polymerization. Component a) is used particularly preferably in an amount of from 70 to 99.99% by weight, in particular 75 to 99.9% by weight, based on the total weight of the compounds used for the polymerization (i.e. the monomers a) and, if present, b) to f) add up to 100% by weight).

In a first preferred embodiment, the monomer composition used for the preparation of the copolymer composition CP) by free-radical copolymerization consists only of the components a) and c). The component a) is then used preferably in an amount of from 95 to 99.99% by weight, particularly preferably from 98 to 99.9% by weight, based on the total weight of the compounds a) and c) used for the polymerization. The process according to the invention then serves specifically for the preparation of crosslinked polyacrylic acid.

In a second preferred embodiment, the component a) is used in an amount of from 70 to 99.99% by weight, preferably 75 to 99.9% by weight, based on the total weight of the compounds used for the polymerization (i.e. components a) to g)). In this embodiment, the monomer composition used for the preparation of the copolymer composition CP) also comprises at least one further monomer as well as the components a) and c).

Hydrophilic, Nonionic Monomer b)

The monomer b) is preferably selected from the monomers b1) to b4) listed below, mixtures of monomers from one of the monomer classes b1) to b4), and mixtures of monomers from two or more monomer classes b1) to b4).

According to the invention, the component a) is used in an amount of from 0 to 30% by weight, based on the total weight of the compounds used for the polymerization. Preferably, the component b) is used in an amount of from 0.1 to 29.99% by weight, particularly preferably 0.5 to 25% by weight, based on the total weight of the monomers used for the polymerization.

Amide-Group-Containing Monomer b1)

The monomer composition used for the preparation of the copolymer composition CP) can additionally comprise, in copolymerized form, at least one amide-group-containing monomer b1) of the general formula (IV)

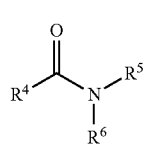

(IV)

where
one of the radicals $R^4$ to $R^6$ is a group of the formula $CH_2=CR^7—$ where $R^7=H$ or $C_1$-$C_4$-alkyl and the other radicals $R^4$ to $R^6$, independently of one another, are h, alkyl, cycloalkyl, heterocycloalkyl, aryl or hetaryl,
where $R^4$ and $R^5$, together with the amide group to which they are bonded, may also be a lactam having 5 to 8 ring atoms,
where $R^5$ and $R^6$, together with the nitrogen atom to which they are bonded, may also be a five- to seven-membered heterocycle,
with the proviso that the sum of the carbon atoms of the radicals $R^4$, $R^5$ and $R^6$ is at most 8.

Preferably, the compounds of the component b1) have at most 7 further carbon atoms in addition to the carbonyl carbon atom of the amide group.

Preferably, the compounds of the component b1) are selected from primary amides of α,β-ethylenically unsaturated monocarboxylic acids, N-vinylamides of saturated monocarboxylic acids, N-vinyllactams, N-alkyl- and N,N-dialkylamides of α,β-ethylenically unsaturated monocarboxylic acids and mixtures thereof.

Preferred monomers b1) are N-vinyllactams and derivatives thereof, which can have e.g. one or more $C_1$-$C_6$-alkyl substituents, such as methyl, ethyl, n-propyl, isopropyl, n-butyl, sec-butyl, tert-butyl, etc. These include e.g. N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc.

Particular preference is given to using N-vinylpyrrolidone and/or N-vinylcaprolactam.

Suitable monomers b1) are also acrylamide and methacrylamide.

Suitable N-alkyl- and N,N-dialkylamides of α,β-ethylenically unsaturated monocarboxylic acids which have at most 7 further carbon atoms in addition to the carbonyl carbon atom of the amide group are, for example, N-methyl(meth)acrylamide, N-ethyl(meth)acrylamide, N-propyl(meth)acrylamide, N-(n-butyl)(meth)acrylamide, N-tertbutyl(meth)acrylamide, n-pentyl(meth)acrylamide, n-hexyl(meth)acrylamide, n-heptyl(meth)acrylamide, N,N-dimethyl(meth)acrylamide, N,N-diethyl(meth)acrylamide, piperidinyl(meth)acrylamide, morpholinyl(meth)acrylamide and mixtures thereof.

Open-chain N-vinylamide compounds suitable as monomers b1) are for example N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide, N-vinylbutyramide and mixtures thereof. Preference is given to using N-vinylformamide.

Preferably, the component b1) is used in an amount of from 0.1 to 29.99% by weight, particularly preferably 0.5 to 25% by weight, based on the total weight of the monomers used for the polymerization.

Monomer b2)

In a further embodiment, the monomer composition used for the preparation of the copolymer composition can additionally comprise, in copolymerized form, at least one further monomer b2) which has a group of the formulae (Va) or (Vb)

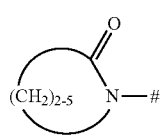

(Va)

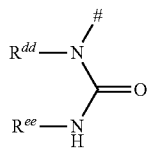

(Vb)

in which
# is the binding site to a group with a free-radically polymerizable, α,β-ethylenically unsaturated double bond, where in the compounds (Va) # is not the binding site to a group of the formula $CH_2=CR^7—$ where $R^7=H$ or $C_1$-$C_4$-alkyl (=monomers b1),
$R^{dd}$ is H or $C_1$-$C_4$-alkyl,
$R^{ee}$ is H or $C_1$-$C_4$-alkyl, or
$R^{dd}$ and $R^{ee}$ together are $(CH_2)_{1-4}$.

Preferably, the monomer b2) is selected from monomers having a group of the formulae (Va.1) or (Vb.1)

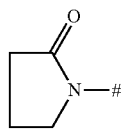

(Va.1)

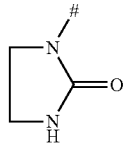

(Vb.1)

Preferred monomers b2) are the compounds of the formula:

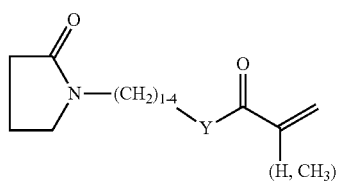

in which Y is O or $NR^y$, in which $R^y$ is h, alkyl, cycloalkyl or aryl.

Specific monomers b2) are the compounds of the formula:

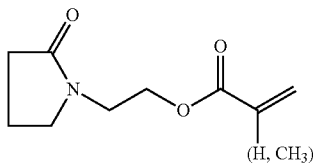

(H, CH₃)

Suitable monomers b2) having urea groups are e.g. N-vinyl- or N-allylurea or derivatives of imidazolidin-2-one. These include N-vinyl- and N-allylimidazolidin-2-one, N-vinyloxyethylimidazolidin-2-one, N-(2-(meth)acrylamidoethyl)imidazolidin-2-one, N-(2-(meth)acryloxyethyl)imidazolidin-2-one (=2-ureido(meth)acrylate), N-[2-((meth)acryloxyacetamido)ethyl]imidazolidin-2-one etc.

Preferred monomers b2) having urea groups are N-(2-acryloxyethyl)imidazolidin-2-one and N-(2-methacryloxyethyl)imidazolidin-2-one. Particular preference is given to N-(2-methacryloxyethyl)imidazolidin-2-one (2-ureidomethacrylate, UMA).

Preferably, the component b2) is used in an amount of from 0.1 to 20% by weight, particularly preferably 0.5 to 10% by weight, based on the total weight of the monomers used for the polymerization.

Monomer b3)

In a further embodiment, the monomer composition used for the preparation of the copolymer composition can additionally comprise, in copolymerized form, at least one further monomer b3) which is selected from esters of $\alpha,\beta$-ethylenically unsaturated mono- and dicarboxylic acids with $C_2$-$C_{30}$-diols, amides of $\alpha,\beta$-ethylenically unsaturated mono- and dicarboxylic acids with $C_2$-$C_{30}$-amino alcohols, which have a primary or secondary amino group, and mixtures thereof.

Suitable additional monomers b3) are also 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate and 3-hydroxy-2-ethylhexyl methacrylate.

Suitable additional monomers b3) are also 2-hydroxyethylacrylamide, 2-hydroxyethylmethacrylamide, 2-hydroxyethylethacrylamide, 2-hydroxypropylacrylamide, 2-hydroxypropylmethacrylamide, 3-hydroxypropylacrylamide, 3-hydroxypropylmethacrylamide, 3-hydroxybutylacrylamide, 3-hydroxybutylmethacrylamide, 4-hydroxybutylacrylamide, 4-hydroxybutylmethacrylamide, 6-hydroxyhexylacrylamide, 6-hydroxyhexylmethacrylamide, 3-hydroxy-2-ethylhexylacrylamide and 3-hydroxy-2-ethylhexylmethacrylamide.

Preferably, the component b3) is used in an amount of from 0.1 to 25% by weight, particularly preferably 0.5 to 20% by weight, based on the total weight of the monomers used for the polymerization.

Monomer b4)

At least one monomer b4), different from the components a) to f) and copolymerizable therewith, can additionally be used for the preparation of the copolymer composition CP) according to the invention.

Suitable compounds b4) are selected from compounds of the general formulae VI a) and VI b)

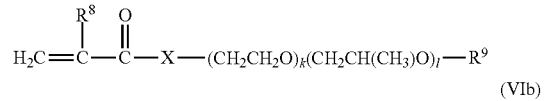

$$H_2C=CH-CH_2-O-(CH_2CH_2O)_k(CH_2CH(CH_3)O)_l-R^9 \quad \text{(VIb)}$$

in which
the order of the alkylene oxide units is arbitrary,
k and l, independently of one another, are an integer from 0 to 1000, where the sum of
k and l is at least 5,
$R^8$ is hydrogen or $C_1$-$C_8$-alkyl,
$R^9$ is hydrogen, $C_1$-$C_{30}$-alkyl, $C_2$-$C_{30}$-alkenyl or $C_5$-$C_8$-cycloalkyl,
X is O or a group of the formula $NR^{10}$, in which $R^{10}$ is h, alkyl, alkenyl, cycloalkyl, heterocycloalkyl, aryl or hetaryl.

In the formulae VI a) and VI b), k is preferably an integer from 1 to 500, in particular 3 to 250. Preferably, l is an integer from 0 to 100.

Preferably, $R^8$ in the formula VI a) is hydrogen, methyl, ethyl, n-propyl, isopropyl, n-butyl, sec-butyl, tert-butyl, n-pentyl or n-hexyl, in particular hydrogen, methyl or ethyl.

Preferably, $R^9$ in the formulae VI a) and VI b) is hydrogen, methyl, ethyl, n-propyl, isopropyl, n-butyl, sec-butyl, n-pentyl, n-hexyl, n-heptyl, n-octyl, 1,1,3,3-tetramethylbutyl, ethylhexyl, n-nonyl, n-decyl, n-undecyl, tridecyl, myristyl, pentadecyl, palmityl, heptadecyl, octadecyl, nonadecyl, arrachinyl, behenyl, lignocerenyl, cerotinyl, melissinyl, palmitoleinyl, oleyl, linolyl, linolenyl, stearyl, lauryl.

Preferably, X in the formula VI a) is O or NH.

Suitable polyether acrylates VI a) are, for example, the polycondensation products of the aforementioned $\alpha,\beta$-ethylenically unsaturated mono- and/or dicarboxylic acids and their acid chlorides, amides and anhydrides with polyetherols. Suitable polyetherols can be prepared easily by reacting ethylene oxide, 1,2-propylene oxide and/or epichlorohydrin with a starter molecule, such as water or a short-chain alcohol $R^9$—OH. The alkylene oxides can be used individually, alternately one after the other or as a mixture. The polyether acrylates VI a) can be used on their own or in mixtures for the preparation of the polymers used according to the invention.

Suitable allyl alcohol alkoxylates VI b) are, for example, the etherification products of allyl chloride with corresponding polyetherols. Suitable polyetherols can be prepared easily by reacting ethylene oxide, 1,2-propylene oxide and/or epichlorohydrin with a starter alcohol $R^9$—OH. The alkylene oxides can be used individually, alternately one after the other or as a mixture. The allyl alcohol alkoxylates VI b) can be used on their own or in mixtures for the preparation of the polymers used according to the invention.

Crosslinker c)

To prepare the copolymer compositions CP), at least one crosslinker, i.e. a compound with two or more than two ethylenically unsaturated, nonconjugated double bonds, is used according to the invention.

Preferably, crosslinkers are used in an amount of from 0.01 to 5% by weight, particularly preferably 0.1 to 4% by weight, based on the total weight of the compounds used for the polymerization.

Suitable crosslinkers c) are, for example, acrylic esters, methacrylic esters, allyl ethers or vinyl ethers of at least dihydric alcohols. The OH groups of the parent alcohols here may be completely or partially etherified or esterified; however, the crosslinkers comprise at least two ethylenically unsaturated groups.

Examples of the parent alcohols are dihydric alcohols such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, hydroxypivalic acid neopentyl glycol monoester, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiapentane-1,5-diol, and also polyethylene glycols, polypropylene glycols and polytetrahydrofurans with molecular weights of in each case 200 to 10 000. Apart from the homopolymers of ethylene oxide and propylene oxide, it is also possible to use block copolymers of ethylene oxide or propylene oxide or copolymers which comprise ethylene oxide and propylene oxide groups in incorporated form. Examples of parent alcohols having more than two OH groups are trimethylolpropane, glycerol, pentaerythritol, 1,2,5-pentanetriol, 1,2,6-hexanetriol, cyanuric acid, sorbitans, sugars such as sucrose, glucose, mannose. The polyhydric alcohols can of course also be used following reaction with ethylene oxide or propylene oxide as the corresponding ethoxylates or propoxylates. The polyhydric alcohols can also firstly be converted to the corresponding glycidyl ethers by reaction with epichlorohydrin. Preference is given to ethylene glycol di(meth)acrylate and polyethylene glycol di(meth)acrylates.

Further suitable crosslinkers c) are the vinyl esters or the esters of monohydric, unsaturated alcohols with ethylenically unsaturated $C_3$-$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, it is also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers c) are esters, different from (meth)acrylates, of unsaturated carboxylic acids with the polyhydric alcohols described above, for example oleic acid, crotonic acid, cinnamic acid or 10-undecenoic acid.

Suitable as crosslinker c) are, moreover, straight-chain or branched, linear or cyclic, aliphatic or aromatic hydrocarbons which have at least two double bonds which, in the case of aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20 000.

Also suitable as crosslinker c) are the acrylamides, methacrylamides and N-allylamines of at least difunctional amines. Such amines are, for example, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid or at least dibasic carboxylic acids, as have been described above.

Also suitable as crosslinker c) are triallylamine and triallylmonoalkylammonium salts, e.g. triallylmethylammonium chloride or methylsulfate.

Also suitable are N-vinyl compounds of urea derivatives, at least difunctional amides, cyanurates or urethanes, for example of urea, ethyleneurea, propyleneurea or tartardiamide, e.g. N,N'-divinylethyleneurea or N,N'-divinylpropyleneurea.

Further suitable crosslinkers c) are divinyldioxane, tetraallylsilane or tetravinylsilane.

Mixtures of the aforementioned compounds c) can of course also be used.

Very particularly preferred crosslinkers c) are ethylene glycol di(meth)acrylate, polyethylene glycol di(meth)acrylates, pentaerythritol triallyl ether, methylenebisacrylamide, N,N'-divinylethyleneurea, triallylamine and triallylmonoalkylammonium salts.

Cationogenic/Cationic Monomer d)

The monomer composition used for the preparation of the copolymer composition CP) can additionally comprise at least one compound d) with a free-radically polymerizable, α,β-ethylenically unsaturated double bond and at least one cationogenic and/or cationic group per molecule.

The component d) is preferably used in an amount of from 0.1 to 29.99% by weight, particularly preferably 0.2 to 25% by weight, based on the total weight of the compounds used for the polymerization.

Preferably, the copolymers present in the copolymer composition CP) have an excess of anionogenic and/or anionic groups. Consequently, if monomers d) are used, then it is preferably in amounts such that the copolymer in CP) has a molar excess of anionogenic/anionic groups compared with cationogenic/cationic groups of at least 5:1, preferably at least 10:1.

The cationogenic and/or cationic groups of component d) are preferably nitrogen-containing groups, such as primary, secondary and tertiary amino groups and also quaternary ammonium groups. The nitrogen-containing groups are preferably tertiary amino groups or quaternary ammonium groups. Charged cationic groups can be produced from the amine nitrogens either by protonation or by quaternization with acids or alkylating agents. These include, for example, carboxylic acids, such as lactic acid, or mineral acids, such as phosphoric acid, sulfuric acid and hydrochloric acid, or as alkylating agents $C_1$-$C_4$-alkyl halides or sulfates, such as ethyl chloride, ethyl bromide, methyl chloride, methyl bromide, dimethyl sulfate and diethyl sulfate. A protonation or quaternization can generally take place either before or after the polymerization.

The component d) is preferably selected from esters of α,β-ethylenically unsaturated mono- and dicarboxylic acids with amino alcohols, which may be mono- or dialkylated on the amine nitrogen, amides of α,β-ethylenically unsaturated mono- and dicarboxylic acids with diamines which have at least one primary or secondary amino group, N,N-diallylamine, N,N-diallyl-N-alkylamines and derivatives thereof, vinyl- and allyl-substituted nitrogen heterocycles, vinyl- and allyl-substituted heteroaromatic compounds, and mixtures thereof.

Preferred compounds d) are the esters of α,β-ethylenically unsaturated mono- and dicarboxylic acids with amino alcohols. Preferred amino alcohols are $C_2$-$C_{12}$-amino alcohols which are $C_1$-$C_8$-mono- or -dialkylated on the amine nitrogen. Of suitability as acid component of these esters are, for example, acrylic acid, methacrylic acid, fumaric acid, maleic acid, itaconic acid, crotonic acid, maleic anhydride, monobutyl maleate and mixtures thereof. Preference is given to using acrylic acid, methacrylic acid and mixtures thereof as acid component.

Preferred monomers d) are N-methylaminoethyl(meth)acrylate, N-ethylaminoethyl(meth)acrylate, N-(n-propyl)aminoethyl(meth)acrylate, N-(tert-butyl)aminoethyl(meth)acrylate, N,N-dimethylaminomethyl(meth)acrylate, N,N-dimethylaminoethyl(meth)acrylate, N,N-diethylaminomethyl(meth)acrylate, N,N-diethylaminoethyl(meth)acrylate, N,N-dimethylaminopropyl(meth)acrylate, N,N-diethylaminopropyl(meth)acrylate and N,N-dimethylaminocyclohexyl(meth)acrylate.

Particular preference is given to N,N-dimethylaminoethyl acrylate, N,N-dimethylaminoethyl methacrylate and mixtures thereof. Preferred monomers d) are in particular also the quaternization products of the aforementioned compounds.

In one very specific embodiment, the component d) consists only of N,N-dimethylaminoethyl(meth)acrylate.

Suitable monomers d) are also the amides of the aforementioned α,β-ethylenically unsaturated mono- or dicarboxylic acids with diamines which have at least one primary or secondary amino group. Preference is given to diamines which have one tertiary and one primary or secondary amino group.

Preferred monomers d) are, for example, N-[tert-butylaminoethyl](meth)acrylamide, N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]actylamide, N[4-(dimethylamino)butyl]methacrylamide, N-[2-(diethylamino)ethyl]acrylamide, N-[4-(dimethylamino)cyclohexyl]acrylamide and N-[4-(dimethylamino)cyclohexyl]methacrylamide.

In one suitable embodiment, the component d) comprises at least one N-vinylimidazole compound as vinyl-substituted heteroaromatic compound. In one specific embodiment, component d) is selected from N-vinylimidazole compounds and mixtures which comprise at least one N-vinylimidazole compound.

Suitable N-vinylimidazole compounds are compounds of the formula

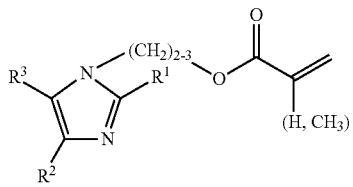

in which $R^1$ to $R^3$, independently of one another, are hydrogen, $C_1$-$C_4$-alkyl or phenyl. Preferably, $R^1$ to $R^3$ are hydrogen.

Also suitable are N-vinylimidazole compounds of the general formula (VII)

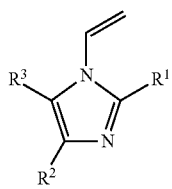

(VII)

in which $R^1$ to $R^3$, independently of one another, are hydrogen, $C_1$-$C_4$-alkyl or phenyl.

Examples of compounds of the general formula (VII) are given in table 1 below:

TABLE 1

| $R^1$ | $R^2$ | $R^3$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

As monomer d), preference is given to 1-vinylimidazole (N-vinylimidazole) and mixtures which comprise N-vinylimidazole.

Suitable monomers d) are also the compounds obtainable by protonation or quaternization of the aforementioned N-vinylimidazole compounds. Examples of such charged monomers d) are quaternized vinylimidazoles, in particular 3-methyl-1-vinylimidazolium chloride, methosulfate and ethosulfate. Suitable acids and alkylating agents are those listed previously. Preferably, a protonation or quaternization takes place after the polymerization.

Suitable monomers d) are also vinyl- and allyl-substituted nitrogen heterocycles different from vinylimidazoles, such as 2- and 4-vinylpyridine, 2- and 4-allylpyridine, and the salts thereof.

Anionogenic/Anionic Monomer e)

In the process according to the invention for the preparation of the copolymer composition CP) a compound, different from acrylic acid, having a free-radically polymerizable, α,β-ethylenically unsaturated double bond and at least one anionogenic and/or anionic group per molecule can optionally be used as component e). The component e) is preferably used in an amount of from 0 to 29.99% by weight, particularly preferably from 0 to 25% by weight, based on the total weight of the compounds used for the polymerization. If present, the component e) is preferably used in an amount of from 0.1 to 29.99% by weight, particularly preferably from 0.5 to 25% by weight, based on the total weight of the compounds used for the polymerization.

Preferably, the compounds e) are selected from monoethylenically unsaturated carboxylic acids, sulfonic acids, phosphonic acids and mixtures thereof.

The monomers e) include monoethylenically unsaturated mono- and dicarboxylic acids having 3 to 25, preferably 3 to 6, carbon atoms, which can also be used in the form of their salts or anhydrides. Examples thereof are methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. The monomers e) also include the half-esters of monoethylenically unsaturated dicarboxylic acids having 4 to 10, preferably 4 to 6, carbon atoms, e.g. of maleic acid, such as monomethyl maleate. The monomers e) also include monoethylenically unsaturated sulfonic acids and phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, styrenesulfonic acid, 2-acrylamido-2-methylpropanesulfonic acid, vinylphosphonic acid and allylphosphonic acid. The monomers e) also include the salts of the aforementioned acids, in particular the sodium, potassium and ammonium salts, and also the salts with amines. The monomers e) can be used as such or as mixtures with one another. The stated weight fractions all refer to the acid form.

Preferably, the component e) is selected from methacrylic acid, ethacrylic acid, α-chloroacrylic acid, crotonic acid, maleic acid, maleic anhydride, fumaric acid, itaconic acid, citraconic acid, mesaconic acid, glutaconic acid, aconitic acid and mixtures thereof.

Particular preference is given to using methacrylic acid as component e).

Further Monomers f)

To prepare the copolymer composition CP) it is possible to additionally use at least one compound f) which is selected from esters of α,β-ethylenically unsaturated mono- and dicarboxylic acids with $C_1$-$C_{30}$-alkanols, amides of α,β-ethylenically unsaturated mono- and dicarboxylic acids with mono- and di($C_1$-$C_{30}$-alkyl)amines, N,N-diallylamines, acid addition salts and quaternization products thereof, N,N-diallyl-N-alkylamines, acid addition salts and quaternization products thereof, urethane(meth)acrylates with alkylene oxide groups, esters of vinyl alcohol and allyl alcohol with $C_1$-$C_{30}$-monocarboxylic acids, $C_1$-$C_{30}$-alkyl vinyl ethers, vinylaromatics, vinyl halides, vinylidene halides, $C_2$-$C_8$-monoolefins, non-aromatic hydrocarbons with at least two conjugated double bonds and mixtures thereof.

Suitable esters of α,β-ethylenically unsaturated mono- and dicarboxylic acids with $C_1$-$C_{30}$-alkanols are, for example, methyl(meth)acrylate, methyl ethacrylate, ethyl(meth)acrylate, ethyl ethacrylate, n-propyl(meth)acrylate, isopropyl(meth)acrylate, n-butyl(meth)acrylate, tert-butyl(meth)acrylate, tert-butyl ethacrylate, n-pentyl(meth)acrylate, n-hexyl(meth)acrylate, n-heptyl(meth)acrylate, n-octyl(meth)acrylate, 1,1,3,3-tetramethylbutyl(meth)acrylate, ethylhexyl(meth)acrylate, n-nonyl(meth)acrylate, n-decyl(meth)acrylate, n-undecyl(meth)acrylate, tridecyl(meth)acrylate, myristyl(meth)acrylate, pentadecyl(meth)acrylate, palmityl(meth)acrylate, heptadecyl(meth)acrylate, nonadecyl(meth)acrylate, arrachinyl(meth)acrylate, behenyl(meth)acrylate, lignocerenyl(meth)acrylate, cerotinyl(meth)acrylate, melissinyl(meth)acrylate, palmitoleinyl(meth)acrylate, oleyl(meth)acrylate, linolyl(meth)acrylate, linolenyl(meth)acrylate, stearyl(meth)acrylate, lauryl(meth)acrylate and mixtures thereof.

Suitable amides of α,β-ethylenically unsaturated mono- and dicarboxylic acids with mono- and di($C_1$-$C_{30}$-alkyl) amines are, for example, methyl(meth)acrylamide, methylethacrylamide, ethyl(meth)acrylamide, ethylethacrylamide, n-propyl(meth)acrylamide, isopropyl(meth)acrylamide, n-butyl(meth)acrylamide, tertbutyl(meth)acrylamide, tert-butylethacrylamide, n-pentyl(meth)acrylamide, n-hexyl(meth)acrylamide, n-heptyl(meth)acrylamide, n-octyl(meth)acrylamide, 1,1,3,3-tetramethylbutyl(meth)acrylamide, ethylhexyl(meth)acrylamide, n-nonyl(meth)acrylamide, n-decyl(meth)acrylamide, n-undecyl(meth)acrylamide, tridecyl(meth)acrylamide, myristyl(meth)acrylamide, pentadecyl(meth)acrylamide, palmityl(meth)acrylamide, heptadecyl(meth)acrylamide, nonadecyl(meth)acrylamide, arrachinyl(meth)acrylamide, behenyl(meth)acrylamide, lignocerenyl(meth)acrylamide, cerotinyl(meth)acrylamide, melissinyl(meth)acrylamide, palmitoleinyl(meth)acrylamide, oleyl(meth)acrylamide, linolyl(meth)acrylamide, linolenyl(meth)acrylamide, stearyl(meth)acrylamide, lauryl(meth)acrylamide, N-methyl-N-(n-octyl)(meth)acrylamide, N,N'-di-(n-octyl)(meth)acrylamide and mixtures thereof.

Suitable $C_1$-$C_{30}$-alkyl vinyl ethers are, for example, methyl vinyl ether, ethyl vinyl ether, n-propyl vinyl ether, isopropyl vinyl ether, n-butyl vinyl ether, tert-butyl vinyl ether, n-pentyl vinyl ether, n-hexyl vinyl ether, n-heptyl vinyl ether, n-octyl vinyl ether, 1,1,3,3-tetramethyl butyl vinyl ether, ethylhexyl vinyl ether, n-nonyl vinyl ether, n-decyl vinyl ether, n-undecyl vinyl ether, tridecyl vinyl ether, myristyl vinyl ether, pentadecyl vinyl ether, palmityl vinyl ether, heptadecyl vinyl ether, octadecyl vinyl ether, nonadecyl vinyl ether, arrachinyl vinyl ether, behenyl vinyl ether, lignocerenyl vinyl ether, cerotinyl vinyl ether, melissinyl vinyl ether, palmitoleinyl vinyl ether, oleyl vinyl ether, linolyl vinyl ether, linolenyl vinyl ether, stearyl vinyl ether, lauryl vinyl ether and mixtures thereof.

Suitable esters of vinyl alcohol with $C_1$-$C_{30}$-monocarboxylic acids are, for example, methyl vinyl ester, ethyl vinyl ester, n-propyl vinyl ester, isopropyl vinyl ester, n-butyl vinyl ester, tert-butyl vinyl ester, n-pentyl vinyl ester, n-hexyl vinyl ester, n-heptyl vinyl ester, n-octyl vinyl ester, 1,1,3,3-tetramethylbutyl vinyl ester, ethylhexyl vinyl ester, n-nonyl vinyl ester, n-decyl vinyl ester, n-undecyl vinyl ester, tridecyl vinyl ester, myristyl vinyl ester, pentadecyl vinyl ester, palmityl vinyl ester, heptadecyl vinyl ester, octadecyl vinyl ester, nonadecyl vinyl ester, arrachinyl vinyl ester, behenyl vinyl ester, lignocerenyl vinyl ester, cerotinyl vinyl ester, melissinyl vinyl ester, palmitoleinyl vinyl ester, oleyl vinyl ester, linolyl vinyl ester, linolenyl vinyl ester, stearyl vinyl ester, lauryl vinyl ester and mixtures thereof.

Suitable monomers f) are also N,N-diallylamines and N,N-diallyl-N-alkylamines and acid addition salts and quaternization products thereof. Alkyl here is preferably $C_1$-$C_{24}$-alkyl. Preference is given to N,N-diallyl-N-methylamine and N,N-diallyl-N,N-dimethylammonium compounds, such as e.g. the chlorides and bromides. Particular preference is given to N,N-diallyl-N-methylammonium chloride (DADMAC).

Suitable urethane(meth)acrylates having alkylene oxide groups f) are described in DE 198 38 851 (component e2)), to which reference is made here in its entirety.

Suitable additional monomers f) are also vinyl acetate, vinyl propionate, vinyl butyrate and mixtures thereof.

Suitable additional monomers f) are also ethylene, propylene, isobutylene, butadiene, styrene, α-methylstyrene, acrylonitrile, methacrylonitrile, vinyl chloride, vinylidene chloride, vinyl fluoride, vinylidene fluoride and mixtures thereof.

The aforementioned monomers f) can be used in each case individually or in the form of any desired mixtures.

Preferably, the component f) is used in an amount of from 0 to 20% by weight, based on the total weight of the monomers used for the polymerization. A suitable use amount for additional monomers f) is in a range from 0.1 to 10% by weight, in particular 0.2 to 5% by weight, based on the total weight of the compounds used for the polymerization.

In a first preferred embodiment of the process according to the invention, for the preparation of the copolymer composition CP), based on the total weight of the monomers used for the polymerization, 98 to 99.9% by weight of acrylic acid a), and
0.1 to 2% by weight of at least one crosslinking compound c),
are used.

In a further preferred embodiment of the process according to the invention, for the preparation of the copolymer composition CP), based on the total weight of the monomers used for the polymerization, 93 to 99.7% by weight of acrylic acid a),
0.2 to 5% by weight of at least one compound d) with a free-radically polymerizable, α,β-ethylenically unsaturated double bond and at least one cationogenic and/or cationic group per molecule, preferably vinylimidazole, and
0.1 to 2% by weight of at least one crosslinking compound c), are used.

In a further preferred embodiment of the process according to the invention, for the preparation of the copolymer composition CP), based on the total weight of the monomers used for the polymerization, 70 to 99.4% by weight of acrylic acid a),
0 to 29.4% by weight of at least one compound e), different from acrylic acid, having a free-radically polymerizable, α,β-ethylenically unsaturated double bond and at least one anionogenic and/or anionic group per molecule,
0.5 to 20% by weight of at least one compound b3) and/or b4), and
0.1 to 2% by weight of at least one crosslinking compound c)

are used, with the proviso that the total amount of the monomers a) and b) is 78 to 99.4% by weight.

In a specific version to the aforementioned embodiment, for the preparation of the copolymer composition CP), based on the total weight of the monomers used for the polymerization, 70 to 99.4% by weight of acrylic acid a),
0 to 29.9% by weight of at least one compound e), different from acrylic acid, having a free-radically polymerizable α,β-ethylenically unsaturated double bond and at least one anionogenic and/or anionic group per molecule,
0 to 20% by weight of at least one monomer b3) which is selected from $C_1$-$C_7$-alkyl(meth)acrylates, in particular methyl(meth)acrylate, ethyl(meth)acrylate, n-butyl(meth)acrylate and mixtures thereof,
0 to 20% by weight of at least one compound b4) which is preferably selected from $C_8$-$C_{22}$-alkyl(meth)acrylates, $C_8$-$C_{22}$-alkyl vinyl ethers, polyether(meth)acrylates terminated with $C_8$-$C_{22}$-alkyl groups, allyl alcohol alkoxylates terminated with $C_8$-$C_{22}$-alkyl groups, $C_8$-$C_{22}$-carboxylic acid vinyl esters and mixtures thereof, and
0.1 to 2% by weight of at least one crosslinking compound c)

are used, with the proviso that the total amount of the monomers a) and e) is 78 to 99.4% by weight and the sum of monomers b3) and b4) is 0.5 to 20% by weight.

In the two aforementioned embodiments, preferably methacrylic acid is used as component e). A preferred ester of an α,β-ethylenically unsaturated monocarboxylic acid with a $C_1$-$C_7$-alkanol is methyl methacrylate. A mixture of a $C_{18-22}$-alkyl polyethylene glycol methacrylate with methyl methacrylate is commercially available under the name Plex-6877-O. A mixture of a $C_{16-18}$-alkyl polyethylene glycol methacrylate with methacrylic acid is commercially available under the name Lutencryl 250.

In a further preferred embodiment of the process according to the invention, for the preparation of the copolymer composition CP), based on the total weight of the monomers used for the polymerization, 70 to 99.4% by weight of acrylic acid a),
0 to 29.4% by weight of at least one compound e), different from acrylic acid, having a free-radically polymerizable α,β-ethylenically unsaturated double bond and at least one anionogenic and/or anionic group per molecule,
0.5 to 10% by weight, based on the total weight of a) and e), of at least one compound e) which is preferably selected from esters of α,β-ethylenically unsaturated mono- and dicarboxylic acids with $C_8$-$C_{30}$-alkanols, and
0.1 to 2% by weight of at least one crosslinking compound c), are used, with the proviso that the total amount of the monomers a) and e) is 88 to 99.4% by weight.

In the aforementioned embodiment, methacrylic acid is preferably used as component e).

In a further preferred embodiment of the process according to the invention, for the preparation of the copolymer composition CP), based on the total weight of the monomers used for the polymerization, 70 to 99.4% by weight of acrylic acid a),
0 to 29.8% by weight of at least one compound b), different from acrylic acid, having a free-radically polymerizable α,β-ethylenically unsaturated double bond and at least one anionogenic and/or anionic group per molecule,
0 to 5% by weight of at least one compound d) with a free-radically polymerizable, α,β-ethylenically unsaturated double bond and at least one cationogenic and/or cationic group per molecule, preferably vinylimidazole,
0.1 to 30% by weight of at least one amide-group-containing compound e), preferably vinylpyrrolidone and/or vinylcaprolactam, and
0.1 to 2% by weight of at least one crosslinking compound c)

are used, with the proviso that the total amount of the monomers a) and e) is 65 to 99.8% by weight.

In a specific version to the aforementioned embodiment, for the preparation of the copolymer composition CP), based on the total weight of the monomers used for the polymerization, 65 to 98.7% by weight of acrylic acid a),
0.2 to 5% by weight of vinylimidazole,
1 to 30% by weight of vinylpyrrolidone and/or vinylcaprolactam,
0.1 to 2% by weight of at least one crosslinking compound c), are used.

Precipitation Polymerization

According to the invention, the preparation of the copolymer composition CP) takes place by the method of precipitation polymerization. For this polymerization, solvents are used in which the starting materials for the polymerization are soluble and the polymer which is formed is insoluble. Preference is given to using an anhydrous aprotic solvent or solvent mixture. Suitable solvents are, for example, aromatic hydrocarbons such as toluene, xylenes, benzene; aliphatic and cycloaliphatic hydrocarbons such as n-alkanes or cyclohexane; esters of acetic acid such as ethyl acetate or butyl acetate; ethers, such as, for example, diethyl ether, dipropyl ether, dibutyl ether, methyl tert-butyl ether or diethylene glycol dimethyl ether; ketones such as acetone or methyl ethyl ketone, and mixtures of these solvents.

Preferably, the polymerization takes place in a mixture of cyclohexane and ethyl acetate. The ratio of cyclohexane to ethyl acetate is preferably in a range from 60:40 to 30:70. A preferred mixture is the azeotropic mixture of 53% cyclohexane and 47% ethyl acetate.

The precipitation polymerization is usually carried out at temperatures of from 20 to 150° C., preferably 40 to 120° C., in particular 60 to 100° C.

The precipitation polymerization is usually carried out at pressures of from 1 to 15 bar, in particular 1 to 6 bar. If the polymerization is not carried out under increased pressure, the solvent or solvent mixture determines the maximum reaction temperature through the corresponding boiling temperatures.

To prepare the polymers, the monomers can be polymerized with the help of initiators which form free radicals.

Initiators for the free-radical polymerization which can be used are the peroxo and/or azo compounds customary for this purpose, for example alkali metal or ammonium peroxidisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbarnate, bis(o-toluoyl)peroxide, didecanoyl peroxide, dioctanoyl peroxide, tert-butyl peroctoate, dilauroyl peroxide, tert-butyl perisobutyrate, tert-butyl peracetate, di-tert-amyl peroxide, tert-butyl hydroperoxide, 2,2'-azobisisobutyronitrile, azobis(2-amidinopropane) dihydrochloride, azobis(2,4-dimethylvaleronitrile) or 2,2'-azobis(2-methylbutyronitrile).

In a specific embodiment, for the preparation of the copolymers according to the invention, at least two free-radical initiators are used which permit an essentially independent initiation in at least two phases. Here, copolymers with particularly low residual monomer contents can be achieved. For the copolymerization, preference is then given to using at least two initiators whose disintegration temperatures differ from one another by at least 10° C. Within the context of the invention, the disintegration temperature is defined as the temperature at which 50% of the molecules disintegrate into free radicals within 2.5 hours. Preferably, the copolymerization takes place in the case of this procedure until conclusion of the precipitation of the copolymer at a temperature greater than or equal to the lower disintegration temperature and less than the higher disintegration temperature, and after the precipitation, a further reaction takes place at a temperature greater than or equal to the higher disintegration temperature.

The process according to the invention preferably comprises a first polymerization phase at a first polymerization temperature and a second polymerization phase at a second polymerization temperature above the first polymerization temperature, where, for the polymerization, at least two initiators are used whose half-lives at the first polymerization temperature differ in such a way that at least one of these initiators disintegrates into free radicals during the first polymerization phase and at least one of these initiators essentially does not disintegrate into free radicals during the first polymerization phase and disintegrates into free radicals during the second polymerization phase. Preferably, in the case of this procedure, the second polymerization phase starts essentially after precipitation of the copolymer. "Essentially" after precipitation of the copolymer is understood as meaning that the copolymer is present in precipitated form preferably to at least 80% by weight, preferably at least 90% by weight, in particular at least 95% by weight, based on the total weight of the copolymer.

The half-life of an initiator can be determined by customary methods known to the person skilled in the art, as described, for example, in the publication "Initiators for high polymers", Akzo Nobel, No. 10737. Preferably, the half-life of the first polymerization initiator at the first polymerization temperature and of the second polymerization initiator at the second polymerization temperature is in a range from about 1 minute to 3 hours, particularly preferably 5 minutes to 2.5 hours. If desired, it is also possible to use shorter half-lives, e.g. from 1 second to 1 minute or longer half-lives than 3 hours, provided it is ensured that the initiator(s) disintegrating at the higher temperature disintegrates into free radicals essentially during the second polymerization phase.

Preferably, the initiator system used comprises at least two initiators whose disintegration temperatures differ from one another by at least 15° C. The initiator which disintegrates at the lower temperature preferably has a disintegration temperature of from 50 to 100° C. The initiator disintegrating at the higher temperature preferably has a disintegration temperature of from 80 to 150° C.

In general, the precipitation polymerization can be carried out at solids contents up to ca. 30%. Preference is given to a range from 15 to 26%. By using the auxiliaries H1) and H2), it is generally possible to dispense with the use of further protective colloids. If desired, however, in the process according to the invention, a protective colloid different from H1) and H2) can additionally be used. Of suitability are the known protective colloid polymers which readily dissolve in the solvents used and do not react with the monomers. Suitable polymers are, for example, copolymers of maleic acid with vinyl alkyl ethers and/or olefins having 8 to 20 carbon atoms or corresponding copolymers of maleic acid half-esters with $C_{10}$-$C_{20}$-alcohols or else mono- and diamides of maleic acid with $C_{10}$-$C_{20}$-alkylamines, and polyvinyl alcohol ethers with alkyl groups which carry 1 to 20 carbon atoms and also polyvinyl methyl, ethyl, isobutyl or octadecyl ethers. The amount of protective colloid polymer used is generally 0.05 to 4% by weight, preferably 0.1 to 2% by weight (based on the total weight of the monomers used).

The polymerization can be carried out by initially introducing some of the solvent, the auxiliaries H1) and/or H2) and/or optionally protective colloid polymer, heating, and carrying out the polymerization by adding initiator, monomer(s) and crosslinker (in each case possibly dissolved in the same solvent or solvent mixture).

In an alternative embodiment, the crosslinker c) can be initially introduced in part or completely. It is likewise possible to initially introduce some of the monomers and the initiator (e.g. up to 50%, preferably up to 35%). The initial charge can then be heated to polymerization temperature and, after the reaction has started, the remainder of the mixture to be polymerized can be added according to the progress of the polymerization.

It is likewise possible not to initially introduce the crosslinker c) used, but to add it completely in the course of the polymerization.

The auxiliary H1) is preferably introduced as initial charge at least partly prior to the start of the polymerization. Alternatively to this, the auxiliary H1) can be added at least partly with one of the monomer feeds or as a separate feed. The auxiliary H2) is preferably added together with the acrylic acid a).

The precipitated polymer is then isolated from the reaction mixture, for which purpose any general method for isolating the polymers in the conventional precipitation polymerization can be used. Such methods are filtration, centrifugation, evaporation of the solvent or combinations of these methods.

The copolymer composition can if desired be subjected to a purification. This serves, for example, to remove nonpolymerized constituents and/or at least some of the auxiliaries. In one preferred embodiment, the copolymer composition CP) is isolated after the precipitation polymerization and subjected to a washing with a liquid washing medium. Suitable washing media are in principle the same solvents as are suitable for the polymerization. However, for easier drying of the polymers, it is advisable to use solvents with a low boiling point, such as, for example, acetone.

To remove impurities, the copolymer composition CP) can be subjected to a treatment with a washing medium once or several times in succession. For this, in a suitable device, the copolymer composition is brought into close contact with the washing medium and the washing medium is then separated off from the copolymer composition. Suitable devices are, for example, stirred reactors. In this connection, the treatment with the washing medium can take place in the container also used for the polymerization. The separation of copolymer and washing medium takes place, for example, by filtration or centrifugation. To increase the rate, the filtration can take place under increased pressure on the polymer side or reduced pressure on the discharge side.

The invention further provides the copolymer composition CP) obtainable by the process described above.

In addition to the polymer particles obtained during the precipitation polymerization, the copolymer composition CP) according to the invention generally comprises at least one of the auxiliary components H1) and/or H2). In one specific embodiment, the auxiliaries H1) and H2) used for the polymerization are not removed from the copolymer composition CP) according to the invention. Such copolymer compositions CP) generally have particularly advantageous properties. The copolymer composition CP) based on this auxiliary system can be dried easily, the resulting dry compositions are very readily redispersible and are characterized by a high dissolution rate. If desired, the auxiliaries H1) and/or H2) can be removed partly or completely from the copolymer composition CP), e.g. by at least one washing step, as described above.

The auxiliaries H1) and/or H2) can have an advantageous effect on further application-related properties of the copolymer composition CP), e.g. by reducing the dust formation, promoting pourable products or controlling particle size, molecular weight, morphology, etc.

The auxiliaries H1) and/or H2) can also have an advantageous effect on one or more other application-related properties of formulations of the copolymer composition CP). Thus, for example, the presence of at least one of these auxiliaries may have an advantageous effect on the clarity of the gels formulated with CP).

The copolymer compositions CP) according to the invention and the copolymers present therein are characterized by their pH-dependent solubility. Here, they are advantageously usually also readily soluble in a physiologically compatible pH range from 5 to 9. Furthermore, as a rule, a good thickening effect is also achieved in this pH range.

If the copolymers present in the copolymer composition CP) are to be both quaternized and neutralized, then preferably the quaternization takes place first and then the neutralization.

The copolymers present in the copolymer composition CP) are advantageously suitable for modifying the rheological properties of aqueous compositions. These may be, for example, an aqueous active ingredient or effect substance composition. These may quite generally be, for example, cosmetic compositions, pharmaceutical compositions, hygiene products, coatings, compositions for the paper industry and also the textile industry.

In one preferred embodiment, the compositions comprise at least one water-soluble or at least water-dispersible active ingredient or effect substance. The copolymers present in the copolymer composition CP) are of course also suitable to be used for modifying the rheological properties of compositions which comprise at least one water-insoluble (hydrophobic) active ingredient or effect substance.

Within the context of the present invention, "modification of rheological properties" is to be understood in the broad sense. The copolymers present in the copolymer composition CP) are generally suitable for thickening the consistency of aqueous compositions in a wide range. Depending on the basic consistency of the liquid compositions, flow properties from thin-liquid ranging to solid (in the sense of "no longer flowable") can generally be achieved, depending on the use amount of the copolymer. "Modification of rheological properties" is therefore understood as meaning, inter alia, the increase in the viscosity of liquids, the improvement in the thixotropic properties of gels, the solidification of gels and waxes etc. The compositions according to the invention are preferably suitable for the formulation of aqueous cosmetic and pharmaceutical products. Preferably, the compositions of the copolymers CP) are generally clear. Consequently, formulations, in particular cosmetic formulations, can be advantageously colored without impairment from the intrinsic color of the compositions. Furthermore, the compositions can be formulated in the form of clear gels.

The copolymer compositions CP) prepared in the presence of the auxiliary system according to the invention are characterized overall by advantageous rheological properties. The rheology-modifying properties can be further controlled via the type and use amount of the monomers used for the preparation of the copolymer compositions CP). This applies especially to the type and amount of crosslinker c) used. This further applies especially for the use of surface-active monomers in the preparation of CP), such as, for example, the polyether acrylates IV a) or allyl alcohol alkoxylates IV b).

A 0.2% strength by weight aqueous solution of a copolymer composition CP) generally has a viscosity in the range from 7000 to 15 000 mPas (values determined by means of Brookfield viscometer at 23° C. and 100 $s^{-1}$).

A 0.5% strength by weight aqueous solution of a copolymer composition CP) generally has a viscosity in the range from 15 000 to 60 000 mPas (values determined by means of Brookfield viscometer at 23° C. and 100 $s^{-1}$).

The copolymer compositions CP) are suitable both for the preparation of homogeneous-phase aqueous compositions, and also for the formulation of heterogeneous-phase compositions which additionally comprise at least one water-insoluble (hydrophobic) liquid or solid compound. "Homogeneous-phase compositions" have only a single phase irrespective of their number of constituents. "Heterogeneous-phase compositions" are disperse systems of two or more components that are immiscible with one another. These include solid/liquid, liquid/liquid and solid/liquid/liquid compositions, such as dispersions and emulsions, e.g. O/W and W/O formulations which have at least one of the oil and/or fat components described in more detail below and water as immiscible phases. In principle, the copolymers CP) can be used either in the water phase or else in the oil phase. In general, heterogeneous-phase liquid/liquid compositions comprise the copolymers CP) essentially in the water phase.

The copolymer compositions CP) according to the invention are very generally suitable for the preparation of active ingredient or effect substance compositions comprising A) at least one copolymer composition CP), as defined previously, B) at least one active ingredient or effect substance and C) optionally at least one further auxiliary different from A) and B).

Active ingredients for cosmetics (e.g. hair and skin cosmetics), medicaments, hygiene compositions, textile treatment compositions etc., i.e. substances which generally develop an effect even at low concentration, e.g. a cosmetic effect on skin and/or hair, a pharmacological effect in an organism, a cleaning and/or disinfecting effect, a modification of a textile substance, e.g. a crease-free finishing, and effect substances, which impart a certain property to living things or inanimate substrates, for example color pigments for make-up or emulsion paints, are often formulated and used in the form of aqueous active ingredient or effect substance compositions.

The active ingredient and effect substance compositions according to the invention comprise the polymer component A) preferably in an amount of from 0.01 to 50% by weight, particularly preferably 0.05 to 30% by weight, in particular 0.1 to 20% by weight, based on the total weight of the composition. Even in small use amounts, the copolymer compositions according to the invention advantageously exhibit good application-related properties, e.g. a good thickening effect. In a specific embodiment, the active ingredient and effect substance compositions according to the invention comprise polymer component A) in an amount of from 0.1 to 5% by weight, based on the total weight of the composition.

The components B) and C) are selected according to the desired field of use of the composition. Besides components which are typical for the field of use (e.g. certain pharmaceutical active ingredients), they are selected, for example, from carriers, excipients, emulsifiers, surfactants, preservatives, fragrances, thickeners different from component A), polymers, gel formers, dyes, pigments, photoprotective agents, consistency regulators, antioxidants, antifoams, antistats, resins, solvents, solubility promoters, neutralizing agents, stableizers, sterilizing agents, propellants, drying agents, opacifiers, etc.

The compositions preferably have a carrier component C) which is selected from water, hydrophilic carriers different from water and mixtures thereof.

Suitable hydrophilic carriers C) are, for example, mono-, di- or polyhydric alcohols having preferably 1 to 8 carbon atoms, such as ethanol, n-propanol, isopropanol, propylene glycol, glycerol, sorbitol, etc.

The compositions according to the invention can comprise, as active ingredient, e.g. as cosmetic and/or pharmaceutical active ingredient B) (and also optionally as auxiliary C)), at least one polymer which differs from the copolymer compositions CP) according to the invention. These include, quite generally, anionic, cationic, amphoteric and neutral polymers.

Examples of anionic polymers are copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luvimer® MAE), copolymers of N-tert-butylacrylamide, ethyl acrylate, acrylic acid (Ultrahold® 8, strong), copolymers of vinyl acetate, crotonic acid and optionally further vinyl esters (e.g. Luviset® grades), maleic anhydride copolymers, optionally reacted with alcohol, anionic polysiloxanes, e.g. carboxyfunctional ones, t-butyl acrylate, methacrylic acid (e.g. Luviscol® VBM), copolymers of acrylic acid and methacrylic acid with hydrophobic monomers, such as, for example, $C_4$-$C_{30}$-alkyl esters of (meth)acrylic acid, $C_4$-$C_{30}$-alkylvinyl esters, $C_4$-$C_{30}$-alkyl vinyl ethers and hyaluronic acid. One example of an anionic polymer is also the methyl methacrylate/methacrylic acid/acrylic acid/urethane acrylate copolymer available under the name Luviset® Shape (INCI name: Polyacrylate-22). Examples of anionic polymers are also vinyl acetate/crotonic acid copolymers, as are commercially available, for example, under the names Resyn® (National Starch) and Gafset® (GAF), and vinylpyrrolidone/vinyl acrylate copolymers available, for example, under the trade name Luviflex® (BASF). Further suitable polymers are the vinylpyrrolidone/acrylate terpolymer available under the name Luviflex® VBM-35 (BASF) and polyamides containing sodium sulfonate or polyesters containing sodium sulfonate. Also suitable are vinylpyrrolidone/ethyl methacrylate/methacrylic acid copolymers, as are sold by Stepan under the names Stepanhold-Extra and -R1, and the Carboset® grades from BF Goodrich.

Suitable cationic polymers are, for example, cationic polymers with the INCI name Polyquaternium, e.g. copolymers of vinylpyrrolidone/N-vinylimidazolium salts (Luviquat® FC, Luviquat® HM, Luviquat® MS, Luviset Clear®, Luviquat Supreme®, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamido copolymers (Polyquaternium-7) and chitosan. Suitable cationic (quaternized) polymers are also Merquat® (polymer based on dimethyldiallylammonium chloride), Gafquat® (quaternary polymers which are formed by the reaction of polyvinylpyrrolidone with quaternary ammonium compounds), polymer JR (hydroxyethylcellulose with cationic groups) and plant-based cationic polymers, e.g. guar polymers, such as the Jaguar® grades from Rhodia.

Very particularly suitable polymers are neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include, for example, Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviscol® Plus (BASF SE), or polyvinylpyrrolidone and copolymers thereof, in particular with vinyl esters, such as vinyl acetate, e.g. Luviscol® VA 37, VA 55, VA 64, VA 73 (BASF SE); polyamides, e.g. based on itaconic acid and aliphatic diamines, as are described, for example, in DE-A-43 33 238.

Suitable polymers are also amphoteric or zwitterionic polymers, such as the octylacrylamide/methyl methacrylate/tert-butylaminoethyl methacrylate/2-hydroxypropyl methacrylate copolymers available under the name Amphomer® (National Starch), and zwitterionic polymers, as are described, for example, in the German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacroylethylbetaine/methacrylate copolymers, which are commercially available under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or -dispersible polymers, e.g. polyether siloxanes, such as Tegopren® (Goldschmidt) or Belsil® (Wacker).

In one specific embodiment, the compositions according to the invention comprise at least one polymer which differs from the polymers present in the copolymer compositions CP) and which acts as thickener.

Suitable polymeric thickeners are, for example, optionally modified polymeric natural substances (carboxymethylcellulose and other cellulose ethers, hydroxyethyl- and -propylcellulose and the like) and also synthetic polymeric thickeners (polyacrylic and polymethacrylic compounds, vinyl polymers, polycarboxylic acids, polyethers, polyimines, polyamides). These include the in part already aforementioned polyacrylic and polymethacrylic compounds, for example the high molecular weight ones with a polyalkenyl polyether, in particular an allyl ether of sucrose, pentaerythritol or propylene, crosslinked homopolymers of acrylic acid (INCI name: carbomer). Such polyacrylic acids are available, inter alia, from BF Goodrich under the trade name Carbopol®, e.g. Carbopol 940 (molecular weight ca. 4 000 000), Carbopol 941 (molecular weight ca. 1 250 000) or Carbopol 934 (molecular weight ca. 3 000 000). They also include acrylic acid copolymers, which are available, for example, from Rohm & Haas under the trade names Aculyn® and Acusol®, for example the anionic, nonassociative polymers Aculyn 22, Aculyne 28, Aculyn 33 (crosslinked), Acusol 810, Acusol 823 and Acusol 830 (CAS 25852-37-3). Also specifically suitable are associative thickeners, e.g. based on modified polyurethanes (HEUR) or hydrophobically modified acrylic acid or methacrylic acid copolymers (HASE thickeners, High Alkali Swellable Emulsion).

The use amount of the additional thickeners is preferably in a range from 0.001 to 5% by weight, preferably 0.1 to 3%, based on the total weight of the composition.

Examples of effect substances which can be formulated as aqueous active ingredient composition according to the invention are dyes: e.g. the dyes described in DE-A 102 45 209, and also the compounds referred to according to the Color Index as disperse dyes and as solvent dyes, which are also referred to as dispersion dyes. A list of suitable dispersion dyes can be found, for example, in Ullmanns Enzyklopädie der technischen Chemie [Ullmann's encyclopedia of industrial chemistry], 4th edition, vol. 10, pp. 155-165 (see also vol. 7, p. 585ff—Anthraquinone dyes; vol. 8, p. 244ff—Azo dyes; vol. 9, p. 313ff—Quinophthalone dyes). Reference is hereby expressly made to this reference and the compounds cited therein. Dispersion dyes and solvent dyes suitable according to the invention comprise highly different dye classes with varying chromophores, for example anthraquinone dyes, monoazo and disazo dyes, quinophthalones, methine and azamethine dyes, naphthalimide dyes, naphthoquinone dyes and nitro dyes. Examples of dispersion dyes suitable according to the invention are the dispersion dyes of the following Color Index list: C. I. Disperse Yellow 1-228, C. I. Disperse Orange 1-148, C. I. Disperse Red 1-349, C. I. Disperse Violet 1-97, C. I. Disperse Blue 1-349, C. I. Disperse Green 1-9, C. I. Disperse Brown 1-21, C. I. Disperse Black 1-36. Examples of solvent dyes suitable according to the invention are the compounds of the following Color Index list: C. I. Solvent Yellow 2-191, C. I. Solvent Orange 1-113, C. I. Solvent Red 1-248, C. I. Solvent Violet 2-61, C. I. Solvent Blue 2-143, C. I. Solvent Green 1-35, C. I. Solvent Brown 1-63, C. I. Solvent Black 3-50. Dyes suitable according to the invention are also derivatives of naphthalene, of anthracene, of perylene, of terylene, of quarterylene, and also diketopyrrolopyrrole dyes, perinone dyes, coumarin dyes, isoindoline and isoindolinone dyes, porphyrin dyes, phthalocyanine and naphthalocyanine dyes.

Besides the aforementioned constituents, the active ingredient and effect substance compositions according to the invention can also comprise conventional surface-active substances and other additives. The surface-active substances include surfactants, dispersion auxiliaries and wetting agents. The other additives include, in particular, thickeners, antifoams, preservatives, antifreezes, stableizing agents, etc.

In principle, it is possible to use anionic, cationic, nonionic and amphoteric surfactants, with polymer surfactants and also surfactants with heteroatoms being included in the hydrophobic group.

The anionic surfactants include, for example, carboxylates, in particular alkali metal, alkaline earth metal and ammonium salts of fatty acids, e.g. potassium stearate, which are usually also referred to as soaps; acyl glutamates; sarcosinates, e.g. sodium lauroyl sarcosinate; taurates; methylcelluloses; alkyl phosphates, in particular mono- and diphosphoric acid alkyl esters; sulfates, in particular alkyl sulfates and alkyl ether sulfates; sulfonates, further alkyl- and alkylarylsulfonates, in particular alkali metal, alkaline earth metal and ammonium salts of arylsulfonic acids, and also alkyl-substituted arylsulfonic acids, alkylbenzenesulfonic acids, such as, for example, ligno- and phenolsulfonic acid, naphthalene- and dibutylnaphthalenesulfonic acids, or dodecylbenzenesulfonates, alkylnaphthalenesulfonates, alkyl methyl ester sulfonates, condensation products of sulfonated naphthalene and derivatives thereof with formaldehyde, condensation products of naphthalenesulfonic acids, phenolic and/or phenolsulfonic acids with formaldehyde or with formaldehyde and urea, mono- or dialkylsuccinic acid ester sulfonates; and protein hydrolyzates and lignosulfite waste liquors. The aforementioned sulfonic acids are advantageously used in the form of their neutral or optionally basic salts.

The cationic surfactants include, for example, quaternized ammonium compounds, in particular alkyltrimethylammonium and dialkyldimethylammonium halides and alkyl sulfates, and also pyridine and imidazoline derivatives, in particular alkylpyridinium halides.

The nonionic surfactants include, for example:
fatty alcohol polyoxyethylene esters, for example lauryl alcohol polyoxyethylene ether acetate,
alkyl polyoxyethylene and polyoxypropylene ethers, e.g. of isotridecyl alcohol and fatty alcohol polyoxyethylene ethers,
alkylaryl alcohol polyoxyethylene ethers, e.g. octylphenol polyoxyethylene ether,
alkoxylated animal and/or vegetable fats and/or oils, for example corn oil ethoxylates, castor oil ethoxylates, tallow fatty ethoxylates,
glycerol esters, such as, for example, glycerol monostearate,
fatty alcohol alkoxylates and oxo alcohol alkoxylates, in particular of the type RO—$(R_{18}O)_r(R_{19}O)_9R_{20}$ where $R_{18}$ and $R_{19}$ independently of one another $=C_2H_4$, $C_3H_6$, $C_4H_8$ and $R_{20}$=H or $C_1$-$C_{12}$-alkyl, R=$C_3$-$C_{30}$-alkyl or $C_6$-$C_{30}$-alkenyl, r and s independently of one another are 0 to 50, where both cannot be 0, such as isotridecyl alcohol and oleyl alcohol polyoxyethylene ether,
alkylphenol alkoxylates, such as, for example, ethoxylated isooctyl-, octyl- or nonylphenol, tributylphenol polyoxyethylene ether, fatty amine alkoxylates, fatty acid amide and fatty acid diethanolamide alkoxylates, in particular their ethoxylates, sugar surfactants, sorbitol esters, such as, for example, sorbitan fatty acid esters (sorbitan monooleate, sorbitan tristearate), polyoxyethylene sorbitan fatty acid esters, alkyl polyglycosides, N-alkylgluconamides, alkyl methyl sulfoxides, alkyl dimethylphosphine oxides, such as, for example, tetradecyl dimethylphosphine oxide.

The amphoteric surfactants include, for example, sulfobetaines, carboxybetaines and alkyldimethylamine oxides, e.g. tetradecyldimethylamine oxide.

Further surfactants which are to be specified here by way of example are perfluoro surfactants, silicone surfactants, phospholipids, such as, for example, lecithin or chemically modified lecithins, amino acid surfactants, e.g. N-lauroyl glutamate.

Unless specified, the alkyl chains in the surfactants listed above are linear or branched radicals having usually 8 to 20 carbon atoms.

The active ingredient or effect substance compositions according to the invention can comprise water-soluble salts as component B) and/or C), e.g. NaCl.

The active ingredient or effect substance compositions according to the invention can comprise organic solvents, oils and/or fats for some applications. Preference is given to those solvents, oils and/or fats which are environmentally compatible or biocompatible. These include, for example, paraffin oils, aromatic hydrocarbons and aromatic hydrocarbon mixtures, e.g. xylenes, Solvesso 100, 150 or 200, and the like, phenols and alkylphenols, e.g. phenol, hydroquinone, nonylphenol, etc.

ketones with more than 4 carbon atoms, such as cyclohexanone, isophorone, isophorone, acetophenone, acetonaphthone, alcohols with more than 4 carbon atoms, such as acetylated lanolin alcohol, cetyl alcohol, 1-decanol, 1-heptanol, 1-hexanol, isooctadecanol, isopropyl alcohol, oleyl alcohol, benzyl alcohol, carboxylic acid esters, e.g. dialkyl esters of adipic acid such as bis(2-ethylhexyl)adipate, dialkyl esters of phthalic acid such as bis(2-ethylhexyl)phthalate, alkyl esters of acetic acid (including branched alkyl groups) such as ethyl acetate and ethyl acetoacetate, stearates such as butyl stearate, glycerol monostearate, citrates such as acetyl tributyl citrate, also cetyl octanoate, methyl oleate, methyl p-hydroxybenzoate, methyl tetradecanoate, propyl p-hydroxybenzoate, methyl benzoate, lactic acid esters such as isopropyl lactate, butyl lactate and 2-ethylhexyl lactate, vegetable oils such as palm oil, rapeseed oil, castor oil and derivatives thereof, such as, for example, oxidized ones, coconut oil, cod-liver oil, corn oil, soybean oil, linseed oil, olive oil, peanut oil, dyer's safflower oil, sesame seed oil, grapefruit oil, basil oil, apricot oil, ginger oil, geranium oil, orange oil, rosemary oil, macadamia oil, onion oil, mandarin oil, pine oil, sunflower oil, hydrogenated vegetable oils such as hydrogenated palm oil, hydrogenated rapeseed oil, hydrogenated soybean oil, animal oils such as pork fat oil, fish oils, dialkylamides of medium- to long-chain fatty acids, e.g. hallcomides, and also vegetable oil esters, such as rapeseed oil methyl ester.

The copolymer compositions CP) can be used together with conventional thickeners.

These include the aforementioned polymers effective as thickeners. These further include polysaccharides and organic layer minerals such as Xanthan Gum® (Kelzan® from Kelco), Rhodopol®23 (Rhone Poulenc) or Veegum® (R. T. Vanderbilt) or Attaclay® (Engelhardt). Suitable thickeners are also organic natural thickeners (agar agar, carrageen, tragacanth, gum arabic, alginates, pectins, polyoses, guar flour, carob seed flour, starch, dextrins, gelatine, casein) and inorganic thickeners (polysilicic acids, clay minerals such as montmorillonites, zeolites, silicas). Further thickeners are the polysaccharides and heteropolysaccharides, in particular the polysaccharide gums, for example gum arabic, agar, alginates, carrageens and their salts, guar, guaran, tragacanth, gellan, ramsan, dextran or xanthan and their derivatives, e.g. propoxylated guar, and also their mixtures. Other polysaccharide thickeners are, for example, starches of highly diverse origin and starch derivatives, e.g. hydroxyethyl starch, starch phosphate esters or starch acetates, or carboxymethylcellulose or its sodium salt, methyl-, ethyl-, hydroxyethyl-, hydroxypropyl-, hydroxypropylmethyl- or hydroxyethylmethylcellulose or cellulose acetate. Thickeners which can be used are also sheet silicates. These include, for example, the magnesium or sodium-magnesium sheet silicates from Solvay Alkali available under the trade name Laponite®, and also the magnesium silicates from Süd-Chemie.

The use amount of the additional thickeners is preferably in a range from 0.001 to 10% by weight, preferably 0.1 to 5%, based on the total weight of the composition.

Suitable antifoams suitable for dispersions according to the invention are, for example, silicone emulsions (such as, for example, Silikon® SRE, Wacker or Rhodorsil® from Rhodia), long-chain alcohols, fatty acids, organofluorine compounds and mixtures thereof.

Bactericides can be added to stableize the compositions according to the invention against infestation of microorganisms. Suitable bactericides are, for example, Proxel® from ICI or Acticide® RS from Thor Chemie and Kathon® MK from Rohm & Haas.

Suitable antifreezes are organic polyols, e.g. ethylene glycol, propylene glycol or glycerol. These are usually used in amounts of not more than 10% by weight, based on the total weight of the active ingredient composition, so as not to exceed the desired content of volatile compounds. In one embodiment of the invention, the fraction of volatile organic compounds different therefrom is preferably not more than 1% by weight, in particular not more than 1000 ppm.

The active ingredient compositions according to the invention can optionally comprise 1 to 5% by weight of buffer, based on the total amount of the prepared formulation, for regulating the pH, the amount and type of buffer used being governed by the chemical properties of the active ingredient or active ingredients. Examples of buffers are alkali metal salts of weak inorganic or organic acids, such as, for example, phosphoric acid, boric acid, acetic acid, propionic acid, citric acid, fumaric acid, tartaric acid, oxalic acid or succinic acid.

In one particularly preferred embodiment, the copolymers according to the invention are used as component in a cosmetic composition. As described previously, they can serve here to modify the rheological properties of a cosmetic composition based on an aqueous medium.

The invention further provides a cosmetic composition comprising
A) at least one copolymer composition CP) obtainable by a process as defined above,
B) at least one cosmetically acceptable active ingredient and
C) optionally at least one further cosmetically acceptable auxiliary different from A) and B).

Preferably, component C) comprises at least one cosmetically or pharmaceutically acceptable carrier.

The carrier component C) is preferably selected from
i) water,
ii) water-miscible organic solvents, preferably $C_2$-$C_4$-alkanols, in particular ethanol,
iii) oils, fats, waxes,
iv) esters of $C_6$-$C_{30}$-monocarboxylic acids with mono-, di- or trihydric alcohols that are different from iii),
v) saturated acyclic and cyclic hydrocarbons,
vi) fatty acids,
vii) fatty alcohols,
viii) propellant gases,
and mixtures thereof.

Suitable hydrophilic components C) are the aforementioned organic solvents, oils and fats.

Specifically suitable cosmetically compatible oil and fat components C) are described in Karl-Heinz Schrader, Grundlagen and Rezepturen der Kosmetika [Fundamentals and formulations of cosmetics], 2nd edition, Verlag Hüthig, Heidelberg, pp. 319-355, to which reference is made here.

The cosmetic compositions according to the invention may be skin cosmetic, hair cosmetic, dermatological, hygiene or pharmaceutical compositions. On account of their thickening properties, the copolymer compositions CP) described above are suitable in particular as additives for hair and skin cosmetics. They are suitable specifically for the formulation of gels.

The compositions according to the invention are preferably in the form of a gel, foam, spray, salve, cream, emulsion, suspension, lotion, milk or paste. If desired, liposomes or microspheres can also be used.

The cosmetically active compositions according to the invention can additionally cornprise cosmetically and/or dermatologically active ingredients and effect substances and also auxiliaries. Of suitability in principle are the aforementioned active ingredients and effect substances B) and also auxiliaries C).

The cosmetic compositions according to the invention preferably comprise at least one copolymer composition CP) as defined above, at least one carrier C) as defined above and at least one constituent different therefrom which is preferably selected from cosmetically active ingredients, emulsifiers, surfactants, preservatives, perfume oils, additional thickeners, hair polymers, hair and skin conditioners, graft polymers, water-soluble or dispersible silicone-containing polymers, photoprotective agents, bleaches, gel formers, care agents, tinting agents, tanning agents, dyes, pigments, consistency regulators, humectants, refatting agents, collagen, protein hydrolyzates, lipids, antioxidants, antifoams, antistats, emollients and softeners.

In addition to the copolymer compositions CP), conventional thickeners suitable for use in cosmetic compositions are those mentioned above.

Suitable cosmetically and/or dermatologically active ingredients are, for example, skin and hair pigmentation agents, tanning agents, bleaches, keratin-hardening substances, antimicrobial active ingredients, photofilter active ingredients, repellent active ingredients, hyperemic substances, keratolytic and keratoplastic substances, antidandruff active ingredients, antiphlogistics, keratinizing substances, active ingredients which have an antioxidative effect and/or free-radical scavenging effect, skin-moisturizing or -humectant substances, refatting active ingredients, deodorizing active ingredients, sebostatic active ingredients, plant extracts, antierythimatous or antiallergic active ingredients and mixtures thereof.

Artificially skin-tanning active ingredients which are suitable for tanning of the skin without natural or artificial irradiation with UV rays are, for example, dihydroxyacetone, alloxan and walnut shell extract. Suitable keratin-hardening substances are generally active ingredients as are also used in antiperspirants, such as, for example, potassium aluminum sulfate, aluminum hydroxychloride, aluminum lactate, etc. Antimicrobial active ingredients are used in order to destroy microorganisms and/or to inhibit their growth and thus serve both as preservatives and also as deodorizing substance which reduces the development or the intensity of body odor. These include, for example, customary preservatives known to the person skilled in the art, such as p-hydroxybenzoic acid esters, imidazolidinylurea, formaldehyde, sorbic acid, benzoic acid, salicylic acid, etc. Deodorizing substances of this type are, for example, zinc ricinoleate, triclosan, undecylenic acid alkylolamides, triethyl citrate, chlorhexidine etc. Suitable photofilter active ingredients are substances which absorb UV rays in the UVB and/or UV-A region. Suitable UV filters are those specified above. Also suitable are p-aminobenzoic acid esters, cinnamic acid esters, benzophenones, camphor derivatives and pigments which stop UV rays, such as titanium dioxide, talc and zinc oxide. Suitable repellent active ingredients are compounds which are able to deter or drive away certain animals, in particular insects, from people. These include, for example, 2-ethyl-1,3-hexanediol, N,N-diethyl-m-toluamide etc. Suitable hyperemic substances, which stimulate blood flow through the skin, are, for example, essential oils, such as dwarf-pine, lavender, rosemary, juniperberry, horse chestnut extract, birch leaf extract, hay flower extract, ethyl acetate, camphor, menthol, peppermint oil, rosemary extract, eucalyptus oil, etc. Suitable keratolytic and keratoplastic substances are, for example, salicylic acid, calcium thioglycolate, thioglycolic acid and its salts, sulfur, etc. Suitable antidandruff active ingredients are, for example, sulfur, sulfur polyethylene glycol sorbitan monooleate, sulfur ricinol polyethoxylate, zinc pyrithione, aluminum pyrithione, etc. Suitable antiphlogistics, which counteract skin irritations, are, for example, allantoin, bisabolol, dragosantol, camille extract, panthenol, etc.

The cosmetic compositions according to the invention can comprise, as cosmetic active ingredient (and also optionally as auxiliary), at least one cosmetically or pharmaceutically acceptable polymer which differs from the copolymers CP) according to the invention. These include, very generally, anionic, cationic, amphoteric and neutral polymers. Reference is made here to the aforementioned polymers in their entirety.

According to a preferred embodiment, the compositions according to the invention are a skin cleaning composition.

Preferred skin cleaning compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, shower and bath preparations, such as washing lotions, shower baths and shower gels, foam baths, oil baths and scrub preparations, shaving foams, shaving lotions and shaving creams.

According to a further preferred embodiment, the compositions according to the invention are cosmetic compositions for the care and protection of the skin, nail care compositions or preparations for decorative cosmetics.

Suitable skin cosmetic compositions are, for example, face toners, face masks, deodorants and other cosmetic lotions. Compositions for use in decorative cosmetics include, for example, concealing sticks, stage make-up, mascara and eyeshadows, lipsticks, kohl pencils, eyeliners, blushers, powders and eyebrow pencils.

Moreover, the copolymer compositions CP) can be used in nose strips for pore cleansing, in antiacne compositions, repellents, shaving compositions, hair removal compositions, intimate care compositions, foot care compositions and also in baby care.

The skin care compositions according to the invention are in particular W/O or O/W skin creams, day and night creams, eye creams, face creams, antiwrinkle creams, moisturizing creams, bleaching creams, vitamin creams, skin lotions, care lotions and moisturizing lotions.

Skin cosmetic and dermatological compositions based on the above-described copolymers CP) exhibit advantageous effects. The polymers can contribute, inter glia, to the moisture retention and conditioning of the skin and to improving the skin feel. By adding the polymers according to the invention, a considerable improvement in skin compatibility can be achieved in certain formulations.

Skin cosmetic and dermatological compositions comprise preferably at least one copolymer composition CP) in a fraction of from about 0.001 to 30% by weight, preferably 0.01 to 20% by weight, very particularly preferably 0.1 to 12% by weight, based on the total weight of the composition.

Depending on the field of use, the compositions according to the invention can be applied in a form suitable for skin care, such as, for example, as cream, foam, gel, stick, mousse, milk, spray (pump spray or propellant-containing spray) or lotion.

Besides the copolymer compositions CP) and suitable carriers, the skin cosmetic preparations can also comprise further active ingredients and auxiliaries customary in skin cosmetics, as described above. These include preferably emulsifiers, preservatives, perfume oils, cosmetic active ingredients such as phytantriol, vitamin A, E and C, retinol, bisabolol, panthenol, photoprotective agents, bleaches, tanning agents, collagen, protein hydrolyzates, stableizers, pH regulators, dyes, salts, thickeners, gel formers, consistency regulators, silicones, humectants, refatting agents and further customary additives.

Preferred oil and fat components of the skin cosmetic and dermatological compositions are the aforementioned mineral and synthetic oils, such as, for example, paraffins, silk cone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof.

The polymers according to the invention can also be mixed with conventional polymers, as described above, if specific properties are to be set.

To set certain properties, such as, for example, improving the feel to the touch, the spreading behavior, the water resistance and/or the binding of active ingredients and auxiliaries, such as pigments, the skin cosmetic and dermatological preparations can additionally also comprise conditioning substances based on silicone compounds.

Suitable silicone compounds are, for example, polyalkylsiloxanes, polyarylsiloxanes, polyarylalkylsiloxanes, polyether siloxanes or silicone resins.

The preparation of the cosmetic or dermatological preparations takes place in accordance with customary processes known to the person skilled in the art.

The cosmetic and dermatological compositions are preferably in the form of emulsions, in particular as water-in-oil (W/O) or oil-in-water (O/W) emulsions. However, it is also possible to select other types of formulation, for example hydrodispersions, gels, oils, oleogels, multiple emulsions, for example in the form of W/O/W or O/W/O emulsions, anhydrous salves or salve bases, etc.

The preparation of emulsions takes place by known methods. Besides at least one copolymer composition CP), the emulsions generally comprise customary constituents, such as fatty alcohols, fatty acid esters and in particular fatty acid triglycerides, fatty acids, lanolin and derivatives thereof, natural or synthetic oils or waxes and emulsifiers in the presence of water. The selection of the additives specific to the type of emulsion and the preparation of suitable emulsions is described, for example, in Schrader, Grundlagen and Rezepturen der Kosmetika [Fundamentals and formulations of cosmetics], Hüthig Buch Verlag, Heidelberg, 2nd edition, 1989, third part, to which reference is hereby expressly made.

A suitable emulsion, e.g. for a skin cream etc., generally comprises an aqueous phase emulsified by means of a suitable emulsifier system in an oil or fat phase. A copolymer composition CP) can be used to provide the aqueous phase.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils whose distillation start-point under atmospheric pressure is ca. 250° C. and whose distillation end point is 410° C., such as, for example, vaseline oil; esters of saturated or unsaturated fatty acids, such as alkyl myristates, e.g. isopropyl, butyl or cetyl myristate, hexadecyl stearate, ethyl or isopropyl palmitate, octanoic or decanoic acid triglycerides and cetyl ricinoleate.

The fatty phase may also comprise silicone oils that are soluble in other oils, such as dimethylpolysiloxane, methylphenylpolysiloxane and the silicone glycol copolymer, fatty acids and fatty alcohols.

Besides the copolymer compositions CP), waxes can also be used, such as, for example, carnauba wax, candililla wax, beeswax, microcrystalline wax, ozokerite wax and Ca, Mg and Al oleates, myristates, linoleates and stearates.

Furthermore, an emulsion according to the invention may be present as O/W emulsion. An emulsion of this type usually comprises an oil phase, emulsifiers which stableize the oil phase in the water phase, and an aqueous phase which is usually present in thickened form. Suitable emulsifiers are preferably O/W emulsifiers, such as polyglycerol esters, sorbitan esters or partially esterified glycerides.

According to a further preferred embodiment, the compositions according to the invention are a shower gel, a shampoo formulation or a bath preparation.

Such formulations comprise at least one copolymer composition CP) and usually anionic surfactants as base surfactants and amphoteric and/or nonionic surfactants as cosurfactants. Further suitable active ingredients and/or auxiliaries are generally selected from lipids, perfume oils, dyes, organic acids, preservatives and antioxidants and also thickeners/gel formers, skin conditioners and humectants.

These formulations preferably comprise 2 to 50% by weight, preferably 5 to 40% by weight, particularly preferably 8 to 30% by weight, of surfactants, based on the total weight of the formulation.

All anionic, neutral, amphoteric or cationic surfactants customarily used in body cleaning compositions can be used in the washing, shower and bath preparations.

Suitable surfactants are those specified above.

Furthermore, the shower gel/shampoo formulations can comprise additional thickeners, such as, for example, sodium chloride, PEG-55, propylene glycol oleate, PEG-120 methylglucose dioleate and others, and also preservatives, further active ingredients and auxiliaries and water.

According to a further preferred embodiment, the compositions according to the invention are a hair treatment composition.

Hair treatment compositions according to the invention preferably comprise at least one copolymer composition CP) in an amount in the range from about 0.1 to 30% by weight, preferably 0.5 to 20% by weight, based on the total weight of the composition.

The hair treatment compositions according to the invention are preferably present in the form of a setting foam, hair mousse, hair gel, hair shampoo, hairspray, hair foam, end fluid, neutralizer for permanent waves or "hot-oil treatments". Depending on the field of use, the hair cosmetic preparations can be applied as (aerosol) spray, (aerosol) foam, gel, gel spray, cream, lotion or wax. Hairsprays here comprise both aerosol sprays and also pump sprays without propellant gas. Hair foams comprise both aerosol foams and also pump foams without propellant gas. Hairsprays and hair foams comprise preferably predominantly or exclusively water-soluble or water-dispersible components. If the compounds used in the hairsprays and hair foams according to the invention are water-dispersible, they can be applied in the form of aqueous microdispersions having particle diameters of usually 1 to 350 nm, preferably 1 to 250 nm. The solids contents of these preparations are usually in a range from about 0.5 to 20% by weight. These microdispersions generally require no emulsifiers or surfactants for their stableization.

In a preferred embodiment, the hair cosmetic formulations according to the invention comprise
a) 0.05 to 5% by weight, preferably 0.1 to 3% by weight, of at least one copolymer composition CP),
b) 20 to 99.95% by weight of water and/or alcohol,
c) 0 to 50% by weight of at least one propellant gas,
d) 0 to 5% by weight of at least one emulsifier,
e) 0 to 3% by weight of at least one thickener different from a), and
f) 0 to 20% by weight, preferably 0.1 to 10% by weight, of at least one water-soluble or water-dispersible polymer different from a) to e) and g),
g) 0 to 45% by weight, preferably 0.05 to 25% by weight, of further constituents,
where the components a) to g) add up to 100% by weight.

Alcohol is to be understood as meaning all alcohols customary in cosmetics, e.g. ethanol, isopropanol, n-propanol.

Further constituents are to be understood as meaning the additives customary in cosmetics, for example propellants, antifoams, interface-active compounds, i.e. surfactants, emulsifiers, foam formers and solubilizers. The interface-active compounds used may be anionic, cationic, amphoteric or neutral. Further customary constituents may also be, for example, preservatives, perfume oils, opacifiers, active ingredients, UV filters, care substances such as panthenol, collagen, vitamins, protein hydrolyzates, alpha- and beta-hydroxycarboxylic acids, stableizers, pH regulators, dyes, viscosity regulators, gel formers, salts, humectants, refatting agents, complexing agents and further customary additives.

Furthermore, these include all styling and conditioning polymers known in cosmetics which can be used in combination with the polymers according to the invention if very specific properties are to be set.

Suitable conventional hair cosmetic polymers are, for example, the aforementioned cationic, anionic, neutral, nonionic and amphoteric polymers, to which reference is made here.

To set certain properties, the preparations can additionally also comprise conditioning substances based on silicone compounds. Suitable silicone compounds are, for example, polyalkylsiloxanes, polyarylsiloxanes, polyarylalkylsiloxanes, polyether siloxanes, silicone resins or dimethicone copolyols (CTFA) and amino-functional silicone compounds such as amodimethicones (CTFA).

The copolymer compositions according to the invention are suitable in particular as thickeners in hair styling preparations, in particular hair foams and hair gels.

Emulsifiers which can be used are all emulsifiers that are customarily used in hair foams. Suitable emulsifiers may be nonionic, cationic and anionic or amphoteric.

A preparation suitable according to the invention for styling gels can, for example, have the following composition:
a) 0.1 to 5% by weight of at least one copolymer composition CP),
b) 0 to 5% by weight of at least one cosmetically acceptable water-soluble or water-dispersible hair setting polymer different from CP),
c) 80 to 99.85% by weight of water and/or alcohol,
d) 0 to 1% by weight of a gel former different from CP),
e) 0 to 20% by weight of further constituents.

Additional gel formers which can be used are all gel formers customary in cosmetics. Reference is made in this regard to the aforementioned conventional thickeners.

The copolymer compositions CP) according to the invention are also suitable for shampoo formulations, which additionally comprise customary surfactants.

In the shampoo formulations, to achieve certain effects, customary conditioners can be used in combination with the copolymer compositions CP). These include, for example, the aforementioned cationic polymers with the INCI name Polyquaternium, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamide copolymers (Polyquaternium-7). In addition, protein hydrolyzates can be used, as can conditioning substances based on silicone compounds, for example polyalkylsiloxanes, polyarylsiloxanes, polyarylalkylsiloxanes, polyether siloxanes or silicone resins. Further suitable silicone compounds are dimethicone copolyols (CTFA) and amino-functional silicone compounds such as amodimethicones (CTFA). In addition, cationic guar derivatives such as guar hydroxypropyltrimonium chloride (INCI) can be used.

The copolymer compositions CP) to be used according to the invention are likewise suitable for the use for modifying the rheological properties in pharmaceutical preparations of any type.

The invention therefore further provides a pharmaceutical composition comprising
A) at least one copolymer composition CP) as defined above,
B) at least one pharmaceutically acceptable active ingredient and
C) optionally at least one further pharmaceutically acceptable auxiliary different from A) and B).

The formulation base of the pharmaceutical compositions according to the invention preferably comprises pharmaceutically acceptable auxiliaries. Of pharmaceutical acceptability are the auxiliaries that are known for use in the field of pharmacy, food technology and related fields, in particular the auxiliaries listed in relevant pharmacopoeia (e.g. DAB, Ph. Eur., BP, NF), as well as other auxiliaries whose properties do not preclude a physiological use.

Suitable auxiliaries may be: glidants, wetting agents, emulsifying and suspending agents, preservatives, antioxidants, antiirritatives, chelating agents, emulsion stableizers, film formers, gel formers, odor masking agents, resins, hydrocolloids, solvents, solubility promoters, neutralizing agents, permeation accelerators, pigments, quaternary ammonium compounds, refatting and superfatting agents, salve, cream or oil bases, silicone derivatives, stableizers, sterilizing agents, propellants, drying agents, opacifiers, additional thickeners, waxes, softeners, white oils. An embodiment in this regard is based on specialist knowledge, as represented, for example, in Fiedler, H. P. Lexikon der Hilfsstoffe für Pharmazie, Kosmetik and angrenzende Gebiete [Lexicon of the auxiliaries for pharmacy, cosmetics and related fields], 4th edition, Aulendorf: ECV-Editio-Kantor-Verlag, 1996.

To prepare pharmaceutical compositions according to the invention, the active ingredients can be mixed or diluted with a suitable auxiliary (excipient). Excipients may be solid, semisolid or liquid materials which can serve as a vehicle, carrier or medium for the active ingredient. The admixing of further auxiliaries takes place if desired in the manner known to the person skilled in the art. In particular, these are aqueous solutions or solubilizates for oral or parenteral application. Furthermore, the copolymers to be used according to the invention are also suitable for use in oral administration forms such as tablets, capsules, powders, solutions. Here, they can provide the sparingly soluble medicament with increased bioavailability. In the case of parenteral application, emulsions, for example fatty emulsions, can also be used besides solubilizates.

Pharmaceutical formulations of the aforementioned type can be obtained by processing the copolymer compositions CP) to be used according to the invention with pharmaceutical active ingredients by conventional methods and using known and new active ingredients.

The use according to the invention can additionally comprise pharmaceutical auxiliaries and/or diluents. Cosolvents, stableizers, preservatives are particularly listed as auxiliaries.

The pharmaceutical active ingredients used are water-soluble substances or else insoluble or poorly soluble substances. According to DAB 9 (German pharmacopoeia), the grading of the solubility of pharmaceutical active ingredients is as follows: poorly soluble (soluble in 30 to 100 parts of solvent); sparingly soluble (soluble in 100 to 1000 parts of solvent); virtually insoluble (soluble in more than 10 000 parts of solvent). The active ingredients can come from any area of indication.

The content of copolymer CP) in the pharmaceutical compositions is, depending on the active ingredient, in the range from 0.01 to 50% by weight, preferably 0.1 to 40% by weight, particularly preferably 1 to 30% by weight, based on the total weight of the composition.

Of suitability for preparing the pharmaceutical compositions according to the invention are in principle all pharmaceutical active ingredients and prodrugs. These include benzodiazepines, antihypertensives, vitamins, cytostatics—in particular taxol, anesthetics, neuroleptics, antidepressants, antibiotics, antimycotics, fungicides, chemotherapeutics, urologics, platelet aggregation inhibitors, sulfonamides, spasmolytics, hormones, immunoglobulins, sera, thyroid therapeutics, psychopharmaceuticals, antiparkinson agents and other antihyperkinetics, ophthalmics, neuropathy products, calcium metabolism regulators, muscle relaxants, narcotics, lipid-lowering agents, liver therapeutics, coronary agents, cardiac agents, immunotherapeutics, regulatory peptides and their inhibitors, hypnotics, sedatives, gynecologicals, antigout agents, fibrinolytics, enzyme products and transport proteins, enzyme inhibitors, emetics, perfusion promoters, diuretics, diagnostics, corticoids, cholinergics, biliary therapeutics, antiasthmatics, broncholytics, beta-receptor blockers, calcium antagonists, ACE inhibitors, arteriosclerosis remedies, antiphlogistics, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, and weight-reduction agents. Examples of suitable pharmaceutical active ingredients are the active ingredients specified in particular in paragraphs 0105 to 0131 of US 2003/0157170.

Besides the use in cosmetics and in pharmacy, the copolymer compositions CP) to be used according to the invention are also suitable in the food sector for modifying rheological properties. The invention therefore also provides food preparations which comprise at least one of the copolymer compositions CP) to be used according to the invention. Within the context of the present invention, food preparations are also to be understood as meaning food supplements, such as, for example, preparations comprising food dyes and dietetic foods. Moreover, the specified copolymer compositions CP) are also suitable for modifying the rheological properties of feed additives for animal nutrition.

Moreover, the copolymer compositions CP) are suitable for preparing aqueous preparations of food supplements, such as water-insoluble vitamins and provitamins such as vitamin A, vitamin A acetate, vitamin D, vitamin E, tocopherol derivatives such as tocopherol acetate and vitamin K.

The invention further provides the use of a copolymer composition CP), as defined above, as auxiliary in pharmacy, preferably as or in (a) coating composition(s) for solid medicament forms, for modifying rheological properties, as surface-active compound, as or in (an) adhesive(s) and as or in (a) coating composition(s) for the textile, paper, printing and leather industry.

The invention is illustrated in more detail by reference to the following nonlimiting examples.

EXAMPLES

I. Preparation of the Auxiliary Composition H1

I.1 General Procedure for the Preparation of the Urethane Compound H1

In a 4-neck flask which was equipped with stirrer, dropping funnel, thermometer, reflux condenser and a device for working under nitrogen, long-chain diol, neopentyl glycol, N-methyldiethanolamine and polyethylene glycol monomethyl ether, i.e. the components a), b), c) and d) in the amounts stated in table 2 and 0.2% by weight (based on all of the components including the solvent ethyl acetate) of 1,4-diazabicyclo[2.2.2]octane (DABCO) in ethyl acetate (solids content of the reaction mixture about 70%; for ca. 400 g of product about 100 g of ethyl acetate) were introduced as initial charge and dissolved with stirring and heating to a temperature from 60 to 65° C. Then, over the course of 30 minutes, hexamethylene diisocyanate (component e1) in the amounts stated in table 2 was metered in such that the reaction temperature remained below 80° C. Then, the reaction mixture was afterstirred for 30 minutes at 75 to 80° C. until the NCO content of the mixture remained virtually constant. Then, 0.2% by weight, based on all of the components including the solvent ethyl acetate, of DABCO was added, and isophorone diisocyanate (component e2) was metered in in the amount stated in table 2 at an internal temperature below 85° C. over the course of 30 minutes. The reaction mixture was afterstirred for 4 to 8 hours at 82±3° C. until the NCO content remained constant. The reaction mixture was then left to cool and diluted with ethyl acetate to a solids content of 50%. Component f) was then metered in such that the reaction temperature remained below 40° C. The mixture was afterstirred for 1 hour at 40 to 50° C. The reaction product was diluted again with ethyl acetate.

TABLE 2

| Component | a) long-chain diol | b) short-chain diol | c) NMEDA | d) MPEG-OH | e1): HDI | e2): IPDI | f) chain extender or stopper |
|---|---|---|---|---|---|---|---|
| H1-1 | PTHF 2 mol | NPG 1.5 mol | 0.5 mol | Pluriol A500E 1.5 mol | 2 mol | 3 mol | A Si 2322 0.054 mol |
| H1-2 | PTHF 2 mol | NPG 1.5 mol | 0.5 mol | Pluriol A500E 1.5 mol | 2 mol | 3 mol | Isophoronediamine 0.054 mol |
| H1-3 | VP 9186 1 mol | NPG 1 mol | — | Pluriol A500E 1.5 mol | 1.5 mol | 1.5 mol | 1,5-pentanediamine 0.054 mol |
| H1-4 | VP 9186 1 mol | NPG 1 mol | — | Pluriol A500E 1.5 mol | 1.5 mol | 1.5 mol | Isophoronediamine 0.054 mol |
| H1-5 | PTHF 2 mol | NPG 2 mol | — | Pluriol A500E 1.5 mol | 1 mol | 4 mol | Hexamethylenediamine 0.25 mol |
| H1-6 | PTHF (0.8 mol) + VP 9186 (0.8 mol) | NPG 0.4 mol | 0.25 mol | Pluriol A500E 1.5 mol | 1.5 mol | 1.5 mol | — |
| H1-7 | T 22/98/99 1.6 mol | NPG 0.4 mol | 0.25 mol | Pluriol A1000E 1.5 mol | 1.5 mol | 1.5 mol | — |
| H1-8 | T 22/98/99 1 mol | — | — | Pluriol A1000E 1.5 mol | — | 2.0 mol | Isophoronediamine 0.25 mol |
| H1-9 | — | — | — | Pluriol A1000E (0.5 mol) + Pluriol A2000E (0.5 mol) | — | 1.05 mol | Kerocom PIBA 1 mol |
| H1-10 | PTHF 2 mol | NPG 1.7 mol | 0.3 mol | Pluriol A1000E 1.5 mol | 2.5 mol | 2.5 mol | Isphoronediamine 0.25 mol |
| H1-11 | PTHF 2 mol | NPG 1.7 mol | 0.3 mol | Pluriol A1000E 1.5 mol | 2.5 mol | 2.5 mol | Kerocom PIBA 1 mol |
| H1-12 | PTHF 2 mol | NPG 2.0 mol | — | Pluriol A1000E 1.5 mol | 2.5 mol | 2.5 mol | Isophoronediamine 0.25 mol |
| H1-13 | PTHF 2 mol | NPG 2.0 mol | — | Pluriol A1000E 1.5 mol | 2.5 mol | 2.5 mol | 3-Aminopropylimidazole |

| | |
|---|---|
| PTHF | Polytetrahydrofuran, $M_n$ about 1000 g/mol |
| VP 9186 | Lupraphen ® VP 9186 from BASF SE (polyesterdiol of adipic acid and 1,4-butanediol), $M_n$ about 2000 g/mol |
| T 22/98/99 | Polyesterdiol of isophthalic acid, 1,6-hexanediol and neopentyl glycol, $M_n$ about 2000 g/mol |
| NPG | Neopentyl glycol |
| NMEDA | N-Methyldiethanolamine |
| MPEG-OH | Polyethylene glycol monomethyl ether |
| Pluriol ® A500E | Polyethylene glycol monomethyl ether, $M_n$ 500 g/mol, BASF SE |
| Pluriol ® A1000E | Polyethylene glycol monomethyl ether, $M_n$ about 1000 g/mol, BASF SE |
| Pluriol ® A2000E | Polyethylene glycol monomethyl ether, $M_n$ about 2000 g/mol, BASF SE |
| HDI | Hexamethylene diisocyanate |
| IPDI | Isophorone diisocyanate |
| A Si 2322 | Tegomer ® A Si 2322, Goldschmidt, α,ω-amino-functional poly-siloxane |
| Kerocom ® PIBA | Polyisobutenamine, $M_n$ about 1000 g/mol, BASF SE |

1.2 Polyisobutenyl Alcohol Alkoxylates and Polyisobutenyl Amine Alkoxylates

General method A:

Reaction of Polyisobutenylsuccinic Anhydride with Methylpolyethylene Glycol or Polyethylene Glycol to Give the Corresponding Half-Ester In a 4 l three-neck flask with nitrogen feed, 1 mol of PIBSA1000 and polyether in the amount stated in table 3, and ethyl acetate (about 20% by weight, based on the total mixture) were weighed in and heated at 50° C. for 1 hour. The mixture was then heated to 70 to 80° C. During the reaction, partially volatile constituents distilled over. For completeness, towards the end of the reaction, at a temperature of from 80 to 100° C., the pressure was reduced to 20 hPa. The mixture was then cooled to room temperature.

General Method B:

Reaction of Polyisobutenylsuccinic Anhydride with Alkanolamine

In a four-neck flask, 1 mol of PIBSA$_{1000}$ in ethyl acetate (30% by weight, based on all components) was weighed in and then, at 30° C., the alkanolamine as in table 3 was added dropwise. The mixture was heated to 40 to 50° C. and the reaction mixture was held for 1 h at this temperature. The mixture was then heated to 70 to 80° C. During the reaction, partially volatile constituents distilled over. For completeness, towards the end of the reaction, at a temperature of from 80 to 100° C., the pressure was reduced to 20 hPa. The total distillation time was ca. 1 h. The mixture was then cooled to room temperature and ethyl acetate was added such that the solids content of the reaction mixture was 40%.

General Method C:

Reaction of Urethane Prepolymers with Polyisobutyleneamine

In a 4-neck flask which was equipped with stirrer, dropping funnel, thermometer, reflux condenser and a device for working under nitrogen, the polyether and optionally neopentyl glycol in the amounts stated in table 3 and 0.2% by weight (based on all of the components including the solvent ethyl acetate) of DABCO in ethyl acetate (solids content of the reaction mixture about 70%) were weighed in. Then, over the course of 30 minutes, 1 mol of isophorone diisocyanate was metered in such that the reaction temperature remained below 80° C. The reaction mixture was then afterstirred for 2 to 4 hours at 75 to 80° C. until the NCO content of the mixture remained virtually constant. The reaction mixture was diluted with ethyl acetate to a solids content of from 30 to 50%. 1 mol of polyisobutyleneamine was then added such that the reaction temperature was in the range from 40 to 80° C. For completion of the reaction, the mixture was afterstirred for 1 hour at 40 to 80° C.

TABLE 3

| | PIBSA$_{1000}$ | PIB$_{1000}$-NH$_2$ | Polyether | Alkanolamine | NPG | IPDI | Method |
|---|---|---|---|---|---|---|---|
| H1-14 | 1 mol | — | MPEG$_{1000}$ 1 mol | — | — | — | A |
| H1-15 | 1 mol | — | MPEG$_{500}$ 1 mol | — | — | — | A |
| H1-16 | 1 mol | — | MPEG$_{350}$ 1 mol | — | — | — | A |
| H1-17 | 1 mol | — | PEG$_{200}$ 2 mol | — | — | — | A |
| H1-18 | 1 mol | — | — | AE-Gly 1 mol | — | — | B |
| H1-19 | 1 mol | — | — | DEA 1 mol | — | — | B |
| H1-20 | — | 1 mol | MPEG$_{1000}$ 1 mol | — | — | 1 mol | C |
| H1-21 | — | 1 mol | MPEG$_{500}$ 1 mol | — | — | 1 mol | C |
| H1-22 | — | 1 mol | MPEG$_{350}$ 1 mol | — | — | 1 mol | C |
| H1-23 | — | 1 mol | PEG$_{200}$ 2 mol | — | — | 1 mol | C* |
| H1-24 | — | 1 mol | MPEG$_{500}$ 1 mol | — | 1 mol | 2 mol | C |

*Reaction is varied: first reaction of PIB amine with IPDI, then with PEG$_{200}$ PIBSA$_{1000}$ — Polyisobutenylsuccinic anhydride, M$_n$ about 1000 g/mol
PIB$_{1000}$-NH$_2$ — Polyisobutyleneamine, M$_n$ about 1000 g/mol
MPEG$_{300, 500, 1000}$ — Methylpolyethylene glycol, M$_n$ 300, 500 or 1000 g/mol
PEG$_{200}$ — Polyethylene glycol, M$_n$ 200 g/mol
AE-GLy — 2-(2-Aminoethoxy)ethanol
DEA — Diethanolamine
NPG — Neopentyl glycol
IPDI — Isophorone diisocyanate II Synthesis of Acrylic-Acid-Containing Polymers General Process
(Example 6 in Table 4)

| | | |
|---|---|---|
| Initial charge | Ethyl acetate | 204.55 g |
| | Cyclohexane | 180.85 g |
| | H1-26 | 11.92 g |
| Feed 1 | Ethyl acetate | 109.80 g |
| | Cyclohexane | 97.38 g |
| | Acrylic acid | 592.00 g |
| | Pentaerythritol triallyl ether, 70% | 4.24 g |
| | NH$_4$CO$_3$ | 17.76 g |
| Feed 2 | Ethyl acetate | 170.91 g |
| | Cyclohexane | 151.55 g |
| | Wako ® V65 | 0.12 g |
| | tert-Butyl peroctoate, 98% strength | 1.08 g |
| Feed 3 | Ethyl acetate | 446.66 g |
| | Cyclohexane | 396.10 g |

Wako ® V65 Azobis(2,4-dimethylvaleronitrile), available from Wako Chemicals

Reaction Procedure:

In a pressurized apparatus fitted with reflux condenser, internal thermometer and three separate feed devices, the initial charge was weighed in, pressurized three times with 2 bar of nitrogen and heated to ca. 70° C. with stirring. Feed 1 and Feed 2 were metered in at 70° C., Feed 1 being metered in over the course of 3 hours and Feed 2 being metered in over the course of 5 hours. 1 hour after the start of Feed 1, Feed 3 was metered in over the course of 3 hours. When the addition of Feed 2 was complete, the reaction mixture was heated to 75° C. and left to afterpolymerize for 9 hours. The resulting product was filtered and dried in a drying cabinet.

The copolymer compositions of Examples 1 to 5, 10, 11 and 12 in table 4 were prepared in an analogous manner. The copolymer compositions of Examples 7, 8 and 9 were prepared in an analogous manner, where in Example 7 Feed 1 additionally comprised the amount of vinylpyrrolidone stated in table 4, in Example 8 additionally comprised the amount of methacrylamide stated in table 4 and in Example 9 additionally comprised the amounts of vinylpyrrolidone and vinylimidazole stated in table 4.

The copolymer compositions obtained by the above process are listed in table 4. The quantitative data in table 4 are (unless stated otherwise) in % by weight, based on the unsaturated monomers used for the polymerization. Likewise listed are comparison compositions VB1, VB2 and VB3, which were prepared in an analogous manner.

TABLE 4

| Example | AA | VP | MAM | PETAE | VI | H1)** | H2)*** $NH_4HCO_3$ [%] |
|---|---|---|---|---|---|---|---|
| VB1 | 99.5 | — | — | 0.5 | — | — | — |
| VB2 | 99.5 | — | — | 0.5 | — | — | 3% |
| VB3 | 99.5 | — | — | 0.5 | — | H1-15 2% | — |
| 1 | 99.5 | — | — | 0.5 | — | H1-15 2% | 1% |
| 2 | 99.5 | — | — | 0.5 | — | H1-15 2% | 2% |
| 3 | 99.5 | — | — | 0.5 | — | H1-15 2% | 3% |
| 4 | 99.5 | — | — | 0.5 | — | H1-15 2% | 6% |
| 5 | 99.5 | — | — | 0.5 | — | H1-25 2% | 3% |
| 6 | 99.5 | — | — | 0.5 | — | H1-26 2% | 3% |
| 7 | 84.5 | 15 | — | 0.5 | — | H1-26 2% | 3% |
| 8 | 84.5 | — | 15 | 0.5 | — | H1-26 2% | 3% |
| 9 | 84.5 | 13 | — | 0.5 | 2 | H1-26 2% | 3% |
| 10 | 99.5 | — | — | 0.5 | — | H1-11 2% | 2% |
| 11 | 99.5 | — | — | 0.5 | — | H1-18 2% | 2% |
| 12 | 99.5 | — | — | 0.5 | — | H1-21 2% | 2% |

AA: Acrylic acid
VP: Vinylpyrrolidone
VI: Vinylimidazole
MAM: Methacrylamide
PETAE Pentaerythritol triallyl ether
H1-15 PIBSA$_{1000}$/Pluriol A500E
H1-25: Belsil DMC 6031 (Wacker)
H1-26: ABIL Soft AF 100 (Evonik)
)**% data: based on 100% monomers (inclusive of crosslinkers)
)***% data: use of $NH_4HCO_3$ based on acrylic acid Table 5 lists details of product properties of the copolymer compositions according to the invention and also of the comparison copolymer compositions VB1, VB2 and VB3. A scale from 1 to 5 was taken as a basis.

TABLE 5

| Example | Redispersed rate*) grade | Stability/observation*) |
|---|---|---|
| VB1 | 5 | 0/insoluble mass |
| VB2 | 4 | +++/high viscosity |
| VB3 | 2 | 0/sedimented immediately |
| 1 | 2+ | +/−; sedimented after ca. 20 min |
| 2 | 2 | ++; just stable, slightly sedimented after 24 h |
| 3 | 2− | +++; stable after 24 h, viscosity low |
| 4 | 3 | +++; high viscosity, stable after 24 h |
| 5 | 3-4 | +++; stable after 24 h, viscosity low |
| 6 | 3 | +++; stable after 24 h, viscosity low |
| 7 | 3 | +++; stable after 24 h, viscosity low |
| 8 | 3 | +++; stable after 24 h, viscosity low |
| 9 | 3 | +++; stable after 24 h, viscosity low |

*)Preparation of a 1% strength aqueous polymer stock dispersion

| Evaluation of redispersed rate | Evaluation of the stability/observation: |
|---|---|
| Grade 1: 0-5 min | 0 = not stable, large insoluble fraction |
| Grade 2: 5-20 min | +/− stable, but immediately following preparation |
| Grade 3: 20-60 min | + stable for ca. 1 h |
| Grade 4: >60 min | ++ stable for ca. 24 h |
| Grade 5: insoluble | +++ stable for longer than 24 h |

II. Application-Related Examples

Application Example 1

Hair Gel with PVP K90

| Phase 1: | |
|---|---|
| Polymer from Example No. 1 (1% strength aqueous dispersion) | 50.00 g |
| Additives (perfume, UV absorber, silicone). | |
| Phase 2: | |
| Luviskol ® K90-F (BASF SE) | 3 g |
| Water | 47 g |

Preparation:

Phases 1 and 2 were weighed in separately and homogenized. Phase 2 was then slowly stirred into Phase 1. The mixture was adjusted to pH 7 with triethanolamine. A clear, stable gel was formed.

The example was repeated with the copolymers of Examples 2, 3, 4, 5, 6, 7, 8, 9, 10, 11 and 12. A clear, stable gel was formed.

The invention claimed is:

1. A process for the preparation of a copolymer composition CP) by free-radical copolymerization of a monomer composition comprising
   a) 70 to 100% by weight, based on the total weight of the monomers used for the polymerization, of acrylic acid,
   b) 0 to 30% by weight, based on the total weight of the monomers used for the polymerization, of at least one hydrophilic nonionic compound, different from a), having a free-radically polymerizable, α,β-ethylenically unsaturated double bond,
c) 0 to 1% by weight, based on the total weight of the monomers used for the polymerization, of at least one free-radically polymerizable crosslinking compound which comprises at least two α,β-ethylenically unsaturated double bonds per molecule,
by the method of precipitation polymerization in the presence of an auxiliary composition
H) comprising
H1) at least one compound with a block structure which comprises at least one hydrophobic group and at least one hydrophilic group, and is
selected from compounds of the general formulae $(A)_n\text{-}X\text{---}(B)_m$     (I)

$[A\text{-}X]_p\text{---}B$     (II)

$(A)\text{-}[X\text{---}B]_q$     (III)

in which
n is an integer of at least 1,
m is an integer of at least 1,
p is an integer of at least 2,
q is an integer of at least 2,
A is a hydrophobic group, where
   in the compounds of the formulae (I) and (II), the groups A can in each case have identical or different meanings and in each case have one binding site to the group X,
   in the compounds of the formula (III), the group A has q binding sites to each of the groups X,
X in the compounds of the formula (I) is a chemical bond or a (n+m) valent organic radical and in the compounds of the formulae (II) and (III) is a chemical bond or a bivalent organic radical,
B is a hydrophilic group,
and wherein
   H1) comprises polyisobutenyl groups prepared from polyisobutenes which are selected from:
     high-reactivity polyisobutenes,
     polyisobutenes with at least one nitrogen-containing end group,
     polyisobutenyl alcohols,
     polyisobutenyl aldehydes,
     polyisobutenes having at least one carboxylic acid end group or a derivative thereof,
     mixtures of two or more than two of the aforementioned compounds, and
H2) at least one basic compound different from H1).

2. The process according to claim 1, where the monomer composition used for the preparation of the copolymer composition CP) comprises
a) 70 to 99.99% by weight, based on the total weight of the monomers used for the polymerization, of acrylic acid,
b) 0 to 29.99% by weight, based on the total weight of the monomers used for the polymerization, of at least one hydrophilic nonionic compound, different from a), having a free-radically polymerizable, α,β-ethylenically unsaturated double bond,
c) 0.01 to 1% by weight, based on the total weight of the monomers used for the polymerization, of at least one free-radically polymerizable crosslinking compound which comprises at least two α,β-ethylenically unsaturated double bonds per molecule.

3. The process according to claim 1, where the hydrophilic group is selected from
polyethylene oxide-containing groups,
polypropylene oxide-containing groups,
poly(ethylene oxide/propylene oxide)-containing groups,
polyethyleneimine-containing groups,
polysorbate-containing groups,
polyglycerol-containing groups,
polyvinylpyrrolidone-containing groups,
and combinations thereof.

4. The process according to claim 1, where the group X is selected from groups of the formulae:

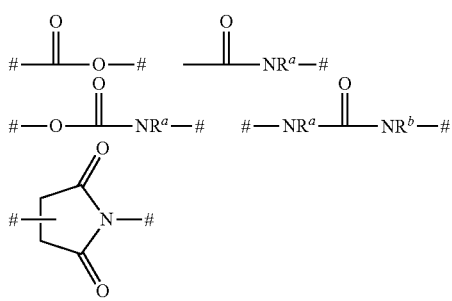

where # in each group X stands once for a binding site to a group A and once for a binding site to a group B,
$R^a$ and $R^b$, independently of one another, are hydrogen, alkyl, cycloalkyl, heterocycloalkyl, aryl or hetaryl.

5. The process according to claim 1, where the compound with a block structure H1) is selected from the group consisting of: polyisobutenyl alcohol alkoxylates, polyisobutenyl amine alkoxylates, reaction products of at least one polyisobutene with at least one carboxylic acid end group or a derivative thereof and at least one polyalkylene oxide with a terminal group reactive towards anhydride groups, silicone compounds which have at least one polyether group, or reaction products of at least one compound which comprises at least one hydrophobic group and at least one group reactive towards isocyanate groups, at least one compound which comprises at least one hydrophilic group and at least one group reactive towards isocyanate groups, and at least one polyisocyanate.

6. The process according to claim 1, where the auxiliary H1) comprises a reaction product of PIBSA and a polyethylene oxide monomethyl ether or a reaction product of PIBSA and a polyethylene oxide monomethyl ether.

7. The process according to claim 1, where the component H2) is selected from basic compounds, different from H1), which have at least one nitrogen-atom-containing group which is selected from amine groups and ammonium groups.

8. The process according to claim 7, where the component H2) is selected from $NH_3$, $(NH_4)_2CO_3$, $NH_4HCO_3$, monoalkylamines, dialkylamines, trialkylamines, amino alcohols, nitrogen-containing heterocycles and mixtures thereof.

9. The process according to claim 7, where the component H2) comprises ammonium hydrogencarbonate or ammonium hydrogencarbonate.

10. The process according to claim 1, where the reaction mixture used for the preparation of the copolymer composition CP) throughout the entire course of the copolymerization has a water content of at most 5% by weight, preferably at most 3% by weight, in particular at most 2% by weight.

11. The process according to claim 1, where the monomer composition used for the preparation of the copolymer composition CP) comprises, as nonionic hydrophilic component b), at least one monomer b1) which is selected from α,β-ethylenically unsaturated amide-group-containing compounds of the general formula (IV)

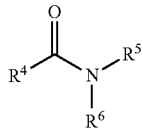
(IV)

where
- one of the radicals $R^4$ to $R^6$ is a group of the formula $CH_2=CR^7-$ where $R^7=H$ or $C_1$-$C_4$-alkyl and the other radicals $R^4$ to $R^6$, independently of one another, are H, alkyl, cycloalkyl, heterocycloalkyl, aryl or hetaryl,
- where $R^4$ and $R^5$, together with the amide group to which they are bonded, may also be a lactam having 5 to 8 ring atoms,
- where $R^5$ and $R^6$, together with the nitrogen atom to which they are bonded, may also be a five- to seven-membered heterocycle,
- with the proviso that the sum of the carbon atoms of the radicals $R^4$, $R^5$ and $R^6$ is at most 8.

12. The process according to claim 1, where the monomer composition used for the preparation of the copolymer composition CP) comprises, as hydrophilic nonionic component b), at least one monomer b2) which has a group of the formulae (IIIa) or (IIIb)

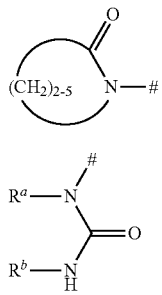

in which
- # is the binding site to a group with a free-radically polymerizable, α,β-ethylenically unsaturated double bond, where in the compounds (IIIa) # is not the binding site to a group of the formula $CH_2=CR^7-$ where $R^7=H$ or $C_1$-$C_4$-alkyl,
- $R^a$ is H or $C_1$-$C_4$-alkyl,
- $R^b$ is H or $C_1$-$C_4$-alkyl, or
- $R^a$ and $R^b$ together are $(CH_2)_{1-4}$.

13. The process according to claim 1, where the monomer composition used for the preparation of the copolymer composition CP) comprises, as hydrophilic nonionic component b), at least one monomer b3) which is selected from esters of α,β-ethylenically unsaturated mono- and dicarboxylic acids with $C_2$-$C_{30}$-diols, amides of α,β-ethylenically unsaturated mono- and dicarboxylic acids with $C_2$-$C_{30}$-amino alcohols which have a primary or secondary amino group, and mixtures thereof.

14. The process according to claim 1, where the monomer composition used for the preparation of the copolymer composition CP) comprises, as hydrophilic nonionic component b), at least one monomer b4) which is selected from compounds of the general formulae VI a) and VI b)

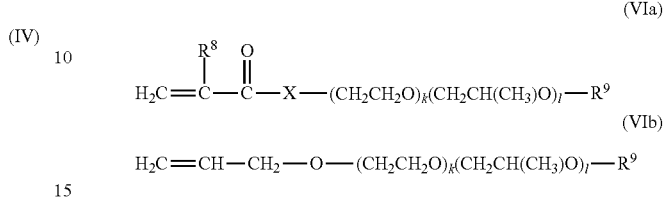

in which
- the order of the alkylene oxide units is arbitrary,
- k and l, independently of one another, are an integer from 0 to 1000, where the sum of k and l is at least 5,
- $R^8$ is hydrogen or $C_1$-$C_8$-alkyl,
- $R^9$ is hydrogen, $C_1$-$C_{30}$-alkyl, $C_2$-$C_{30}$-alkenyl or $C_5$-$C_8$-cycloalkyl,
- X is O or a group of the formula $NR^{10}$, in which $R^{10}$ is H, alkyl, alkenyl, cycloalkyl, heterocycloalkyl, aryl or hetaryl.

15. The process according to claim 1, where the monomer composition used for the preparation of the copolymer composition CP) additionally comprises at least one compound d) having a free-radically polymerizable, α,β-ethylenically unsaturated double bond and at least one cationogenic and/or cationic group per molecule.

16. The process according to claim 1, where the monomer composition used for the preparation of the copolymer composition CP) additionally comprises at least one compound e), different from acrylic acid, having a free-radically polymerizable, α,β-ethylenically unsaturated double bond and at least one anionogenic and/or anionic group per molecule.

17. The process according to claim 1, where the monomer composition used for the preparation of the copolymer composition CP) additionally comprises at least one compound f) which is selected from esters of α,β-ethylenically unsaturated mono- and dicarboxylic acids with $C_1$-$C_{30}$-alkanols, amides of α,β-ethylenically unsaturated mono- and dicarboxylic acids with mono- and di-($C_1$-$C_{30}$-alkyl)amines, N,N-diallylamines, their acid addition salts and quaternization products, N,N-diallyl-N-alkylamines, their acid addition salts and quaternization products, urethane(meth)acrylates with alkylene oxide groups, esters of vinyl alcohol and allyl alcohol with $C_1$-$C_{30}$-monocarboxylic acids, $C_1$-$C_{30}$-alkyl vinyl ethers, vinyl aromatics, vinyl halides, vinylidene halides, $C_2$-$C_8$-monoolefins, nonaromatic hydrocarbons with at least two conjugated double bonds and mixtures thereof.

18. The process according to claim 1, where the polymerization takes place in an anhydrous, aprotic solvent or solvent mixture, preferably in a mixture of cyclohexane and ethyl acetate.

19. A copolymer composition CP) obtained by the process as defined in claim 1.

20. A method of modifying rheological properties of an aqueous composition, said process comprising the incorporation of a copolymer composition CP) obtained according to claim 1.

21. A cosmetic composition comprising
A) at least one copolymer composition CP) obtained by the process as defined in claim 1, B) at least one cosmetically acceptable active ingredient and C) optionally at least one further cosmetically acceptable auxiliary different from CP) and B).

22. The composition according to claim 21 in the form of a gel.

23. A pharmaceutical composition comprising

A) at least one copolymer composition obtained by the process as defined in claim 1, B) at least one pharmaceutically acceptable active ingredient and C) optionally at least one further pharmaceutically acceptable auxiliary different from A) and B).

24. A method of modifying rheological properties in the food sector, said process comprising the process according to claim 20.

25. A process for the preparation of a copolymer composition CP) by free-radical copolymerization of a monomer composition comprising a) 70 to 100% by weight, based on the total weight of the monomers used for the polymerization, of acrylic acid, b) 0 to 30% by weight, based on the total weight of the monomers used for the polymerization, of at least one hydrophilic nonionic compound, different from a), having a free-radically polymerizable, $\alpha,\beta$-ethylenically unsaturated double bond, c) 0 to 1% by weight, based on the total weight of the monomers used for the polymerization, of at least one free-radically polymerizable crosslinking compound which comprises at least two $\alpha,\beta$-ethylenically unsaturated double bonds per molecule, by the method of precipitation polymerization in the presence of an auxiliary composition H) comprising H1) at least one compound with a block structure which comprises polytetrahydrofuran groups as hydrophobic groups and at least one hydrophilic group, and H2) at least one basic compound which comprises ammonium hydrogencarbonate.

26. The process according to claim 25, where the compound with a block structure H1) is selected from urethane compounds which comprise, in incorporated form, p1) at least one polytetrahydrofuran which has at least one group reactive towards isocyanate groups, p2) at least one compound which comprises at least one hydrophilic group and at least one group reactive towards isocyanate groups, and p3) at least one polyisocyanate.

27. A method of modifying rheological properties of an aqueous composition, said process comprising the incorporation of a copolymer composition CP) obtained according to claim 25.

28. A method of modifying rheological properties in the food sector, said process comprising the process according to claim 27.

* * * * *